(12) United States Patent
Humphrey

(10) Patent No.: US 10,610,367 B2
(45) Date of Patent: *Apr. 7, 2020

(54) ARTHROPLASTY COMPONENTS

(71) Applicant: DELTOID, LLC, Eagle, ID (US)

(72) Inventor: C. Scott Humphrey, Eagle, ID (US)

(73) Assignee: United Orthopedic Corp. (TW)

( * ) Notice: Subject to any disclaimer, the term of this patent is extended or adjusted under 35 U.S.C. 154(b) by 74 days.

This patent is subject to a terminal disclaimer.

(21) Appl. No.: 15/940,542

(22) Filed: Mar. 29, 2018

(65) Prior Publication Data

US 2018/0280151 A1  Oct. 4, 2018

Related U.S. Application Data

(63) Continuation of application No. 15/263,012, filed on Sep. 12, 2016, now Pat. No. 9,962,266.
(Continued)

(51) Int. Cl.
*A61F 2/40* (2006.01)
*A61F 2/30* (2006.01)

(52) U.S. Cl.
CPC ........ *A61F 2/4003* (2013.01); *A61F 2/30942* (2013.01); *A61F 2/4014* (2013.01); *A61F 2/4081* (2013.01); *A61F 2002/30013* (2013.01); *A61F 2002/30092* (2013.01); *A61F 2002/30253* (2013.01); *A61F 2002/30616* (2013.01); *A61F 2002/30878* (2013.01); *A61F 2002/30881* (2013.01); *A61F 2002/30884* (2013.01); *A61F 2002/30891* (2013.01); *A61F 2002/30899* (2013.01); *A61F 2002/30948* (2013.01);
(Continued)

(58) Field of Classification Search
CPC .. A61F 2/40; A61F 2/4014; A61F 2002/4018; A61F 2/4003; A61F 2/4081
See application file for complete search history.

(56) References Cited

U.S. PATENT DOCUMENTS 3,891,998 A    7/1975 Lennox
4,231,120 A    11/1980 Day
(Continued)

FOREIGN PATENT DOCUMENTS

EP    2604226 A1    6/2013
EP    2689750 A1    1/2014
(Continued)

OTHER PUBLICATIONS http://www.lima.it/repository/fck/image/Lima.
(Continued)

*Primary Examiner* — Jason-Dennis N Stewart
(74) *Attorney, Agent, or Firm* — McNees Wallace & Nurick LLC

(57) ABSTRACT

Systems, kits and methods for long bone arthroplasty that include arrays of humeral head prosthesis components, each having on a first side a bone articulation surface that has an overall generally hemi elliptical convex shape defined by a major axis and a minor axis, the bone articulation surface having an apex and a base that each has an non-circular elliptical cross sectional shape, the prosthesis components having on an opposite side, adjacent the base, a bone contact surface. The humeral head prosthesis components in the arrays vary from having a base with a more circular cross sectional shape to a more elongated elliptical cross sectional shape with increasing size.

20 Claims, 33 Drawing Sheets

Related U.S. Application Data

(60) Provisional application No. 62/217,695, filed on Sep. 11, 2015, provisional application No. 62/217,703, filed on Sep. 11, 2015.

(52) U.S. Cl.
CPC .......... *A61F 2002/4007* (2013.01); *A61F 2220/0016* (2013.01); *A61F 2230/0076* (2013.01); *A61F 2310/00023* (2013.01); *A61F 2310/00029* (2013.01); *A61F 2310/00161* (2013.01); *A61F 2310/00796* (2013.01); *H05K 999/99* (2013.01)

(56) References Cited

U.S. PATENT DOCUMENTS

| | | |
|---|---|---|
| D258,968 S | 4/1981 | Adler |
| 4,261,062 A | 4/1981 | Amstutz et al. |
| D285,969 S | 9/1986 | Kinnett |
| 4,865,605 A | 9/1989 | Dines et al. |
| 4,919,670 A | 4/1990 | Dale et al. |
| 4,964,865 A | 10/1990 | Burkhead et al. |
| 5,032,132 A | 7/1991 | Matsen, III et al. |
| 5,080,673 A | 1/1992 | Burkhead et al. |
| 5,370,703 A | 12/1994 | Willert et al. |
| 5,383,936 A | 1/1995 | Kubein-Meesenburg et al. |
| 5,489,309 A | 2/1996 | Lackey et al. |
| 5,593,448 A | 1/1997 | Dong |
| 5,702,447 A | 12/1997 | Walch et al. |
| 5,702,457 A | 12/1997 | Walch et al. |
| 5,723,018 A | 3/1998 | Cyprien et al. |
| 5,800,551 A | 9/1998 | Williamson et al. |
| 6,187,050 B1 | 2/2001 | Khalili et al. |
| 6,197,062 B1 | 3/2001 | Fenlin |
| 6,228,119 B1 | 5/2001 | Ondrla et al. |
| 6,364,910 B1 | 4/2002 | Shultz et al. |
| 6,368,353 B1 | 4/2002 | Arcand |
| 6,379,386 B1 | 4/2002 | Resch |
| 6,406,495 B1 | 6/2002 | Schoch |
| 6,508,840 B1 | 1/2003 | Rockwood, Jr. et al. |
| 6,514,287 B2 | 2/2003 | Ondrla et al. |
| 6,537,321 B1 | 3/2003 | Horber |
| 6,673,115 B2 | 1/2004 | Resch et al. |
| 6,679,916 B1 | 1/2004 | Frankle et al. |
| 6,699,289 B2 | 3/2004 | Iannotti et al. |
| 6,719,799 B1 | 4/2004 | Kropf |
| 6,783,549 B1 | 8/2004 | Stone et al. |
| 6,790,234 B1 | 9/2004 | Frankle |
| 6,911,047 B2 | 6/2005 | Rockwood, Jr. et al. |
| 6,942,699 B2 | 9/2005 | Stone et al. |
| 6,953,478 B2 | 10/2005 | Bouttens et al. |
| 7,044,973 B2 | 5/2006 | Rockwood, Jr. et al. |
| 7,160,328 B2 | 1/2007 | Rockwood, Jr. et al. |
| 7,175,663 B1 | 2/2007 | Stone |
| 7,329,284 B2 | 2/2008 | Maroney et al. |
| 7,462,197 B2 | 12/2008 | Tornier et al. |
| 7,470,287 B2 | 12/2008 | Tornier et al. |
| 7,604,665 B2 | 10/2009 | Iannotti et al. |
| 7,621,961 B2 | 11/2009 | Stone |
| 7,648,530 B2 | 1/2010 | Habermeyer et al. |
| 7,753,959 B2 | 7/2010 | Berelsman et al. |
| 7,819,923 B2 | 10/2010 | Stone et al. |
| 7,854,768 B2 | 12/2010 | Wiley et al. |
| 7,879,275 B2 | 2/2011 | Smith et al. |
| 7,892,287 B2 | 2/2011 | Deffenbaugh |
| 7,922,769 B2 | 4/2011 | Deffenbaugh et al. |
| 7,959,680 B2 | 6/2011 | Stone et al. |
| 7,981,161 B2 | 7/2011 | Choi et al. |
| 8,007,538 B2 | 8/2011 | Gunther |
| 8,014,984 B2 | 9/2011 | Iannotti et al. |
| 8,038,719 B2 | 10/2011 | Gunther |
| 8,048,161 B2 | 11/2011 | Guederian et al. |
| 8,062,376 B2 | 11/2011 | Shultz et al. |
| 8,070,820 B2 | 12/2011 | Winslow et al. |
| 8,080,063 B2 | 12/2011 | Ferrand et al. |
| 8,182,542 B2 | 5/2012 | Ferko |
| 8,236,059 B2 | 8/2012 | Stone et al. |
| 8,246,687 B2 | 8/2012 | Katrana et al. |
| 8,287,600 B2 | 10/2012 | Angibaud |
| 8,317,871 B2 | 11/2012 | Stone et al. |
| 8,380,471 B2 | 2/2013 | Iannotti et al. |
| 8,419,798 B2 | 4/2013 | Ondrla et al. |
| 8,425,614 B2 | 4/2013 | Winslow et al. |
| 8,449,617 B1 | 5/2013 | McDaniel et al. |
| 8,454,702 B2 | 6/2013 | Smits et al. |
| 8,480,750 B2 | 7/2013 | Long |
| 8,506,638 B2 | 8/2013 | Vanasse et al. |
| 8,512,410 B2 | 8/2013 | Metcalfe et al. |
| 8,529,629 B2 | 9/2013 | Angibaud et al. |
| 8,545,511 B2 | 10/2013 | Splieth et al. |
| 8,556,980 B2 | 10/2013 | Deffenbaugh |
| 8,608,805 B2 | 12/2013 | Forrer et al. |
| 8,632,598 B2 | 1/2014 | McDaniel et al. |
| 8,663,335 B2 | 3/2014 | Katrana et al. |
| 8,673,015 B2 | 3/2014 | Maroney et al. |
| 8,690,952 B2 | 4/2014 | Dallmann |
| 8,696,677 B2 | 4/2014 | Chavarria et al. |
| 8,702,804 B2 | 4/2014 | Smith et al. |
| 8,721,726 B2 | 5/2014 | Capon et al. |
| 8,721,727 B2 | 5/2014 | Ratron et al. |
| 8,721,728 B2 | 5/2014 | Winslow et al. |
| 8,778,028 B2 | 7/2014 | Gunther et al. |
| 8,845,742 B2 | 9/2014 | Kusogullari et al. |
| 8,845,750 B2 | 9/2014 | Slavitt |
| 8,876,907 B2 | 11/2014 | Baptista et al. |
| 8,882,845 B2 | 11/2014 | Wirth et al. |
| 8,920,508 B2 | 12/2014 | Iannotti et al. |
| 8,932,361 B2 | 1/2015 | Tornier et al. |
| 9,474,619 B2 | 10/2016 | Reubelt et al. |
| 9,512,445 B2 | 12/2016 | Iannotti |
| 2001/0011192 A1 | 8/2001 | Ondrla et al. |
| 2001/0037153 A1 | 11/2001 | Rockwood, Jr. et al. |
| 2002/0082702 A1 | 6/2002 | Resch et al. |
| 2003/0097183 A1 | 5/2003 | Rauscher et al. |
| 2003/0114933 A1 | 6/2003 | Bouttens et al. |
| 2003/0125809 A1 | 7/2003 | Iannotti et al. |
| 2004/0059424 A1 | 3/2004 | Guederian et al. |
| 2004/0064189 A1 | 4/2004 | Maroney et al. |
| 2004/0225367 A1 | 11/2004 | Glien et al. |
| 2005/0060039 A1 | 3/2005 | Cyprien |
| 2005/0107882 A1 | 5/2005 | Stone et al. |
| 2005/0209700 A1 | 9/2005 | Rockwood |
| 2005/0261775 A1 | 11/2005 | Baum et al. |
| 2005/0288791 A1 | 12/2005 | Tornier et al. |
| 2006/0009852 A1 | 1/2006 | Winslow et al. |
| 2006/0069444 A1 | 3/2006 | Deffenbaugh |
| 2006/0079963 A1 | 4/2006 | Hansen |
| 2006/0111787 A1 | 5/2006 | Bailie et al. |
| 2006/0195194 A1 | 8/2006 | Gunther |
| 2007/0016304 A1 | 1/2007 | Chudik |
| 2007/0055380 A1 | 3/2007 | Berelsman et al. |
| 2007/0142917 A1 | 6/2007 | Roche et al. |
| 2007/0179624 A1 | 8/2007 | Stone et al. |
| 2007/0198094 A1 | 8/2007 | Berelsman et al. |
| 2007/0219637 A1 | 9/2007 | Berelsman et al. |
| 2007/0225818 A1 | 9/2007 | Reubelt et al. |
| 2007/0225821 A1 | 9/2007 | Reubelt et al. |
| 2007/0244564 A1 | 10/2007 | Ferrand et al. |
| 2008/0140211 A1 | 6/2008 | Doubler et al. |
| 2009/0062923 A1 | 3/2009 | Swanson |
| 2009/0125113 A1 | 5/2009 | Guederian et al. |
| 2009/0149961 A1 | 6/2009 | Dallmann |
| 2010/0016975 A1 | 1/2010 | Iannotti et al. |
| 2010/0087876 A1 | 4/2010 | Gunther |
| 2010/0087877 A1 | 4/2010 | Gunther |
| 2010/0087927 A1 | 4/2010 | Roche et al. |
| 2010/0145393 A1 | 6/2010 | Fallin et al. |
| 2010/0211183 A1 | 8/2010 | Chi |
| 2010/0228352 A1 | 9/2010 | Courtney, Jr. et al. |
| 2010/0249938 A1 | 9/2010 | Gunther et al. |
| 2010/0274359 A1 | 10/2010 | Brunnarius et al. |
| 2011/0035013 A1 | 2/2011 | Winslow et al. |
| 2011/0035018 A1 | 2/2011 | Deffenbaugh et al. |
| 2011/0054625 A1 | 3/2011 | Ferko et al. |

(56) References Cited

U.S. PATENT DOCUMENTS

| | | |
|---|---|---|
| 2011/0112648 A1 | 5/2011 | Gunther |
| 2011/0118846 A1 | 5/2011 | Katrana et al. |
| 2011/0125273 A1 | 5/2011 | Ratron et al. |
| 2011/0144758 A1 | 6/2011 | Deffenbaugh |
| 2011/0178603 A1 | 7/2011 | Long |
| 2011/0276144 A1 | 11/2011 | Wirth et al. |
| 2012/0029647 A1 | 2/2012 | Winslow et al. |
| 2012/0089233 A1 | 4/2012 | Capon et al. |
| 2012/0109321 A1 | 5/2012 | Stone et al. |
| 2012/0130498 A1 | 5/2012 | Long |
| 2012/0130499 A1 | 5/2012 | Long |
| 2012/0179262 A1 | 7/2012 | Metcalfe et al. |
| 2012/0209392 A1 | 8/2012 | Angibaud et al. |
| 2012/0221111 A1 | 8/2012 | Burkhead, Jr. et al. |
| 2012/0232667 A1 | 9/2012 | Katrana et al. |
| 2012/0239051 A1 | 9/2012 | De Wilde et al. |
| 2012/0253467 A1 | 10/2012 | Frankle |
| 2012/0277880 A1 | 11/2012 | Winslow et al. |
| 2012/0296439 A1 | 11/2012 | Slavitt |
| 2013/0060341 A1 | 3/2013 | Tornier et al. |
| 2013/0066433 A1 | 3/2013 | Veronesi et al. |
| 2013/0090736 A1 | 4/2013 | Katrana et al. |
| 2013/0090737 A1 | 4/2013 | Flaherty et al. |
| 2013/0123929 A1 | 5/2013 | McDaniel et al. |
| 2013/0166033 A1 | 6/2013 | Gunther |
| 2013/0173007 A1 | 7/2013 | Duport |
| 2013/0178943 A1 | 7/2013 | Duport |
| 2013/0190881 A1 | 7/2013 | Winslow et al. |
| 2013/0197651 A1 | 8/2013 | McDaniel et al. |
| 2013/0245775 A1 | 9/2013 | Metcalfe |
| 2013/0261629 A1 | 10/2013 | Anthony et al. |
| 2013/0261750 A1 | 10/2013 | Lappin |
| 2013/0261755 A1 | 10/2013 | Anthony et al. |
| 2013/0297030 A1 | 11/2013 | Katrana |
| 2013/0325131 A1 | 12/2013 | Roche et al. |
| 2013/0333187 A1 | 12/2013 | Long |
| 2014/0005789 A1 | 1/2014 | Chavarria et al. |
| 2014/0025173 A1 | 1/2014 | Cardon et al. |
| 2014/0031945 A1 | 1/2014 | Baptista et al. |
| 2014/0128983 A1 | 5/2014 | Flaherty et al. |
| 2014/0180425 A1 | 6/2014 | Katrana et al. |
| 2014/0214170 A1 | 7/2014 | Ratron et al. |
| 2014/0236304 A1 | 8/2014 | Hodorek et al. |
| 2014/0249638 A1 | 9/2014 | Winslow et al. |
| 2014/0277520 A1 | 9/2014 | Chavarria et al. |
| 2015/0012103 A1 | 1/2015 | Winslow et al. |
| 2015/0025641 A1 | 1/2015 | Masson |
| 2015/0025642 A1 | 1/2015 | Wirth et al. |

FOREIGN PATENT DOCUMENTS

| | | |
|---|---|---|
| EP | 2672929 A4 | 1/2018 |
| WO | WO03005933 A2 | 1/2003 |
| WO | WO03005933 A3 | 1/2003 |
| WO | WO2011073169 A1 | 6/2011 |
| WO | WO2012109245 A2 | 8/2012 |
| WO | WO2012125704 A2 | 9/2012 |
| WO | WO2013148229 A1 | 10/2013 |

OTHER PUBLICATIONS

Anatomical Shoulder System by Zimmer (Product Materials).

DePuy Brochure, Global Advantage Shoulder Arthroplasty System, 2000.

Tornier Affiniti Brochure, The Affiniti Total Shoulder Prosthesis, 2008.

Edwards, Bradley T., MD, et al., Radiographic comparison of pegged and keeled glenoid components using modern cementing techniques: A prospective randomized study, Journal of Shoulder and Elbow Surgery, Elsevier 2010, 251-257, Texas.

Amstutz, Harlan C., et al., UCLA Anatomic Total Shoulder Arthroplasty, Division of Orthopaedic Surgery, UCLA Medical School, Mar. 17, 1980, Los Angeles, CA.

Iannotti, Joseph P., M.D., et al., The Normal Glenohumeral Relationships, An Anatomical Study of One Hundred and Forty Shoulders, Department of Orthopaedic Surgery, University of Pennsylvania, Apr. 1992, vol. 74-A, No. 4, Pennsylvania.

Boileau, P., et al., The Three-Dimensional Geometry of the Proximal Humerus, Implications for Surgical Technique and Prosthetic Design, Department of Orthopaedic Surgery, 1997 British Editorial Society of Bone and Joint Surgery, vol. 79-B, Sep. 5, 1997, Nice and Lyon, France.

Hertel, Ralph, M.D., et al., Geometry of the Proximal Humerus and Implications for Prosthetic Design, Department of Orthopaedic Surgery, Inselspital, University of Berne, Switzerland, 2002.

Harrold, Fraser, M.D., PhD, et al., Humeral Head Arthroplasy and its Ability to Restore Original Humeral Head Geometry, Department of Orthopaedic and Trauma Surgery, Journal of Shoulder and Elbow Surgery, 2013, 115-121, Elsevier, Scotland, UK, 2013.

Jun, Bong Jae, PhD, et al., The Effects of Prosthetic Humeral Head Shape on Glenohumeral Joint Kinematics: A Comparison of Non-Spherical and Spherical Prosthetic Heads to the Native Head, Journal of Shoulder and Elbow Surgery, 2013, 1423-1432, Elsevier, Cleveland, Ohio.

Humeral Head Formulae

For a given length (mm) of $D^F$:

$D^S = 0.69(D^F) + 10.8$, $HHH = 0.30(D^F) + 3.2$, $ROC^F = 0.53(D^F) - 0.5$, and $ROC^S = 0.44(D^F) + 2.2$.

spherical

| Size | Height | S-Dia | CS-Dia | XL Height |
|---|---|---|---|---|
| 1 | 14.8 | 38.2 | 39.5 | 18.80 |
| 2 | 15.6 | 40.2 | 41.5 | 19.60 |
| 3 | 16.3 | 42.1 | 43.5 | 20.30 |
| 4 | 17.1 | 44.1 | 45.5 | 21.10 |
| 5 | 17.8 | 46 | 47.5 | 21.80 |
| 6 | 18.6 | 47.9 | 49.5 | 22.60 |
| 7 | 19.3 | 49.9 | 51.5 | 23.30 |
| 8 | 20.1 | 51.8 | 53.5 | 24.10 |
| 9 | 20.8 | 53.8 | 55.5 | 24.80 | elliptical

| Size | Height | M-L Dia | A-P Dia | Diff | XL Height |
|---|---|---|---|---|---|
| 1 | 14.8 | 38.2 | 37.2 | 1 | 18.80 |
| 2 | 15.6 | 40.2 | 39 | 1.2 | 19.60 |
| 3 | 16.3 | 42.1 | 40.35 | 1.75 | 20.30 |
| 4 | 17.1 | 44.1 | 41.6 | 2.5 | 21.10 |
| 5 | 17.8 | 46 | 42.75 | 3.25 | 21.80 |
| 6 | 18.6 | 47.9 | 43.9 | 4 | 22.60 |
| 7 | 19.3 | 49.9 | 45.15 | 4.75 | 23.30 |
| 8 | 20.1 | 51.8 | 46.3 | 5.5 | 24.10 |
| 9 | 20.8 | 53.8 | 47.55 | 6.25 | 24.80 |

FIG 9

ARTHROPLASTY COMPONENTS

RELATED APPLICATIONS

This application claims the benefit of the filing dates of U.S. patent application Ser. No. 15/263,012, entitled "ARTHROPLASTY COMPONENTS," filed on Sep. 12, 2016, now granted, and U.S. Provisional Patent Application Nos. 62/217,695 entitled "ARRAY OF ELLIPTICALLY SHAPED HUMERAL HEAD IMPLANTS HAVING NON-SPHERICAL ARTICULATING SURFACES THAT VARY WITH INCREASING HUMERAL HEAD SIZE" both filed on Sep. 11, 2015, and 62/217,703 entitled "JOINT PROSTHESES" filed on Sep. 11, 2015, the contents of which are incorporated by reference, in their entireties. This application is related to U.S. patent application Ser. No. 14/586,677 entitled "INSTRUMENTS AND TECHNIQUES FOR ORIENTING PROSTHESIS COMPONENTS FOR JOINT PROSTHESES" filed on Dec. 30, 2014, which claims priority to U.S. Provisional Patent Application Nos. 61/921,593 filed Dec. 30, 2013, and 61/928,399 filed Jan. 16, 2014, and PCT Application No. PCT/US14/72845, filed Dec. 30, 2014.

FIELD

The disclosure relates to the field of joint replacement, and more particularly total shoulder arthroplasty using prosthetic components.

BACKGROUND

Anatomic and Non-Anatomic Shoulder Replacement

In the field of shoulder arthroplasty, there are two general and somewhat competing points of view regarding the state of the patient's anatomy. From the point of view of some clinicians, it is desirable to aim for restoration of the native anatomy through use of prosthetic shoulder components that are shaped in a manner that is anatomically correct, particularly with regards to the shape of the prosthetic humeral head. For others, the higher objective is to aim for adapting and balancing the existing soft tissues, particularly the rotator cuff and musculature, with the shape and orientation of the replacement humeral head, even if the shape of the prosthetic head is not anatomically correct.

The anatomic approach involves restoration of the humeral head to its pre-diseased state, with utilization of spherical humeral head components with proportional diameter and thickness. In contrast, the non-anatomic approach involves humeral head replacement with soft-tissue balancing of the rotator cuff utilizing spherical humeral head components of varying thicknesses. Generally, within the art, reverse shoulder arthroplasty is considered non-anatomic shoulder replacement because the native glenoid side of the shoulder is converted to a sphere to mimic the humerus (glenosphere), while the humeral side is converted to mimic a glenoid (typically through replacement of the humeral head with a cup shaped implant).

Desired features of anatomic implants include replication of humeral neck angle, version, and posterior and medial offset. In the current art, stemmed arthroplasty systems are the most prevalent, and essentially all stemmed arthroplasty systems use spherical humeral heads. The conventional belief is that roughly one-third of a sphere is considered to be the most anatomically correct shape of the current offerings. Regardless of head size, the ratio of the head height to the radius of curvature is about 3:4. Clinical outcomes in patients who have received anatomically correct prostheses are generally regarded as superior when compared to soft-tissue balancing techniques using non-anatomically shaped (i.e., anatomically incorrect) prostheses.

A challenge in the art is the absence of anatomically correct head articulation surfaces. It is known that the native anatomical shape of the humeral head is not spherical, but elliptical (i.e., where the cross section of the humeral head has a radius of curvature in the superior to inferior dimension that is greater than the radius of curvature of the cross section in the anterior to posterior dimension). Recent research has shown that a prosthetic humeral head having a cross sectional shape adjacent to the bone cut that is elliptically-shaped and a generally spherical center point would theoretically allow a patient to have improved shoulder range of motion and function postoperatively. However, because the center of rotation of the humeral head is offset from the long axis of the humeral bone, it has been impractical for any shoulder implant company to create a prosthesis with an elliptically-shaped prosthetic humeral head. Merely coupling an elliptically-shaped head with a traditional stemmed prosthesis design would present difficulties accounting for the surgeon's need to simultaneously achieve the proper head size, correct rotational orientation of the elliptical head, and the proper amount of superior to inferior and anterior to posterior offset relative to the stem. Moreover, in many shoulder surgeries, only the humeral portion of the joint is replaced while the native glenoid is left intact, presenting a challenge of matching the articulating surface of the head prosthetic with the native articulating surface of the glenoid. This challenge is not present in total arthroplasty, where both the humeral and the glenoid portions are replaced with prosthetics.

Ideally, a shoulder arthroplasty system would provide a wide range of head choices and offsets to most precisely match the patient's native anatomy. With such a system, a near perfect match could be achieved in a hemi-arthroplasty, and if the system were modular, could be adapted in a revision to provide an ideal match if the shoulder is converted to either a total arthroplasty or to a reverse shoulder arthroplasty. The current art does not provide such modular systems, thus, to accomplish the desirable offsets with traditional stem designs, whether using spherical or elliptical heads, it would be necessary to stock an essentially infinite inventory of prosthetic heads and/or stems with variable offsets for achieving the desired shape, size and positioning, which is, of course, economically impractical.

SUMMARY

Recent studies suggest that rotational range of motion and glenohumeral joint kinematics might be improved during shoulder arthroplasty by employing a prosthetic humeral head that is elliptical in shape rather than spherical. While previous anatomical studies have documented that the shape of the humeral head is elliptical or ovoid, no study to date has examined whether or not the elliptical shape changes dimensionally with increasing humeral head size. Based on the inventors' unexpected findings about the dimensional relationships of the heads of humerii as the heads increase in size, provided herein in various embodiments are systems and implants for long bone arthroplasty.

In the various embodiments, the system includes humeral head prosthesis components, and an array of humeral head prosthesis components, each prosthesis component in the array having a convex articulation surface that is hemi-elliptical and defined by a major axis, a minor axis, an apex, and a base having an elliptical cross sectional shape defined by a major diameter along the major axis and a minor diameter along the minor axis. Each prosthesis component in the array is characterized by a ratio relationship of the minor diameter divided by the major diameter of the base, each having a major diameter and a minor diameter that is different from each of the other prosthesis components in the array, wherein as the major diameter is increased the ratio of the minor diameter to the major diameter is decreased. The humeral head prosthesis components in the array vary from having a base with a more circular cross sectional shape to a more elongated elliptical cross sectional shape with increasing size.

In some of the various other embodiments, the implants and arrays are characterized by having a minor diameter (in millimeters) that is equal to 0.69 times the major diameter (in millimeters) plus an additional length in millimeters of 10.8 millimeters, plus or minus 3 millimeters.

In some of the various other embodiments, the implants and arrays are characterized by one or more of the features selected from the minor diameter having a length that is equal to (0.69 times the major diameter) plus 10.8 mm, the humeral head prosthesis having a height that is equal to (0.30 times the major diameter) plus 3.2 mm plus or minus 3 mm, the humeral head prosthesis having along the major axis a radius of curvature that is equal to (0.53 times the major diameter) minus 0.5 mm plus or minus 2 mm, the humeral head prosthesis having along the minor axis a radius of curvature that is equal to (0.44 times the major diameter) plus 2.2 mm plus or minus 2 mm.

In some of the various other embodiments, the implants and arrays are characterized by one or more of the features selected from a minor diameter that ranges from about 36 to 51 mm, a major diameter that ranges from about 37 to about 56 mm, a ratio of the minor diameter to the major diameter ranges from 0.87 to 1, an angle of inclination ranges from 120 degrees to 143 degrees, and a height of the humeral head prosthesis ranges from about 12 to 25 mm.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description:

FIG. 9 shows representative height and diameter features of an exemplary array of generally spherical shaped humeral head prostheses and of an exemplary array of generally non-spherical elliptical shaped humeral head prostheses;

Figure 1:
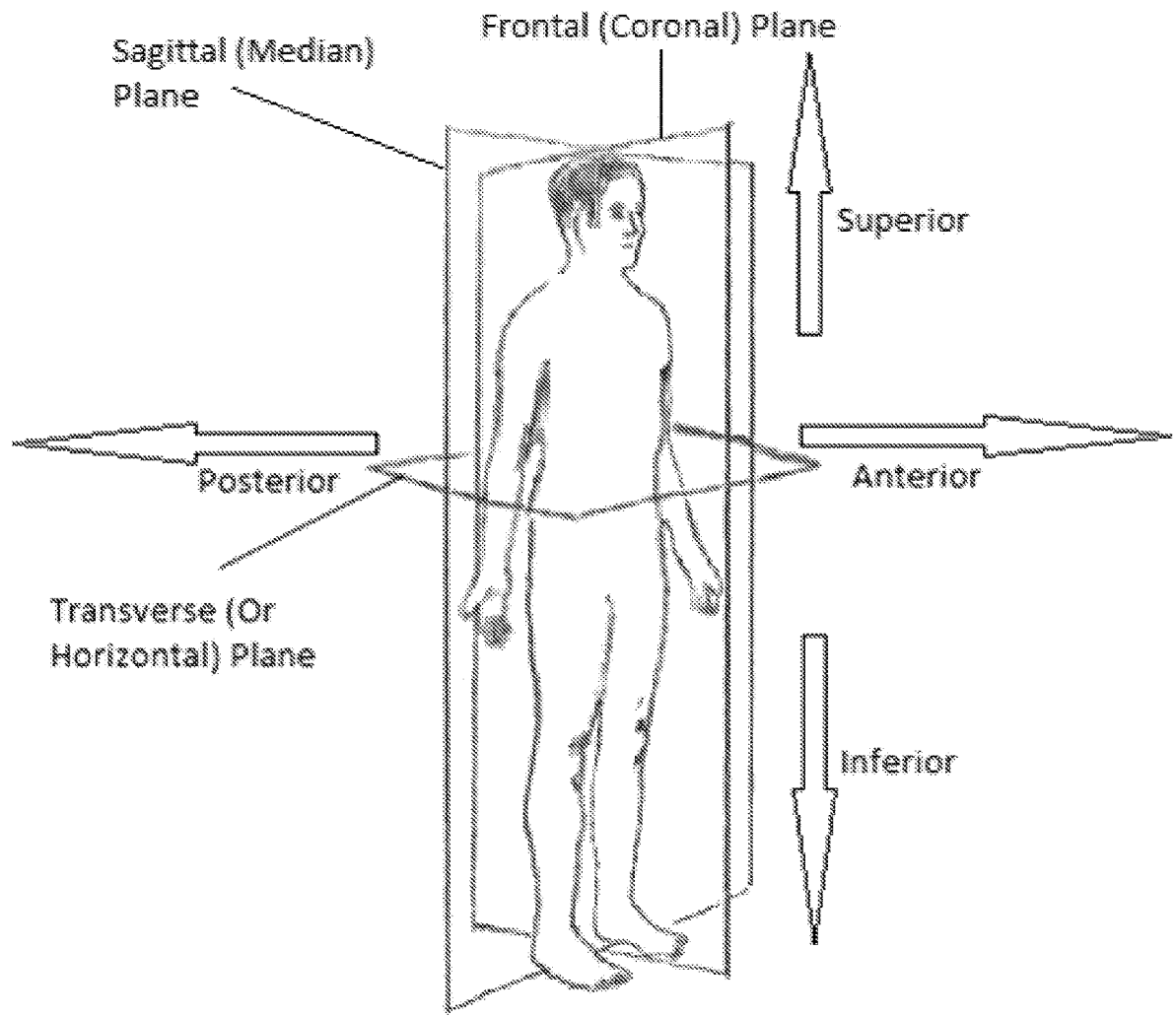
FIG. 1 is a diagram showing the transverse, frontal and sagittal planes in the context of human anatomy.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION

This disclosure describes exemplary embodiments in accordance with the general inventive concepts and is not intended to limit the scope of the invention in any way. Indeed, the invention as described in the specification is broader than and unlimited by the exemplary embodiments and examples set forth herein, and the terms used herein have their full ordinary meaning.

The general inventive concepts are described with occasional reference to the exemplary embodiments and the exemplary embodiments depicted in the drawings. Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts.

Humeral Head Prosthesis

Much emphasis has been placed on replicating normal, prepathologic anatomy during shoulder reconstructive surgery. Use of a prosthetic humeral head that is inaccurately sized or positioned may lead to poor clinical outcomes, including shoulder stiffness and rotator cuff tearing. It has been reported that alterations to humeral head geometry may produce eccentric loading at a prosthetic glenoid that may contribute to early component wear and loosening. And biomechanical studies have confirmed that altering the size and position of the articular surface by as little as 4 or 5 mm changes the kinematics and forces across the glenohumeral joint. Thus, a goal in shoulder arthroplasty is to replicate as closely as possible the size and position of the articular surface at the base of the humeral head so that it is within 3 mm of the normal anatomy.

Figure 13:
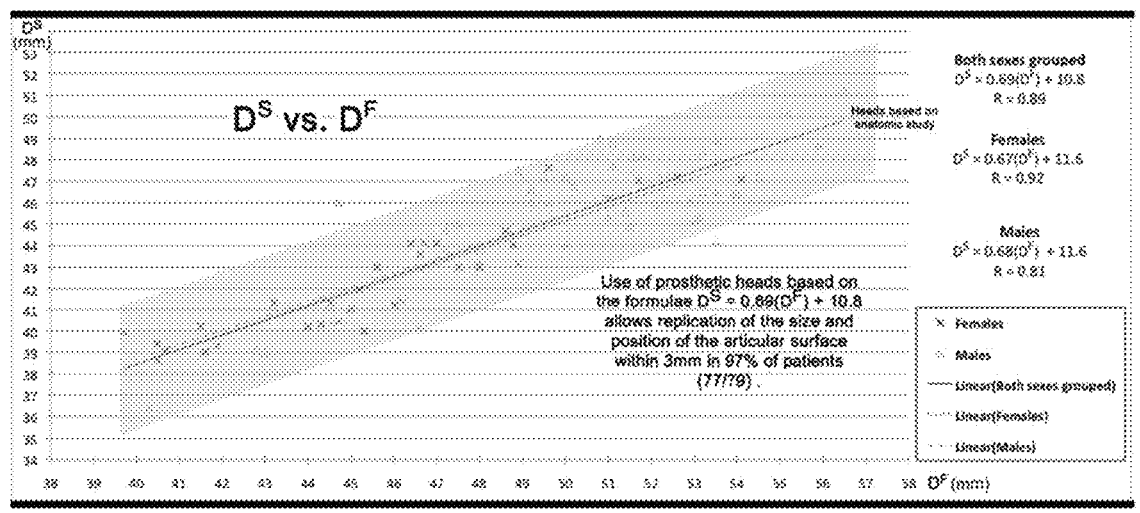
FIG. 13 shows scatter plots with linear trend lines demonstrating in the upper panel graphic the formulae from the anatomical stud and in the lower panel graphic the mathematical relationship between the length difference between the head axes in the frontal and sagittal planes (DF–DS) and the diameter of the base of the head in the frontal plane (DF)
Figure 13:
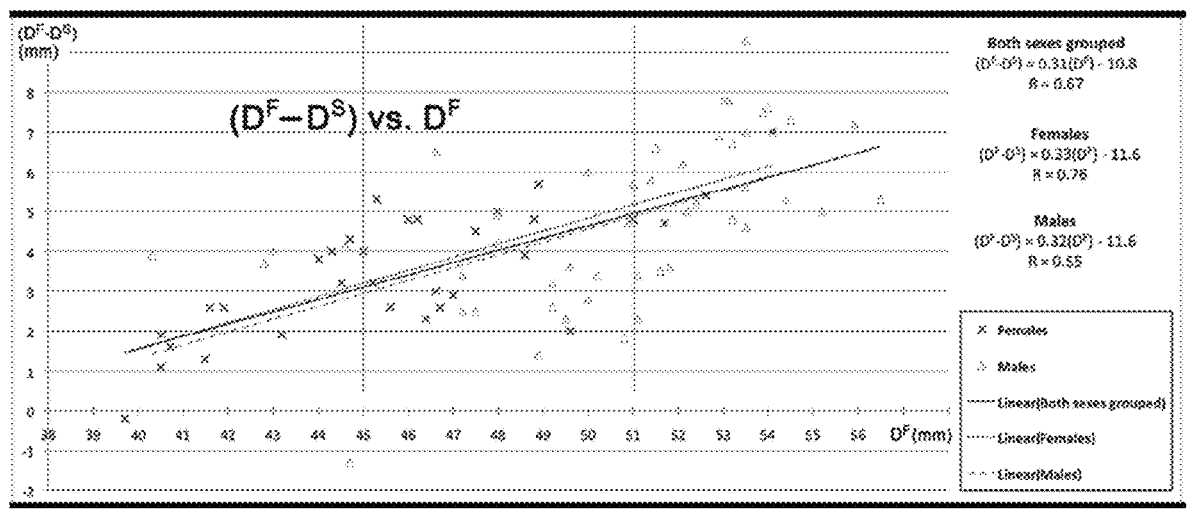

The inventors have made the surprising discovery that the native anatomy of humeral heads varies from what has been conventionally understood. The elliptical shape of the humeral head has been vaguely described and as mentioned herein above, and others have described the average difference between the $D^F$ and $D^S$ measurements at the humeral head base from about 2 mm, to about 3.9 on average. The inventors are the first to show that the elliptical shape of the base of the humeral head seems to elongate in the frontal plane as head size increases, and thus, the relationship between $D^F$ and $D^S$ is not a constant. Referring now to the drawings, the graphic in the upper panel of FIG. 13 reveals that for smaller head sizes ($D^F$<45 mm), the difference between $D^F$ and $D^S$ measurements is always less than or equal to about 4 mm, but once $D^F$ increases to beyond 52 mm, the difference is always >4 mm. Taking this into account, the effect of the mismatch seen with use of a spherical prosthetic head is more likely to be of consequence in patients with larger humeral heads because the patient's size variation is not accounted for by the prosthesis shape, thus the size and position of the articular surface at the base of the prosthetic head will be well outside of the goal of achieving a 3 mm or less deviation from normal anatomy. Referring again to the drawings, the graphic in the lower panel of FIG. 13 compares the formula from the inventors' anatomical study, reported below, versus spherical heads, versus heads with a fixed 4 mm $D^F$ and $D^S$ difference (DF–DS). The shaded grey area is the data plot from the population study +/−3 mm.

Figure 14:
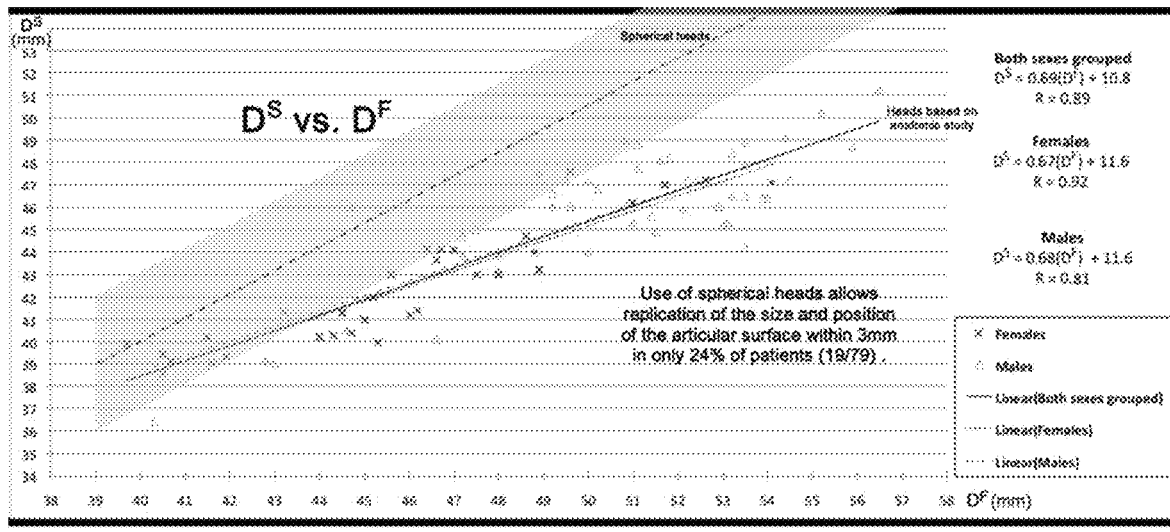
FIG. 14 shows scatter plots with linear trend lines demonstrating in the upper panel graphic the formulae from the anatomical study versus spherical heads, and in the lower panel graphic the formulae from the anatomical study versus heads with a fixed 4 mm difference (DF–DS)
Figure 14:
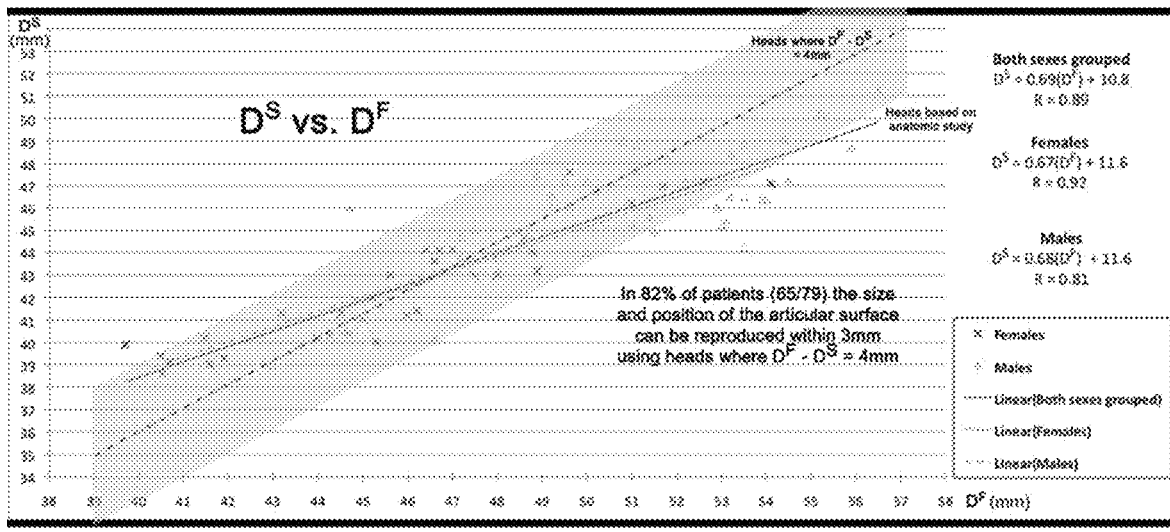

Referring now to FIG. 14 upper panel graphic, the shortcomings of the spherical head design are obvious. The spherical size remains within this +/−3 mm goal range only for the smallest individuals; if the $D^S$ measurement were used in sizing a spherically shaped humeral head during arthroplasty surgery, the mismatch in the $D^F$ direction would be at most 4 mm for a smaller patient, but in larger patients, the mismatch would be 4 mm at a minimum, and it could be >9 mm in some patients. And with respect to elliptical heads having a fixed 4 mm $D^F$ and $D^S$ difference, referring now to FIG. 14 lower panel graphic, the deviation falls within the +/−3 mm goal range for mid sized heads, but not for large or small patients. Similar results would be expected for elliptical humeral heads having a fixed 2 mm DF–DS offsets. Based on the data, such humeral heads would capture more patients than spherical heads, but fewer than 4 mm fixed heads. Based on the data shown in the lower panel graphic of FIG. 13, about 76% of patients receiving spherical heads and about 18% of receiving humeral heads where the measurement $D^F$–$D^S$ is fixed at 4 mm would likely have mismatch in the size and position of the articular surface at the base of the head of greater than 3 mm. For those patients receiving either spherical heads or fixed 4 mm $D^F$–$D^S$ heads with deviations of more than +/−3 mm, the clinical outcomes would likely be compromised. Thus, the inventors have shown that the humeral head prosthesis designs currently known in the art present less than ideal matching to native patient anatomy, both in the case of spherical humeral heads and elliptical humeral heads having constant DF–DS offsets of about 2 mm to about 4 mm.

Based on the newly developed understanding of the relationship of the shape and size of native elliptical humeral heads in the frontal and sagittal planes, the inventors provide here a novel system of humeral head prostheses having anatomically relevant shapes that overcome the shortcomings in the existing art with respect to anatomically relevant shape that can positively influence clinical outcomes for arthroplasty patients. These novel humeral heads have the feature of being hemi elliptical, with either elliptical or spherical apexes and with elliptical bases (essentially at a base that would correspond with the bone cut made at the base of an anatomical head of a humerus).

Referring again to the drawings, FIG. 1 show frontal, sagittal, and horizontal (transverse) planes relative to a human body, and establishes the planes in relation to features of the arthroplasty components as described herein. Generally, the novel arrays of humeral heads herein are characterized by having a diameter in the major axis ($D^F$—corresponding to the frontal plane which transects the joint from superior to inferior) and a diameter in the minor axis ($D^S$—corresponding to the sagittal plane which transects the joint from anterior to posterior), where the difference between the diameter on the major axis minus the minor axis ($D^F$–$D^S$) varies as the measurement $D^F$ increases. As further provided herein and as set forth in the claims, the inventors have described formulae for the novel humeral head array. And as further provided herein and set forth in the claims, the inventors have described other features of relationships between $D^F$ and $D^S$, and the radii of curvature.

According to the various embodiments, provided herein are humeral head prostheses and arrays, wherein a prosthesis selected from the array based on a patient's $D^F$ measurement would have a 97% likelihood of having a 3 mm or less deviation from the size and position of the articular surface at the base of the prosthetic humeral head relative to the patient's normal anatomy.

Figure 2:
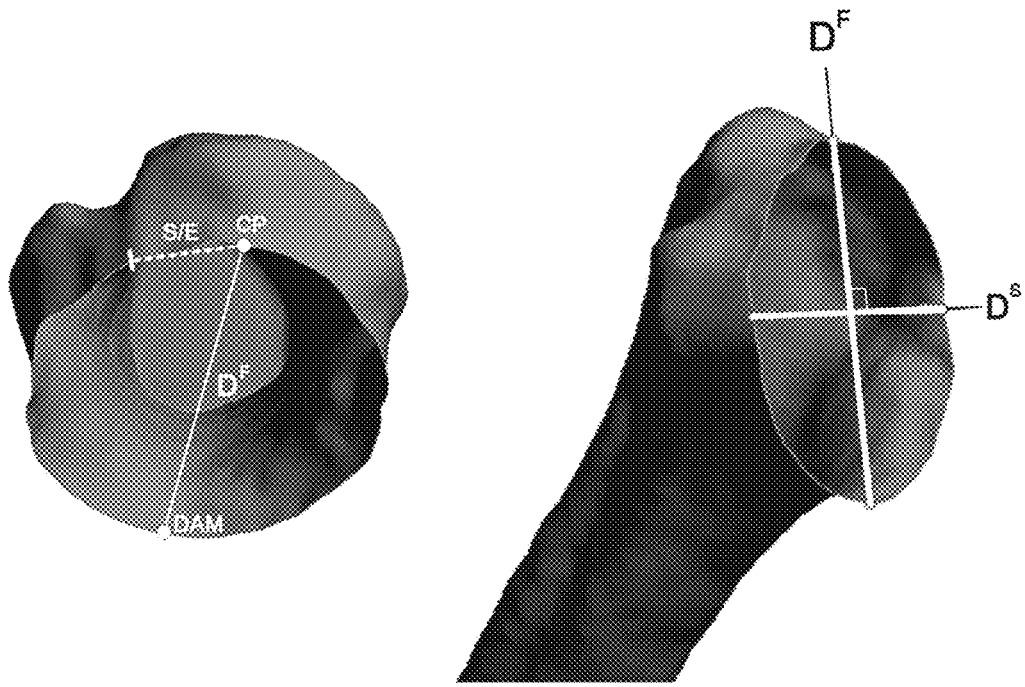
FIG. 2 shows a hemi view of a humeral head prosthesis and alternate frontal and side views of a bone cut line on a humerus, indicating the diameter and radius of curvature of each of the frontal and sagittal planes.
Figure 2:
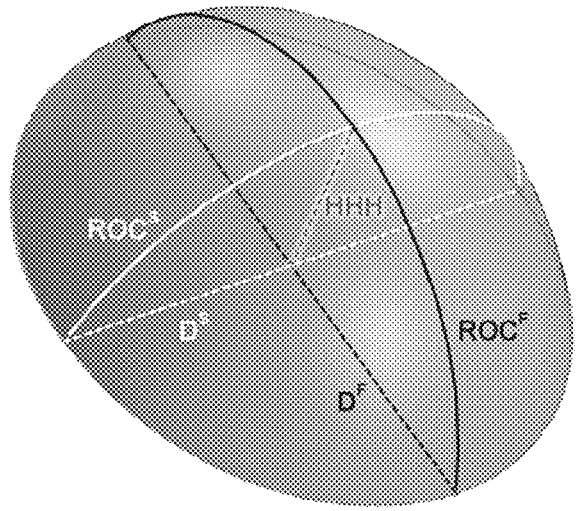

Referring now to FIG. 2, the upper portion shows alternate views of a humerus shown at the bone cut after removal of the anatomical humeral head. The critical point (CP) and the distal articular mid-point (DAM) are identified before the virtual humeral head resection while determining the humeral head equator as described in the literature by Hertel. After humeral head resection, the length of the diameter of the base of the humeral head in the frontal plane (DF) can be measured as the shortest distance between CP and DAM. DS (the length of the diameter of the base of the humeral head in the sagittal plane) bisects and is perpendicular to DF.DF.DS, and the distance between the bicipital sulcus and critical point (S/E) were identified and measured directly on 3D computer models of humerii.

Referring again to FIG. 2 in the lower portion is an image of an elliptically shaped prosthetic humeral head shown together with formulae that describe the features and relationships there between of a natural humeral head. Using the formulae, for any given value of the diameter of the humeral head in the frontal plane (DF—from superior to inferior—dashed black line), the inventors surprisingly discovered through a study of a large number of humeral heads that one may calculate the values of the other humeral head dimensions, including the diameter of the humeral head in the sagittal plane (DS—from anterior to posterior—dashed white line), humeral head height (HHH—dashed gray line), radius of curvature in the frontal plane ($ROC^F$—black arc), and radius of curvature in the sagittal plane (ROCS—white arc).

Figure 3:
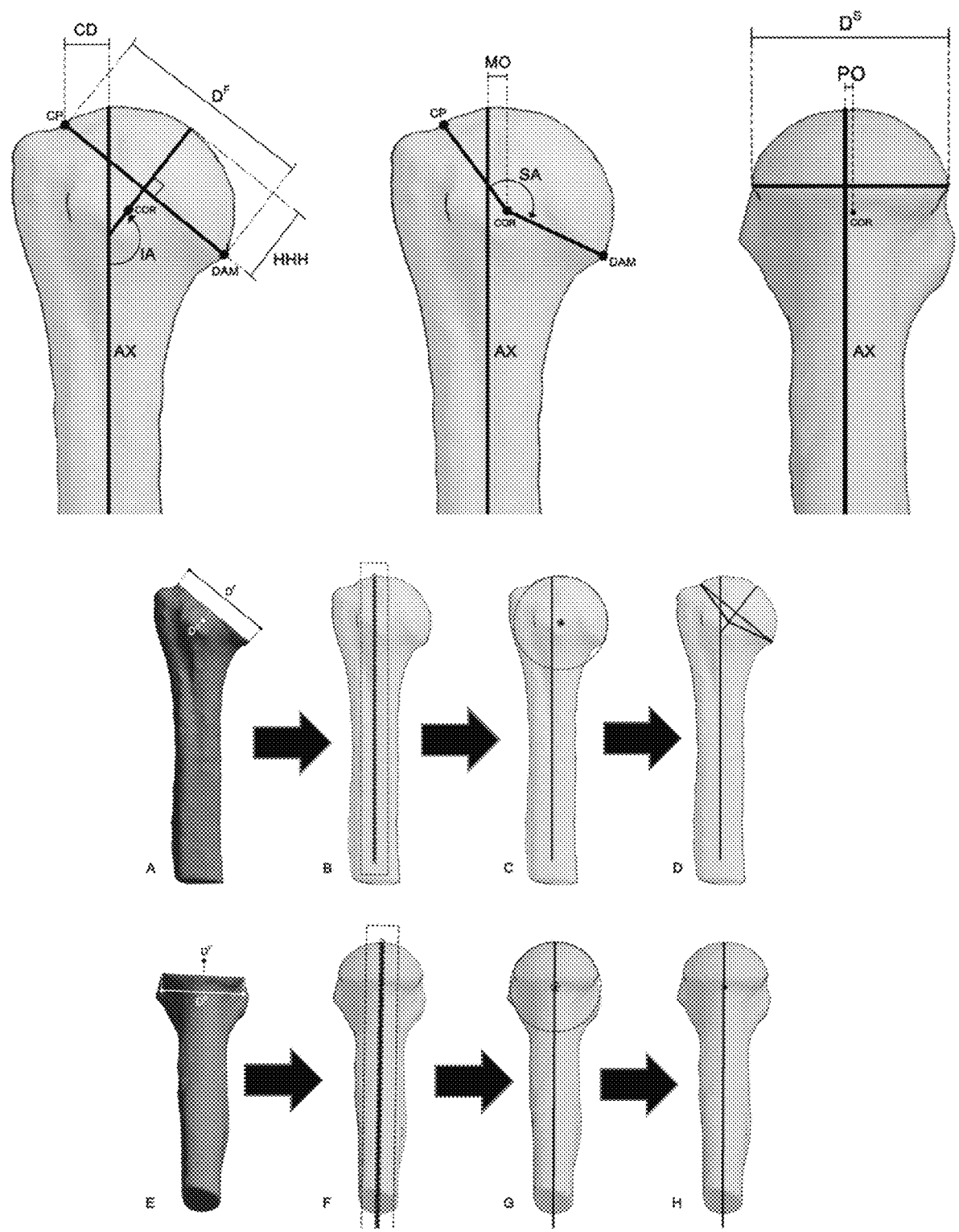
FIG. 3 shows in upper and lower panels alternate front, side and back views of a humerus, indicating key landmarks for determining diameter and radii of curvature to describe the humeral head prosthesis, wherein the lower panel provides stepwise images indicating the steps for characterizing the humeral head prosthesis features as described in the Examples.

Referring again to the drawings, FIG. 3 provides additional details relative to the anatomically relevant markers that were identified in the sample of humerii for providing the parameters and formulae as described herein for elliptical non-spherical humeral head prostheses. FIG. 3 shows in its upper panel anthropometric measurements: AX, long axis of the humerus; CD, critical distance; CP, critical point; COR, center of rotation; DAM, distal articular midpoint; DF, diameter of the base of the humeral head in the frontal plane; DS, diameter of the base of the humeral head in the sagittal plane; HHH, humeral head height; IA, inclination angle; MO, medial offset; PO, posterior offset; SA, surface arc.

In short, as shown in the lower panel in FIG. 3, the method of marking simulated radiographs for anthropometric measurement is achieved with reference to the anatomical features as shown in the illustrations of FIG. 3, whereby (A) To obtain the ideal view for the simulated anterior-posterior radiographs, the humeral head model is oriented so that DF is parallel to while DS is perpendicular to the computer screen. (B) A custom-made ruler with a center slot is used to mark the long axis of the humerus in the frontal plane. (C) Custom-made circular templates that increase in size in 1-mm increments are used to identify the center of rotation and to size the radius of curvature in the frontal plane. (D) Additional lines are added as shown. (E) To obtain the ideal view for the simulated medial-lateral radiographs, the humeral head model is oriented so that DS is parallel to while DF is perpendicular to the computer screen. (F) A custom-made ruler with a center slot is used to mark the long axis of the humerus in the sagittal plane. (G) Custom-made circular templates that increase in size in 1-mm increments are used to identify the center of rotation and to size the radius of curvature in the sagittal plane. (H) Final markup for the simulated medial-lateral radiographs.

Figure 4:
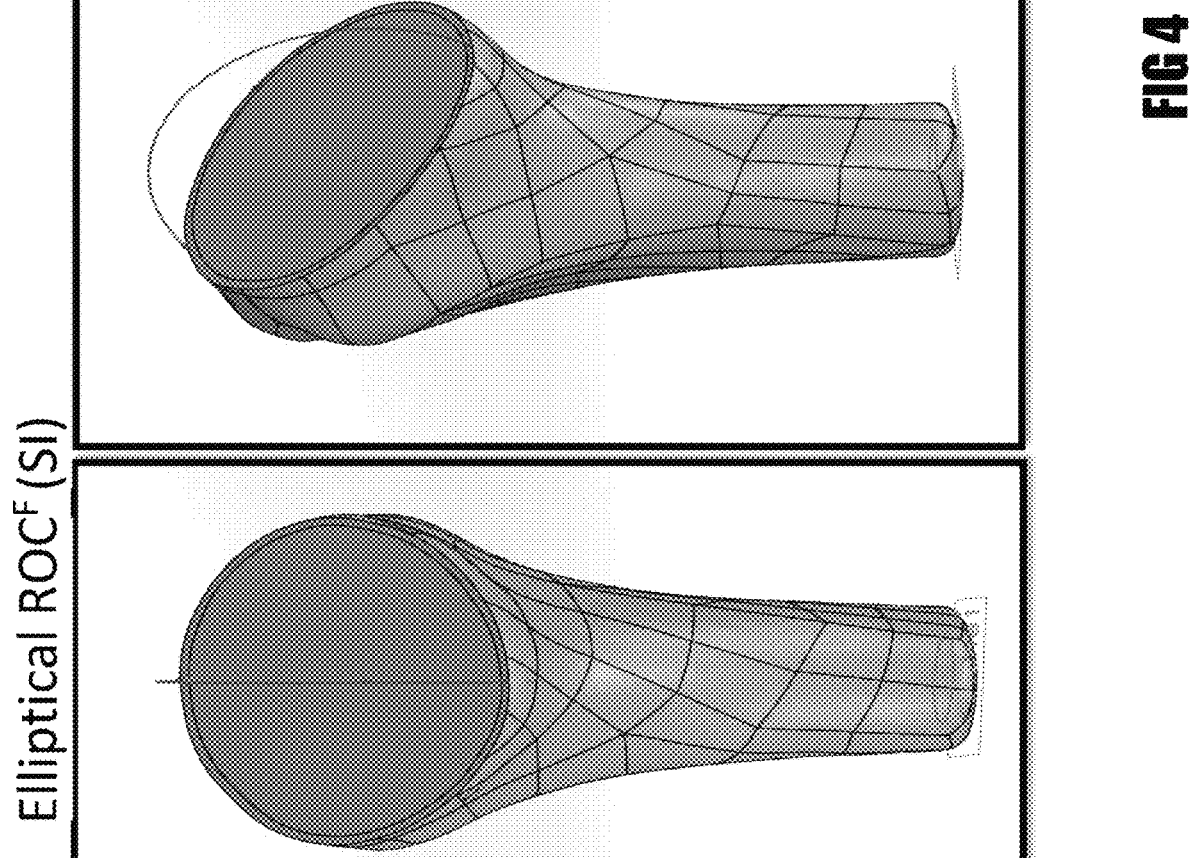
FIG. 4 shows alternate views of a cut humerus indicating the radius of curvature in the frontal plane (SI)
Figure 5:
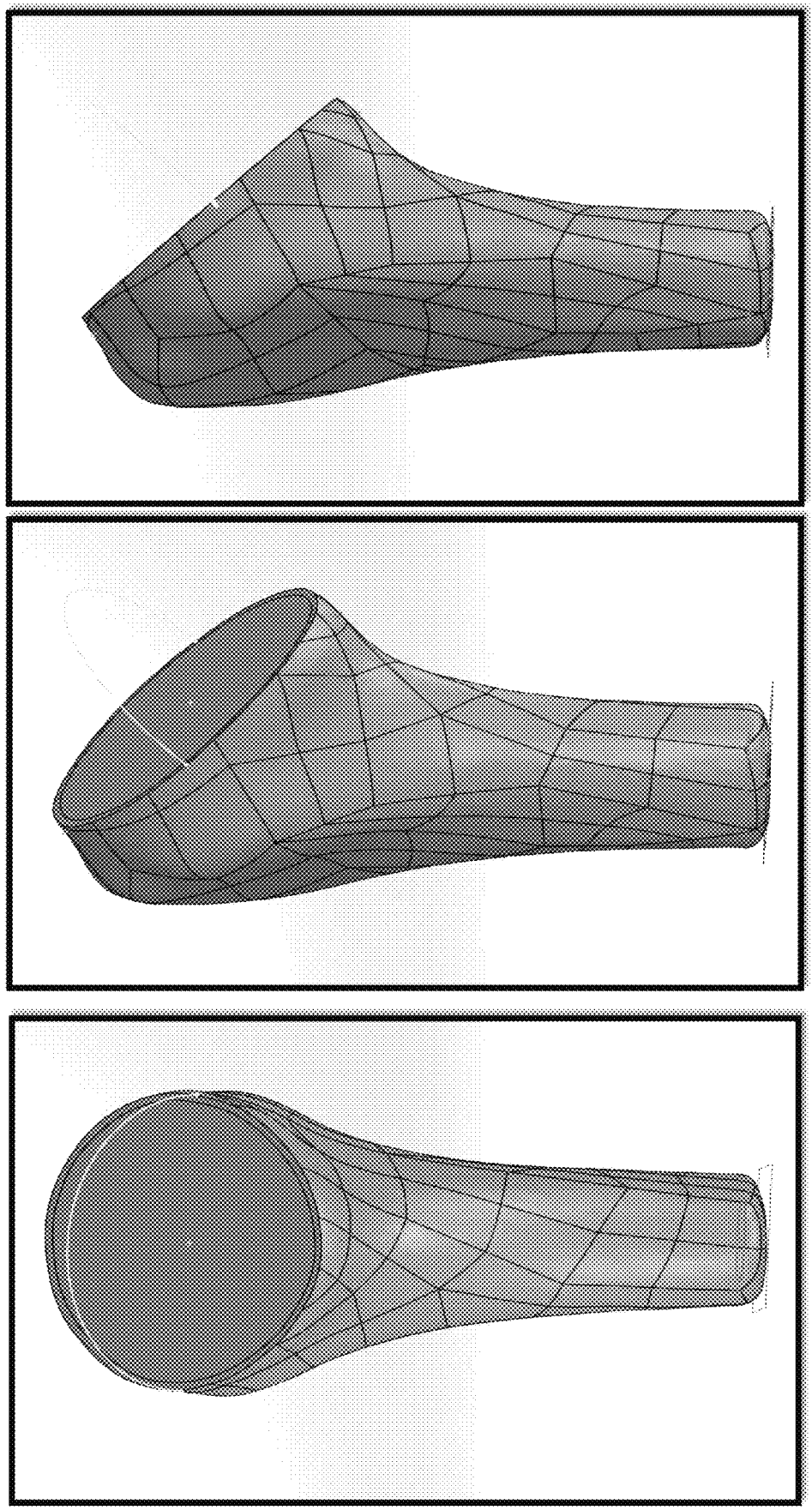
FIG. 5 shows alternate views of a cut humerus indicating the radius of curvature in the sagittal plane (AP)
Figure 6:
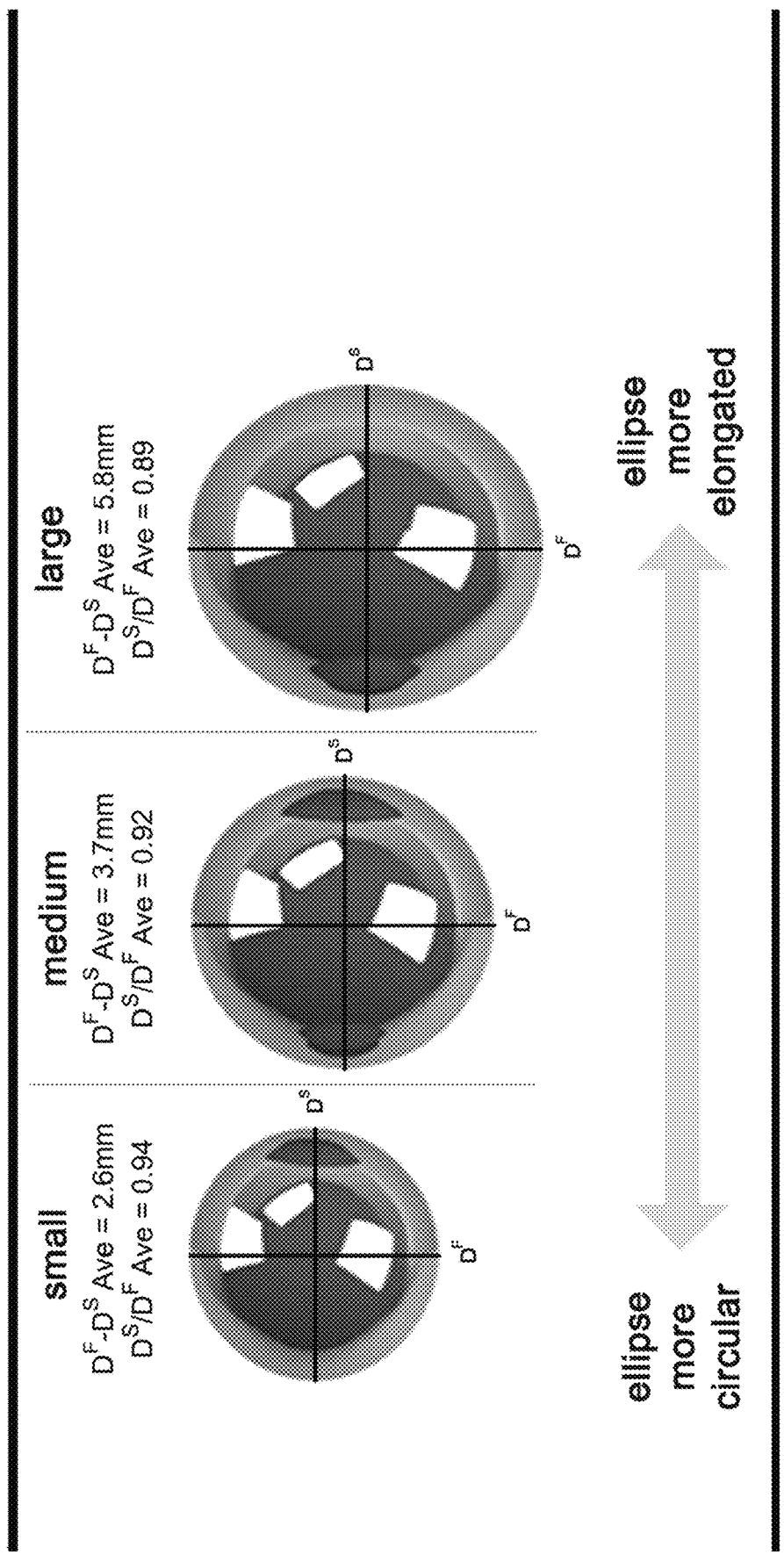
FIG. 6 is a diagram showing variation of the diameter in the frontal plane as humeral size increases.
Figure 7:
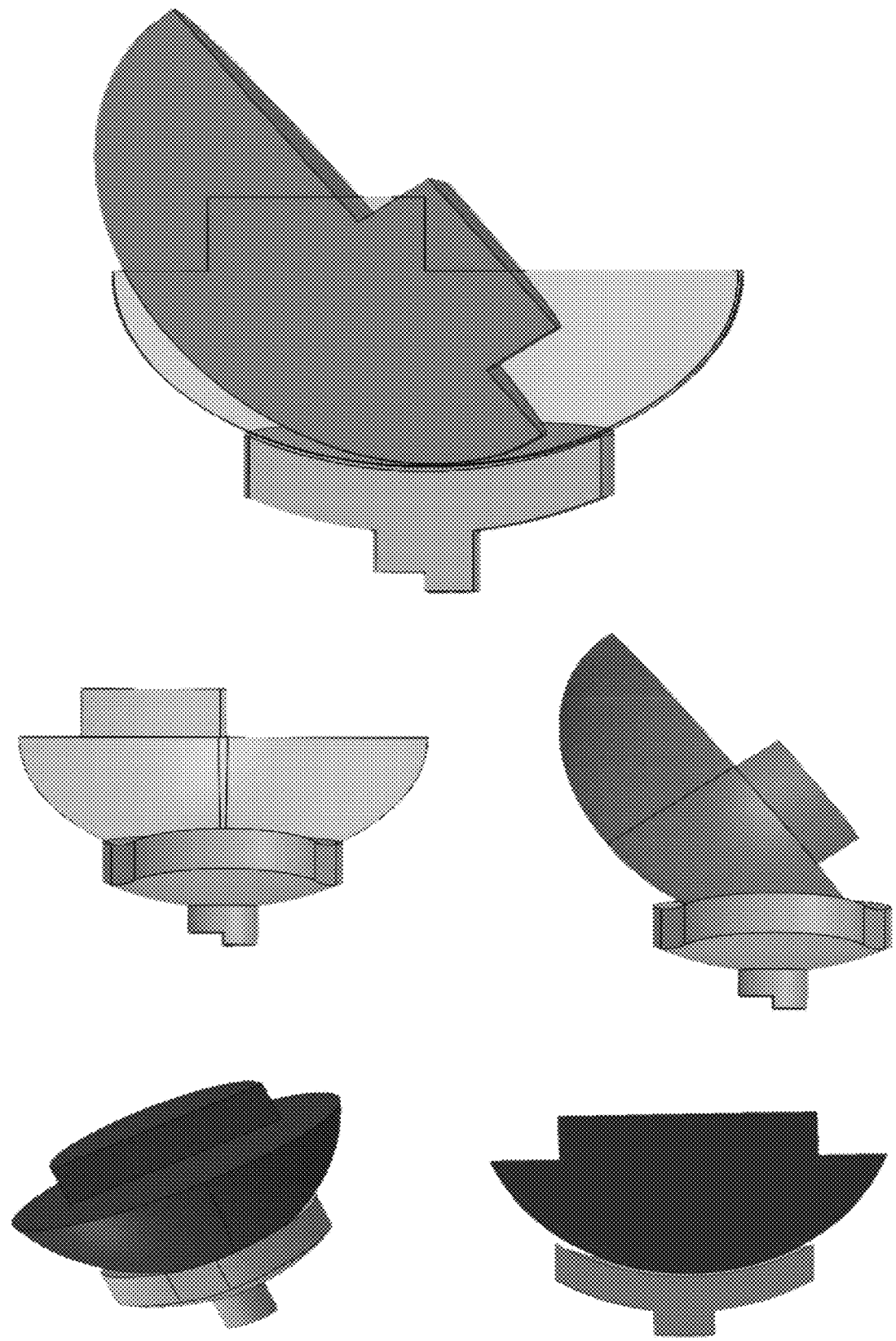
FIG. 7 shows alternate views of the articulation of a spherical vs. an elliptical humeral head prosthesis relative to a glenoid.
Figure 8:
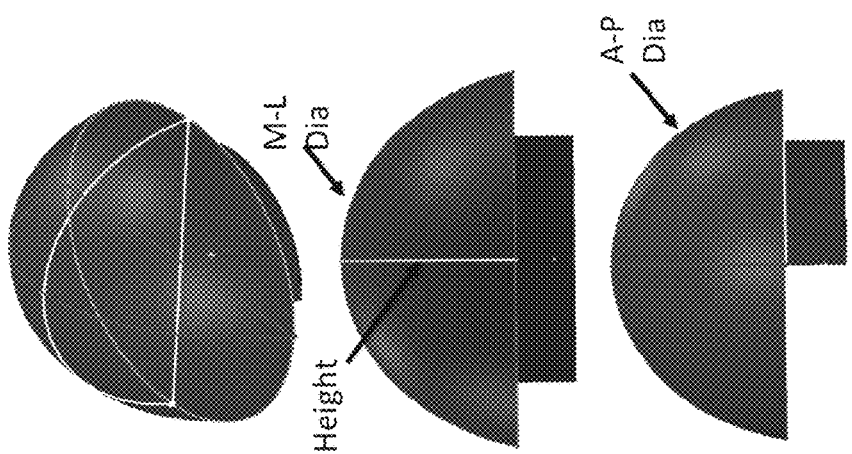
FIG. 8 shows side and perspective views of a spherical humeral head prosthesis and a elliptical humeral head prosthesis indicating the frontal and sagittal diameters and radii of curvature.
Figure 8:
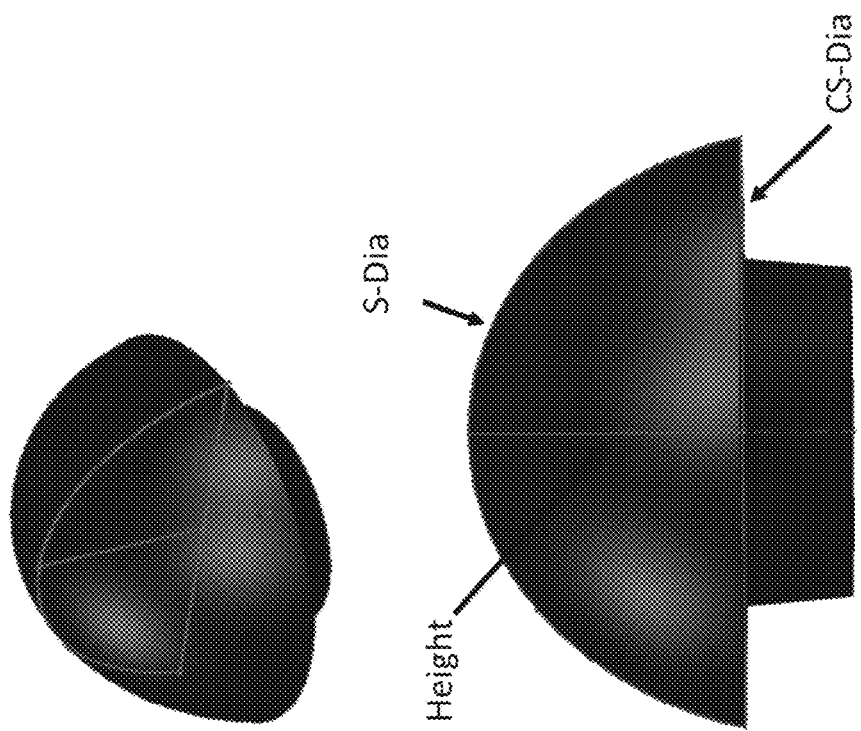
Figure 10:
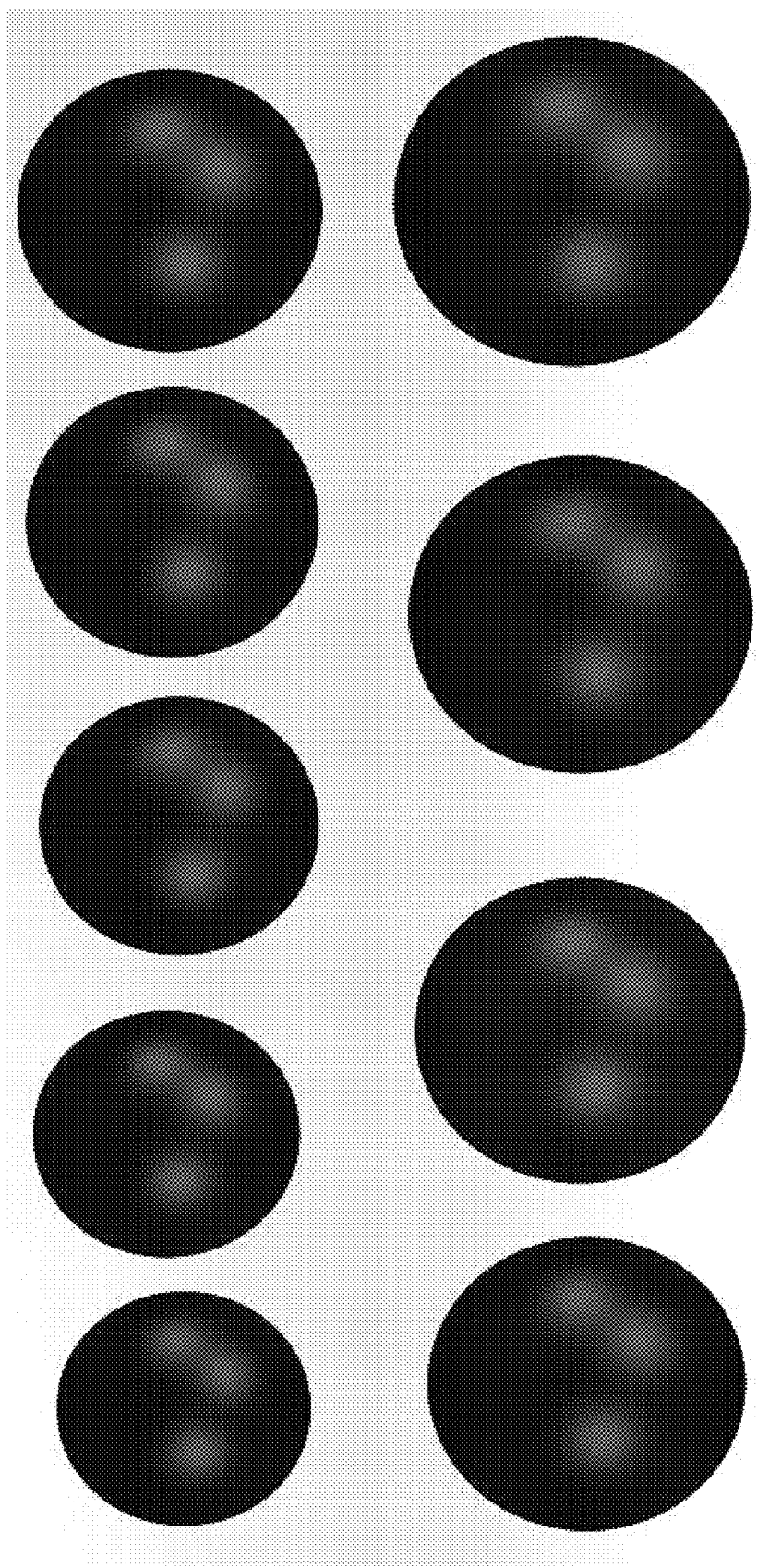
FIG. 10 shows a representative array of generally spherical shaped humeral head prostheses.
Figure 15:
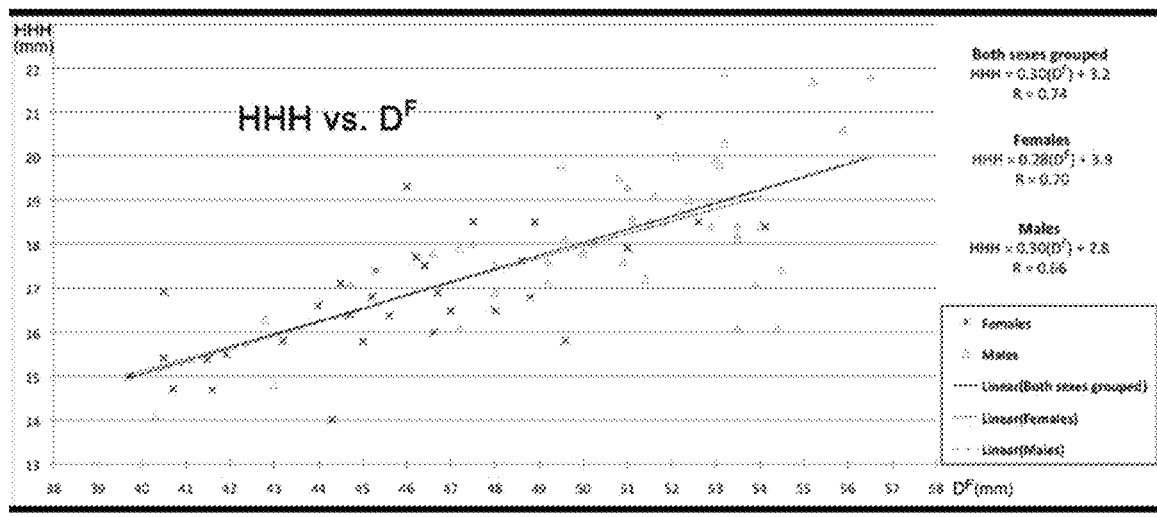
FIG. 15 shows scatter plots with linear trend lines demonstrating in the upper panel graphic the mathematical relationship between the humeral head prosthesis height (HHH) and the diameter of the base of the head in the frontal plane (DF), and in the middle panel graphic the mathematical relationship of the radius of curvature in the sagittal plane ($ROC^S$) vs. DF, and in the lower panel graphic the mathematical relationship of the radius of curvature in the frontal plane ($ROC^F$) vs. DF.
Figure 15:
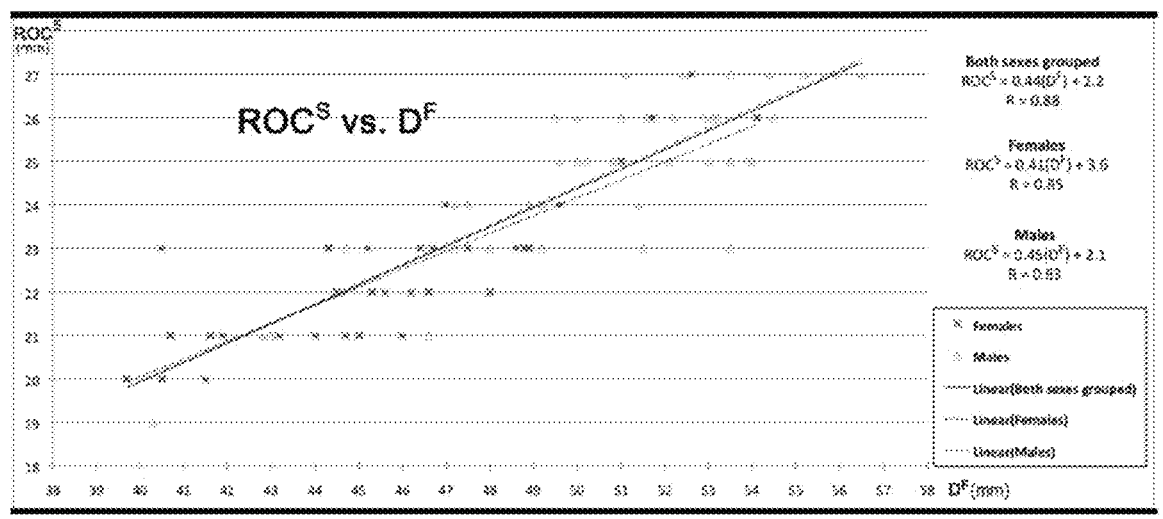
Figure 15:
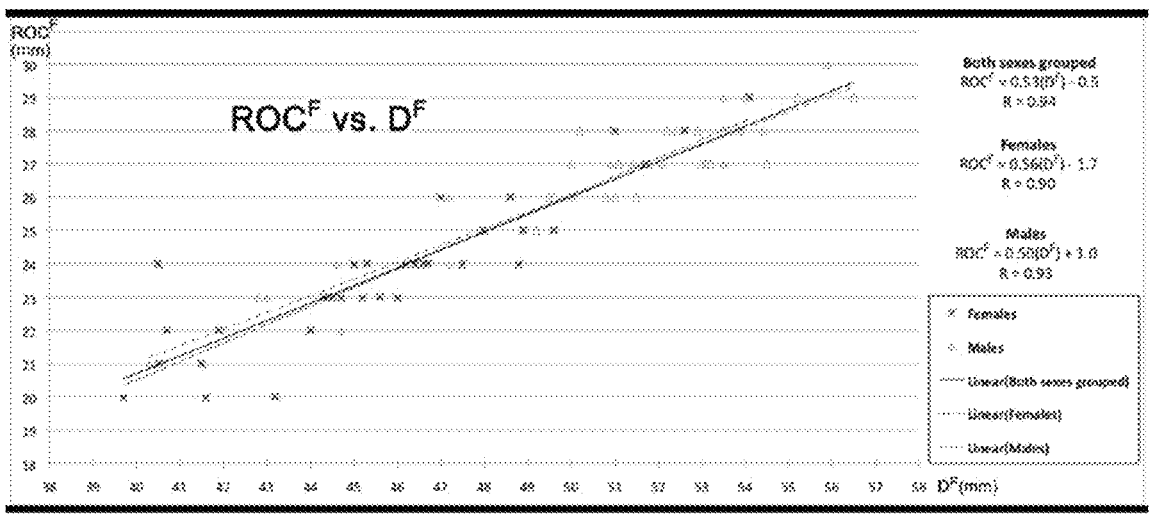

Referring again to the drawings, FIG. 4 and FIG. 5, respectively, show the radii of curvature in each of the frontal (SI) and sagittal planes (AP) relative to the bone cut on a humeral head model, corresponding to the approximate location of the humeral head. As further described herein in the Examples, the inventors made the surprising discovery that in a population of individuals, the overall shape and relative proportions of the diameter in each of the frontal and the sagittal planes changes as the overall size increases. As described herein, there are reports in the art that the relative difference between the DF and DS may be typically about 2 mm and up to 4 mm in the context of elliptical humeral heads, which has been treated in the art as a constant variation even as head size increases. What has not been known or suggested in the art heretofore is that this difference between DF and DS is not a constant but varies as head size increases. FIG. 2 and FIG. 6 provide details and formulae for the relationships of the features of DF, DS, and HHH and the radii of curvature in the frontal and sagittal planes as size increases overall. Further details are shown in FIG. 13-FIG. 15, which show various scatter plots with linear trend lines demonstrating the mathematical relationship between the length difference between the humeral head axes in the frontal and sagittal planes (DF−DS) and the diameter of the base of the humeral head in the frontal plane (DF), and other features of native humeral head anatomy, which data are further illuminated in the Examples. Thus, as shown in FIG. 6, it is possible to described a novel array of elliptical humeral heads based on these surprising findings, wherein as the size increases, the humeral heads change from more circular in cross section to more elliptical (elongate) and the differences between and the ratios of the major (frontal/SI) diameter (DF) and minor (sagittal/AP) diameter (DF) change rather than remain constant.

Referring now to FIG. 7-FIG. 11, the drawings show various aspects of humeral heads prosthesis that illustrate the differences between arrays of spherical humeral heads and elliptical humeral heads wherein the measurement DF−DS and the ratio of DS/DF vary as DF increases. In accordance with the various embodiments, the shape of the humeral head prosthesis is generally elliptical (i.e. non-spherical), allowing an enhanced selection to achieve anatomical matching between the removed native humeral head and the prosthesis. In accordance with the disclosure, use of humeral heads that have a non circular elliptical cross section are particularly desirable for providing the widest array of options to replicate native anatomy and to avoid functional problems for the patient with the arthroplasty.

As described further herein below, use of such humeral heads that have a non circular elliptical cross section, and in some embodiments used together with a novel metaphyseal shell coupler component, enables the surgeon to accommodate one or more of offsets in positioning from the sagittal/AP and frontal/SI planes, but also rotational positioning of the humeral heads that have a non circular elliptical cross section to achieve the most desirable replacement anatomy. Thus, it will be evident from the drawings showing a spherical humeral head as compared to those with an elliptical humeral head that a spherical humeral head that is selected for suitable fit in the DS direction would be undersized in the DF direction (frontal plane), and that a spherical humeral head that is selected for suitable fit in the DF direction would be oversized in the DS direction (sagittal plane), which arrangement could cause rotator cuff tearing and joint stiffness.

In the various embodiments, humeral head prostheses have dimensions that are suited to allow a range of custom fits to best match a subject's anatomy. As such, humeral heads vary in terms of shape (from more round to elliptical), height (distance from the engagement surface to the apex), and peripheral dimension (circumference for round heads and DS to DF dimensions for elliptical heads). In accordance with what is known in the art, the overall shape of the humeral heads at the apex is generally spherical, though the scope of the invention includes use of humeral heads that may have another shape that is not spherical. In the case of elliptical heads herein, it is contemplated that such humeral heads having spherical apexes would present a glenoid articulation surface that is spherical and would taper along the DF dimensions to the periphery along a generally elliptical arc ($ROC^F$). And in some further embodiments, the head would taper along the DS dimension along a generally elliptical arc ($ROC^S$).

As described herein, the DF and DS dimensions of a humeral head according to the disclosure are in reference to a cross sectional plane of a humerus essentially in the DS plane with an inclination angle off that plane from about 120 to 145 degrees, and in some embodiments from 120 to 143, and in certain disclosed embodiments herein, of about 135 degrees. The cut corresponds to the anatomical neck of the humerus see URL (//en.wikipedia.org/wiki/Anatomical-_neck_of_humerus).

In accordance with the various embodiments, the humeral head prosthesis may be provided for implantation at an angle of inclination from and including angle increments in between 120, 121, 122, 123, 124, 125, 126, 127, 128, 129, 130, 131, 132, 133, 134, 135, 136, 137, 138, 139, 140, 141, 142, 143, 144, and 145. Thus, in accordance with the disclosure, in various embodiments, stems and other arthroplasty components are provided for engagement with a humeral head prosthesis having an inclination that is about 135 degrees, or otherwise as provided herein. It will be apparent to one of ordinary skill in the art that the stems could be provided having a different angle of inclination, and that the ultimate angle of inclination of an implant is determined based on the angle selected by the surgeon when selecting the prosthesis components to provide an optimally anatomical match to the patient.

Figure 11:
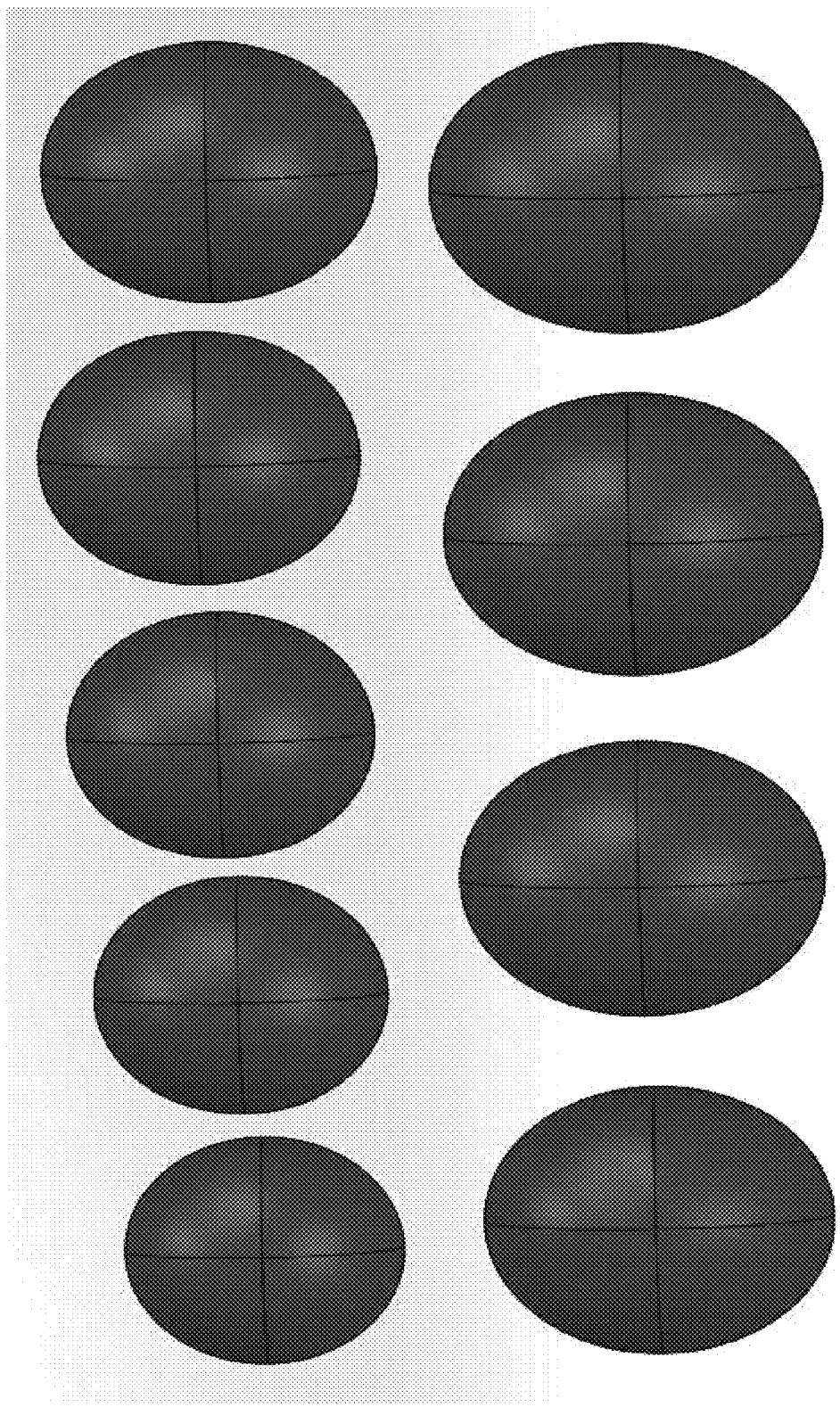
FIG. 11 shows a representative array of generally non-spherical elliptical shaped humeral head prostheses.
Figure 12:
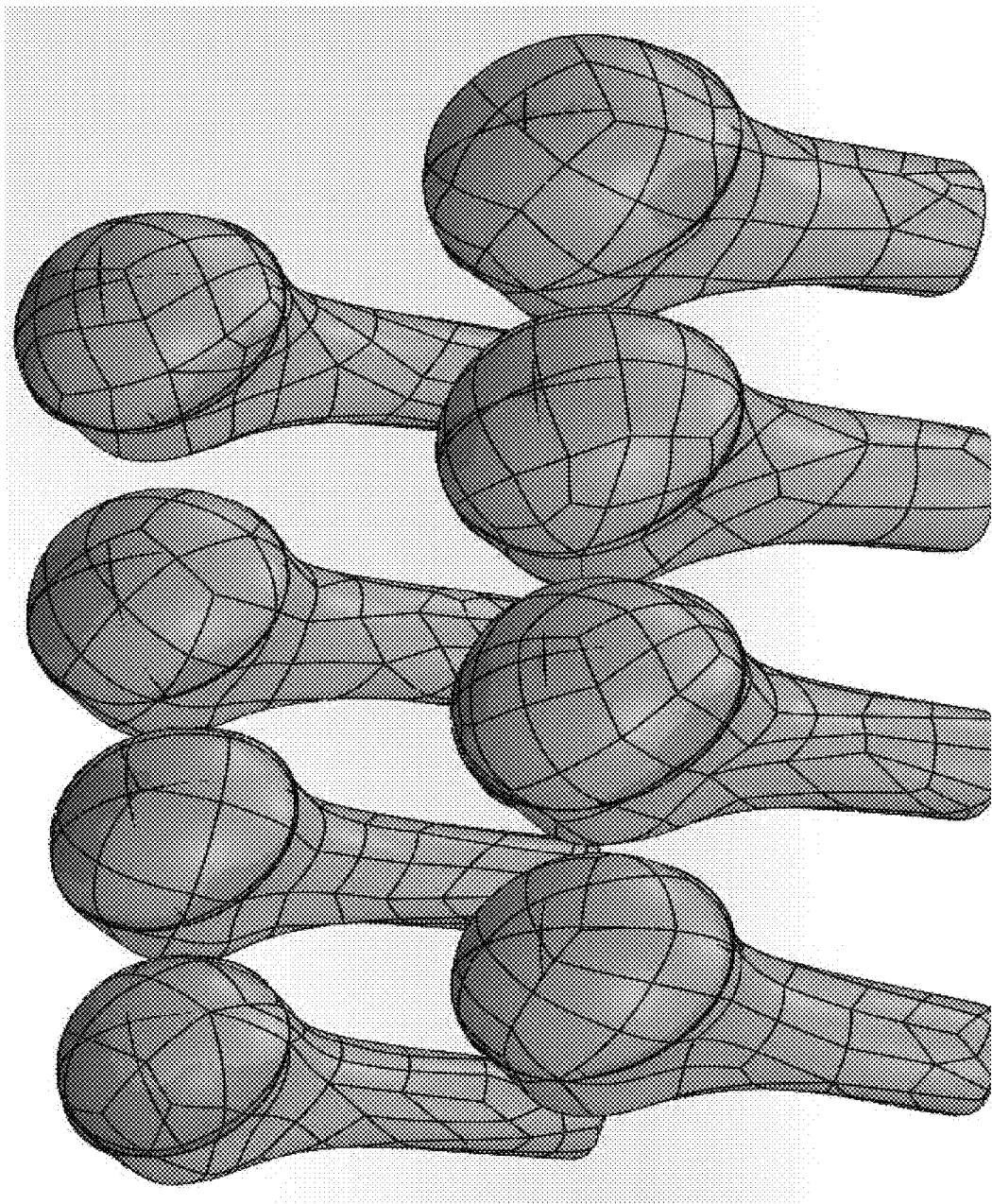
FIG. 12 shows a representative array of generally non-spherical elliptical shaped humeral head prostheses in the context of a humerus.

Referring again to the drawings, FIG. 11 and FIG. 12 shows an exemplary array of elliptical heads that vary in size as follows relative to a bone cut on the DS plane. FIG. 9 shows a representative example of the size and other features of an embodiment of an array of humeral heads according to the disclosure. More generally, arrays herein can be described as follows, where each prosthesis in the array have diameter dimensions that range from 30 mm to 62 mm in the superior to inferior dimension (DF), and range from 30 to 58 mm in the anterior to posterior dimension (DS). In some particular embodiments, the DF range is from 37 to 56 mm and the DS range is from 36 to 51 mm. In yet other embodiments, the DF range can encompass from 20 to 80 mm, and can include sizes in the DF dimension from and including the following and increments in between: 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 mm. Likewise, in such other embodiments, the DS range can encompass from 20 to 80 mm, and can include sizes in the DS dimension from and including the following and increments in between: 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 mm. Selection of the specific size based on DF and or DS will be made in accordance with the skill in the art and with particular reference to the size and population features of the subject in accordance with the teachings herein. Thus, the arrays and the discrete prostheses will have elliptical head properties in accordance with one or more of the formulae and DS to DF relationships as described herein.

In one representative embodiment of an array of elliptical heads, included humeral head sizes that may encompass the following array, wherein the DS dimension ranges from 36 to 51 mm, the DF dimension ranges from 37-56 mm, the ratio of DS/DF ranges from 0.87 to 1, and wherein the angle of inclination ranges from 120 degrees to 143 degrees. Specific humeral heads within the array are provided in sizes having humeral head heights ranging from 12 to 25 mm, and in representative embodiments from 14 to 21 mm, and in certain specific embodiments in increments there between.

The relationship between the DF to DS dimensions in one embodiment of elliptical heads is 1 (spherical heads). In some embodiments according to the disclosure, the DF to DS dimensions are related in a range where the DF dimension is about 2 mm larger than the DS dimension regardless of head size. In alternate embodiments, the variation between the DF and DS dimensions may vary from 0.5 mm to 10 mm or more, and thus can include variation in mm and increments in between including 0.5, 1, 2, 3, 4, 5, 6, 7, 8, 9, 10 mm. In yet another alternate embodiment, the DF to DS dimensions are related in a range where the DS/DF ratio changes from 1 to 0.85 as the head size and DF increases. Generally, according to such embodiments where the DS/DF ratio changes, the range can include from 0.5, 0.6, 0.7, 0.8, 0.9, 1, 1.5, and 2 and incremental fractions there between.

Figure 16:
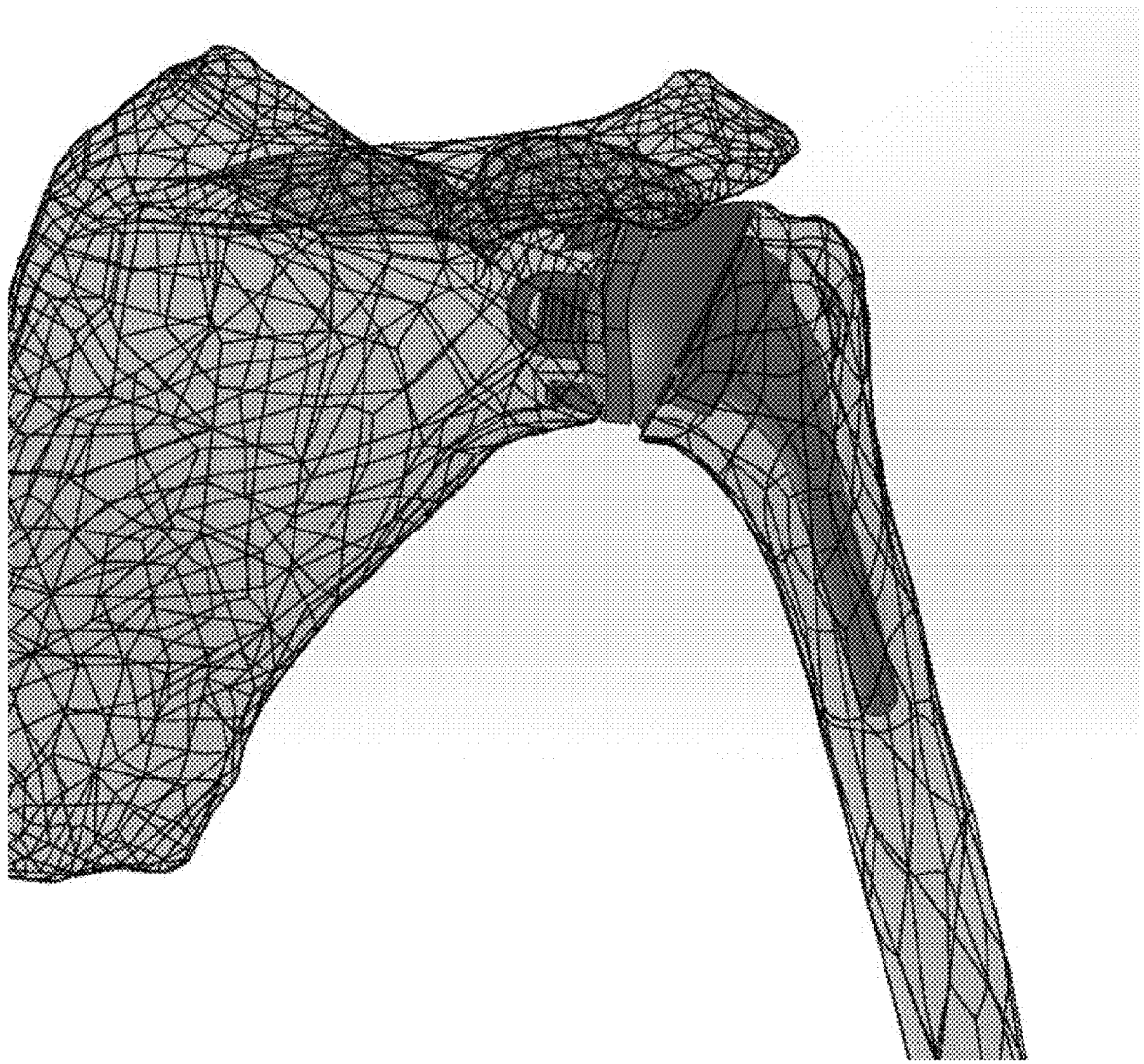
FIG. 16 shows a side view of an embodiment of a modular arthroplasty assembly with a metaphyseal shell, stem and head prosthesis, assembled in the context of shoulder bone.

In some embodiments, the elliptical humeral heads may be used together with a tray or metaphyseal shell coupler that is engageable with an elliptical humeral head prosthesis component according to the disclosures to provide an arthroplasty assembly. Referring again to the drawings, FIG. 16 shows a side view of an embodiment of a modular arthroplasty assembly with a coupler component that enables variable positioning relative to the long axis of the bone and including a stem and a prosthesis component, assembled in the context of a shoulder bone. Using the coupler of the modular system, the position of the prosthesis component can be varied rotationally around a shared central engagement axis with the coupler component to allow for selection of the optimal anatomical positioning of the elliptical humeral head. The position of the anchor component relative to the coupler component can be varied in two dimensions on a plane that is perpendicular to the central engagement axis of the coupler and prosthesis components by selecting the coupler component from an array comprising a plurality of coupler components that include variably positioned anchor engagement features.

In accordance with the invention, each of at least two of the plurality of coupler components comprises at least one anchor engagement feature that is off-center from a center point of the coupler component, and the off-center engagement feature on each of the at least two coupler components is at a different distance in at least one dimension that is perpendicular to the central engagement axis. In use, when the coupler and anchor components are recessed into bone, the assembly achieves alignment of the bone articulation surface of the prosthesis component with the bone that is anatomically similar to a native long bone.

Thus, in some embodiments, a modular arthroplasty assembly includes (a) an convertible offset coupler (alternately a "metaphyseal shell") bounded on a first side by an implant surface adapted to receive an implant component, and bounded on an opposite second side by a bone anchor engagement surface, (b) an elliptical non spherical humeral head prosthesis component, and (c) a bone anchor configured to be inserted in bone and adapted for engagement with the convertible offset coupler.

In various embodiments, the modular arthroplasty assembly includes (a) an convertible offset coupler (also referred to herein as a "coupler component" and alternately a "metaphyseal shell") bounded on a first side by an implant surface adapted to receive an implant component, and bounded on an opposite second side by a bone anchor engagement surface, (b) an prosthesis component selected from one of a humeral head selected form the elliptical non-spherical humeral head prostheses according to the disclosure, and in some embodiments, a cupped reverse prosthesis (also referred to herein as a "prosthesis component" and alternately "head" and "cup," respectively), and (c) a bone anchor configured to be inserted in bone and adapted for engagement with the convertible offset coupler (also referred to herein as a "anchor component" and alternately "stem" or "plug"). As shown in FIG. 16, the implant component is a spherical shaped humeral head. It will be appreciated that the prosthesis component may be a humeral head that is one of spherical and non-spherical. In use, the concentric coupling feature on the humeral head prostheses provides a superior solution for use of elliptical heads to achieve an optimized anatomical match and is a key aspect of the novel system disclosed herein to allow anatomical matching for up to 97% of patients (based on the study data reported in the Examples herein). Rotational orientation occurs at the humeral head prosthesis-metaphyseal shell engagement interface, while offset occurs at the metaphyseal shell/anchor engagement interface. Selection from the arrays of heads, shells and anchors, as further described herein below, and surgeon selected orientation of the rotational positon of the elliptical articulation surface, followed by final fixation of the assembly, allows creation of a near match to the patient's native anatomy. Moreover, because of the modularity of the components, any surgical revision that may be necessitated can be more easily achieved than is currently possible in the art by use of the metaphyseal shell, which allows positional adjustment, replacement, removal and replacement of the head with a cup to achieve a reverse arthroplasty, all without the need for complete removal of the shell/anchor implant from the humerus.

In various embodiments, the overall shape of the metaphyseal shell is generally cylindrical, with an outer surface and dimensions that are adapted for insertion at least partially within humeral bone and is bounded on a first side by an implant surface adapted to receive an implant component, and on an opposite second side by a bone anchor engagement surface. In some embodiments, the metaphyseal shell is adapted with at least or one another of a male insert and a female receiver channel (such as a Morse type taper), on one or both opposing sides, and optionally adapted to receive one or more of a pin or setscrew or other fastener to achieve engagement with at least one of the prosthesis component and the bone anchor. In some embodiments, the metaphyseal shell bears on a lateral peripheral edge a surface feature that is adapted to enhancing boney ingrowth.

Accordingly, in some embodiments, all or a portion of the outer surface of the metaphyseal shell may be adapted with surface texturing to encourage bone ingrowth or ongrowth. In addition, the stem engagement surface may be adapted with surface texturing to enhance engagement therebetween. In various embodiments, the metaphyseal shell includes at least one engagement feature that allows engagement and fixation with each of the humeral head and cup prostheses.

Figure 17:
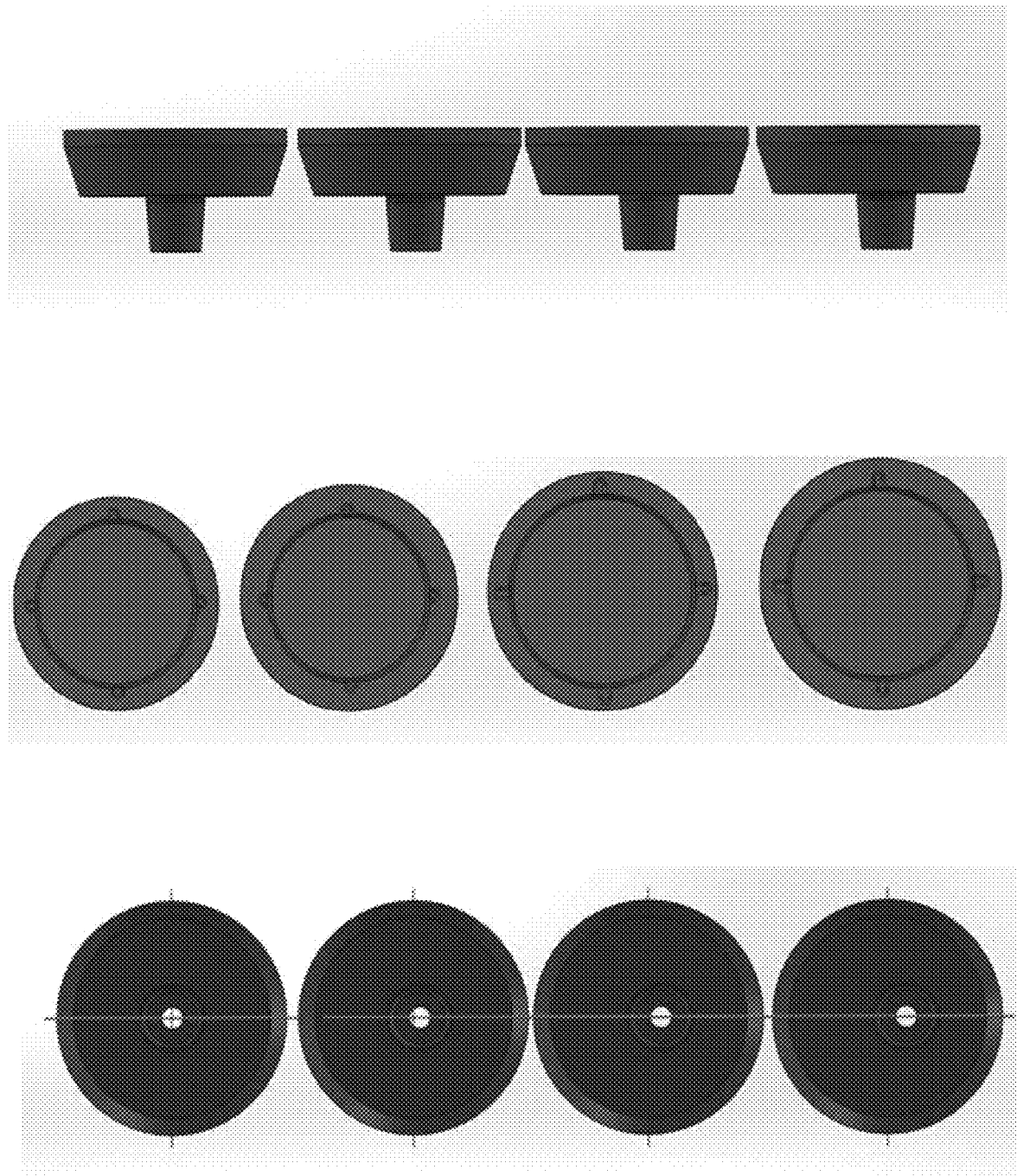
FIG. 17 shows an exemplary array of a metaphyseal shell according to the disclosure.
Figure 18:
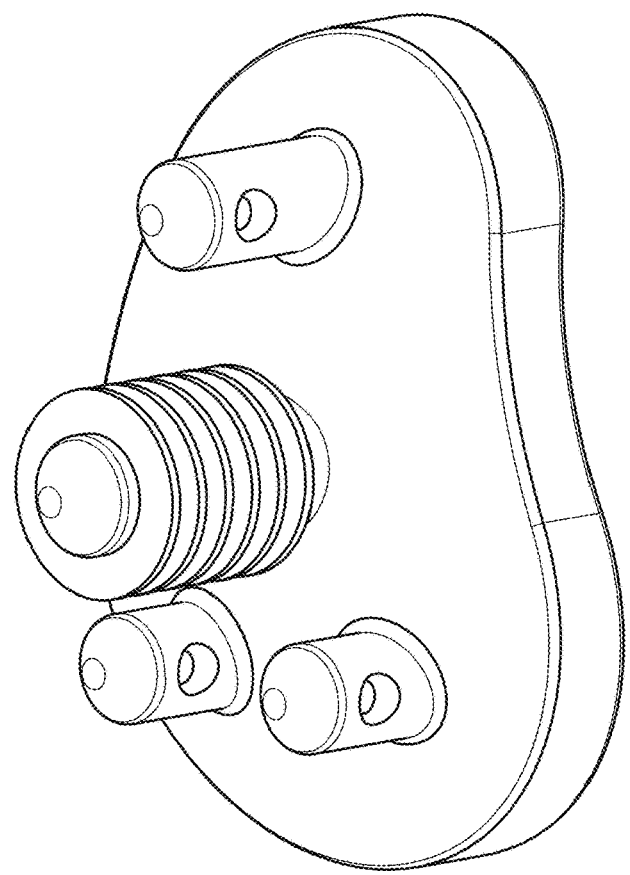
FIG. 18 is a perspective view of an embodiment of a keeled glenoid.
Figure 19:
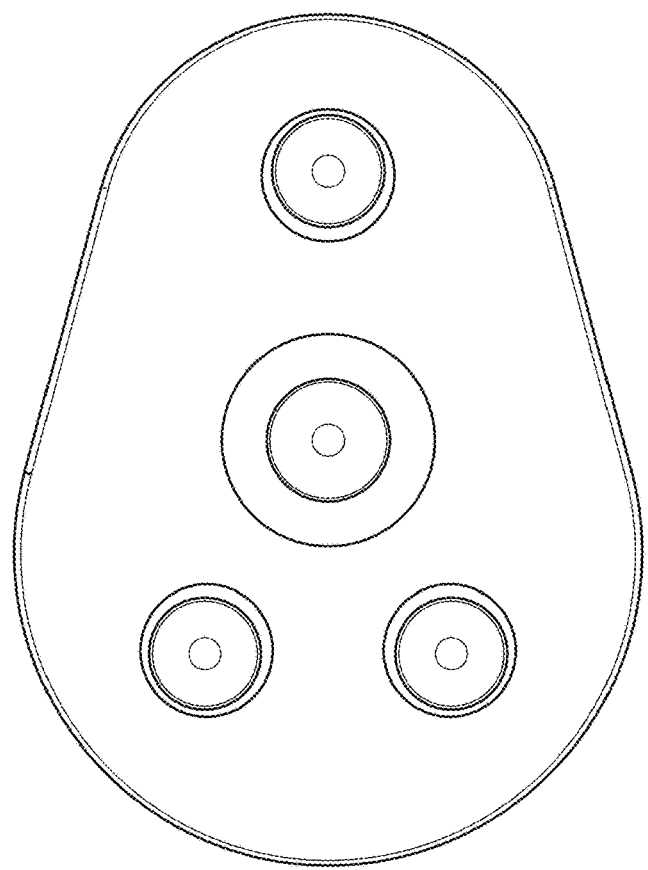
FIG. 19 is a top plan view of the keeled glenoid of FIG. 18.
Figure 20:
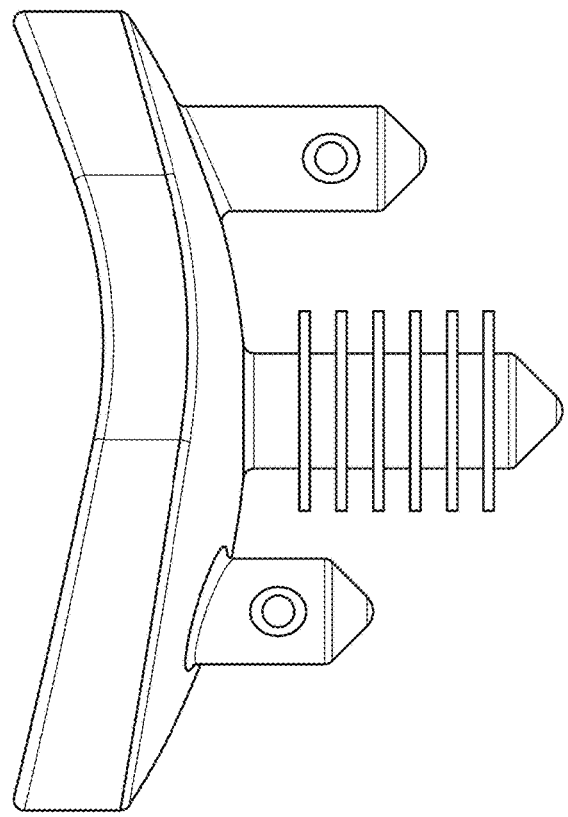
FIG. 20 is a side elevation view of the keeled glenoid of FIG. 18.
Figure 21:
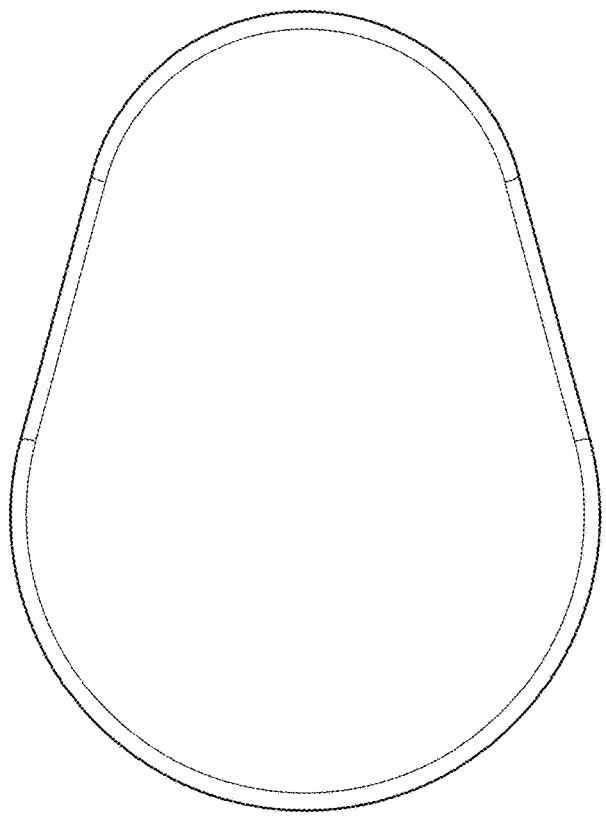
FIG. 21 is a bottom plan view of the keeled glenoid of FIG. 18.
Figure 22:
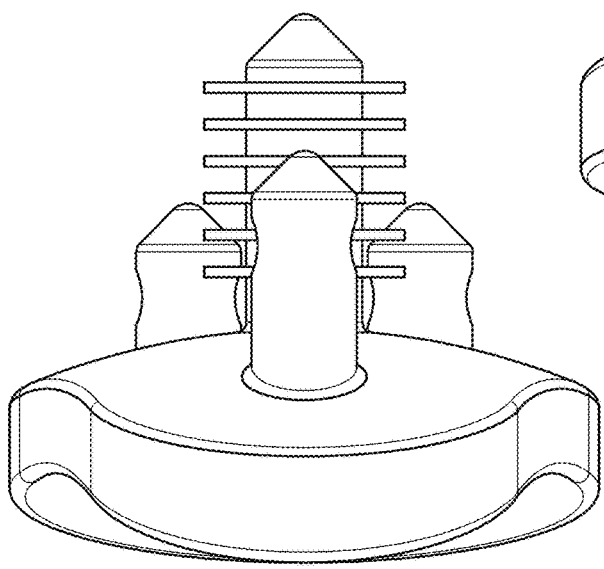
FIG. 22 is a front elevation view of the keeled glenoid of FIG. 18.
Figure 23:
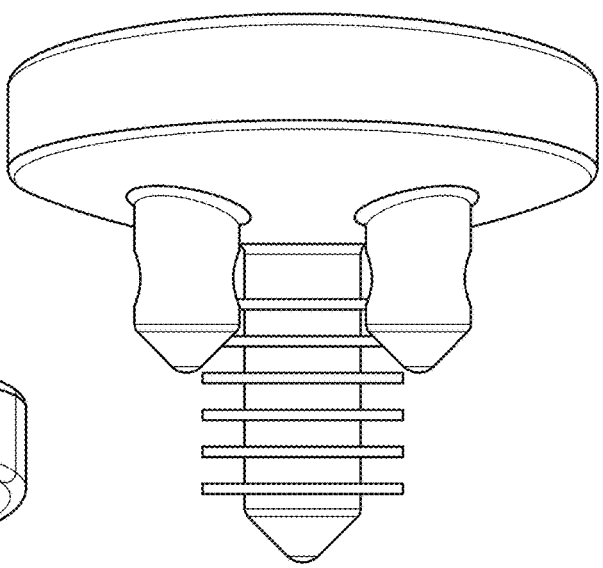
FIG. 23 is a back elevation view of the keeled glenoid of FIG. 18.
Figure 24:
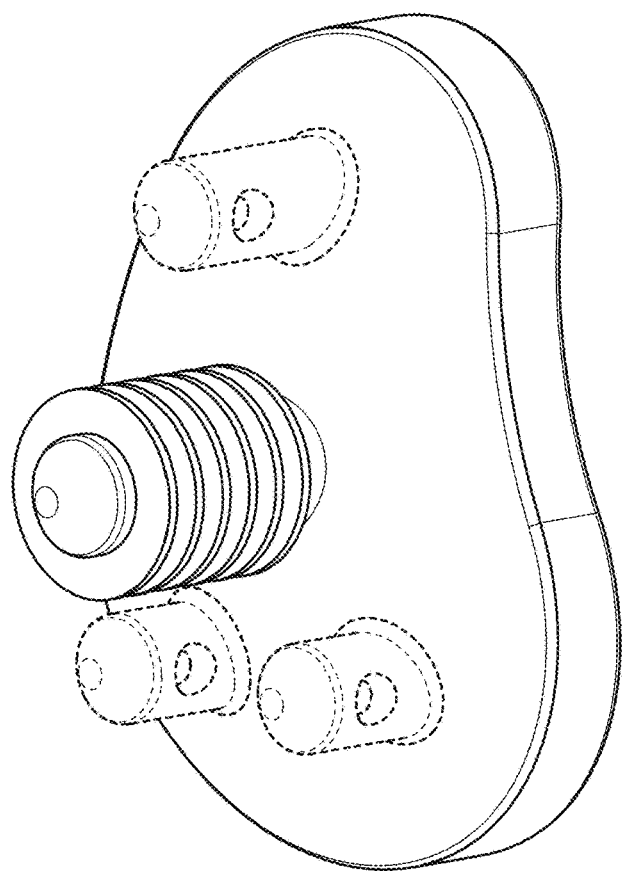
FIG. 24 is a perspective view of an alternate embodiment of a keeled glenoid of FIG. 18.
Figure 25:
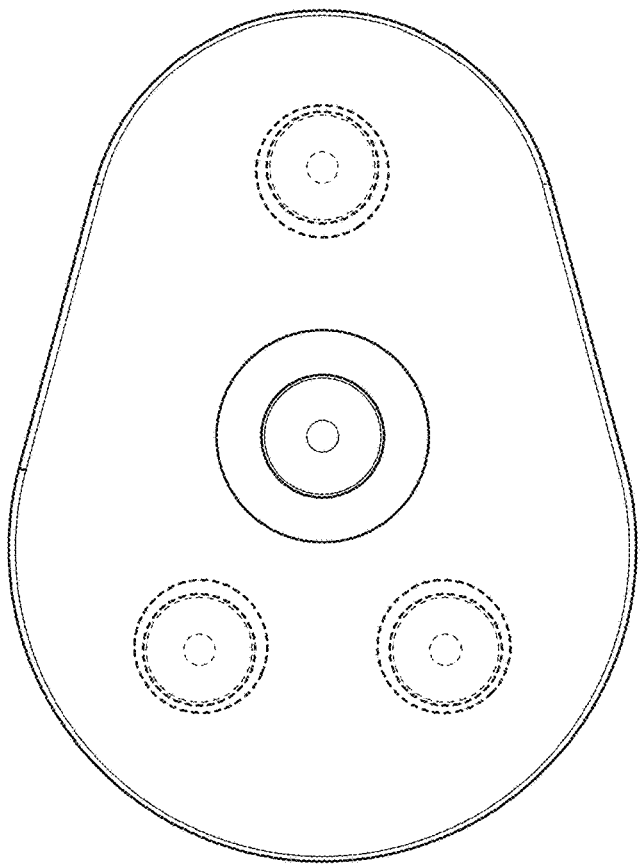
FIG. 25 is a top plan view of the keeled glenoid of FIG. 24.
Figure 26:
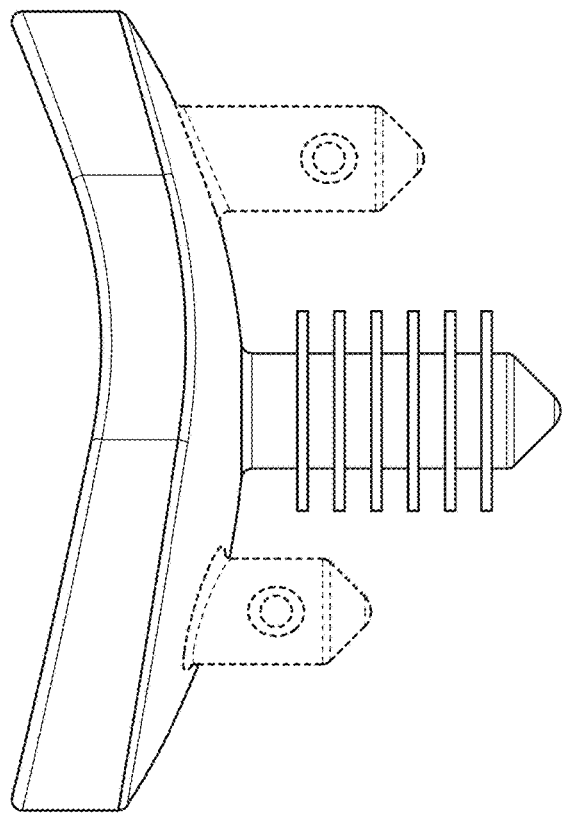
FIG. 26 is a side elevation view of the keeled glenoid of FIG. 24.
Figure 27:
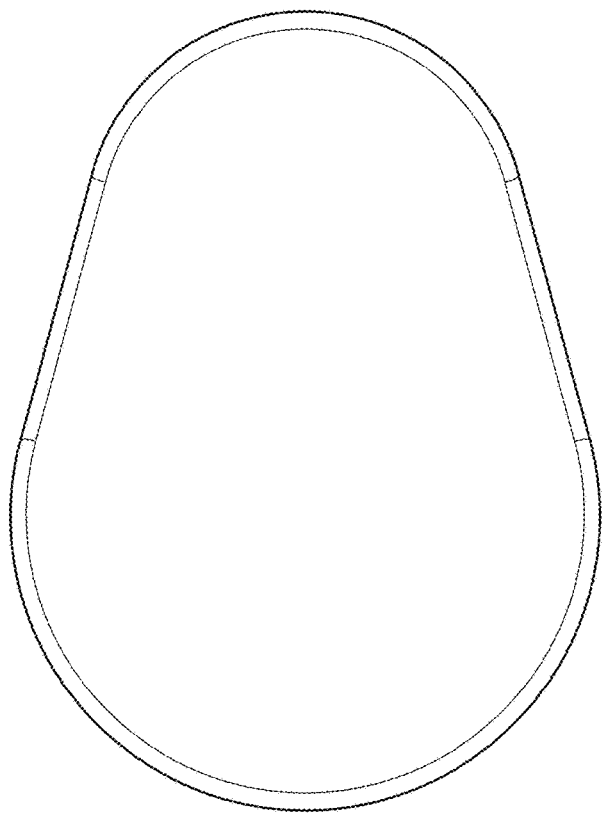
FIG. 27 is a bottom plan view of the keeled glenoid of FIG. 24.
Figure 28:
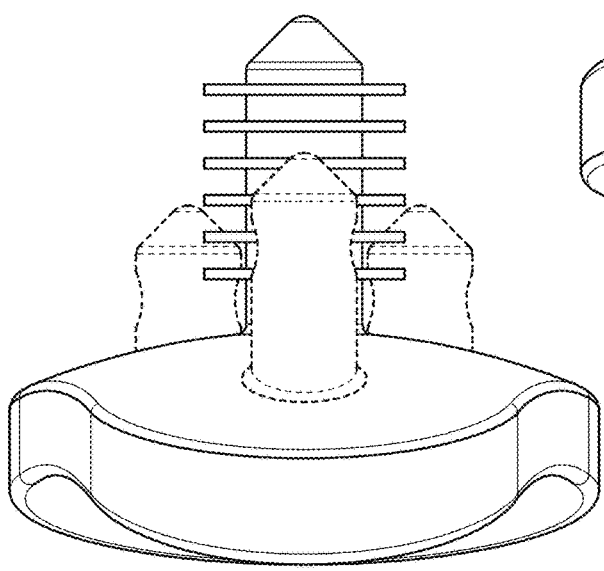
FIG. 28 is a front elevation view of the keeled glenoid of FIG. 24.
Figure 29:
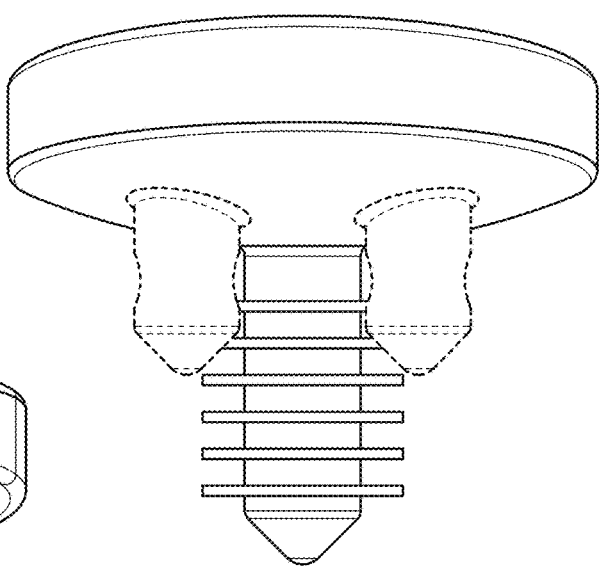
FIG. 29 is a back elevation view of the keeled glenoid of FIG. 24.
Figure 30:
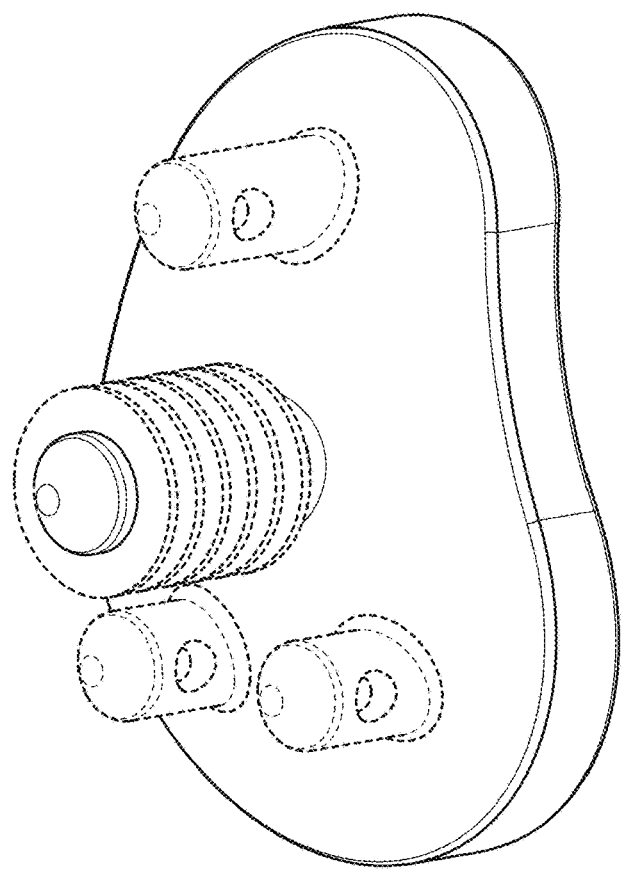
FIG. 30 is a perspective view of an alternate embodiment of a keeled glenoid of FIG. 18.
Figure 31:
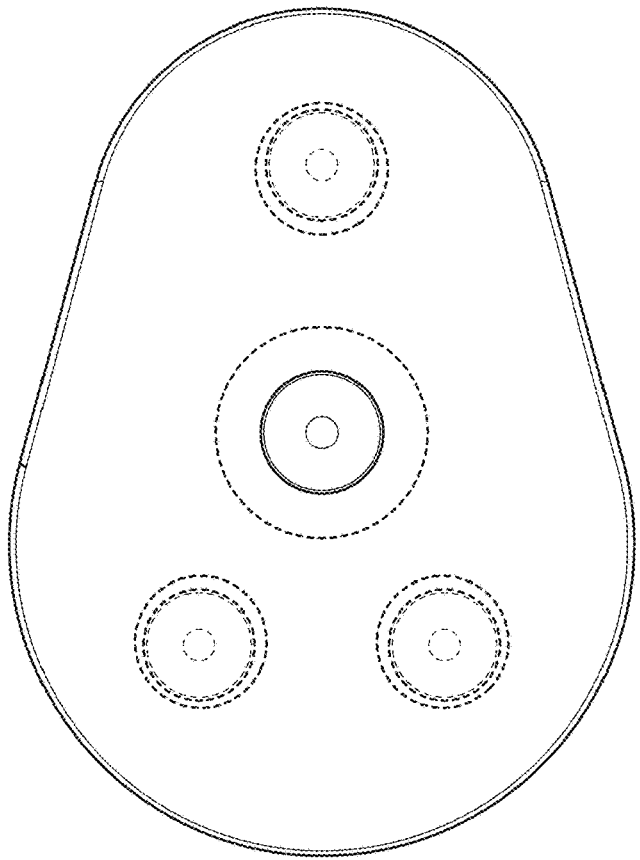
FIG. 31 is a top plan view of the keeled glenoid of FIG. 30.
Figure 32:
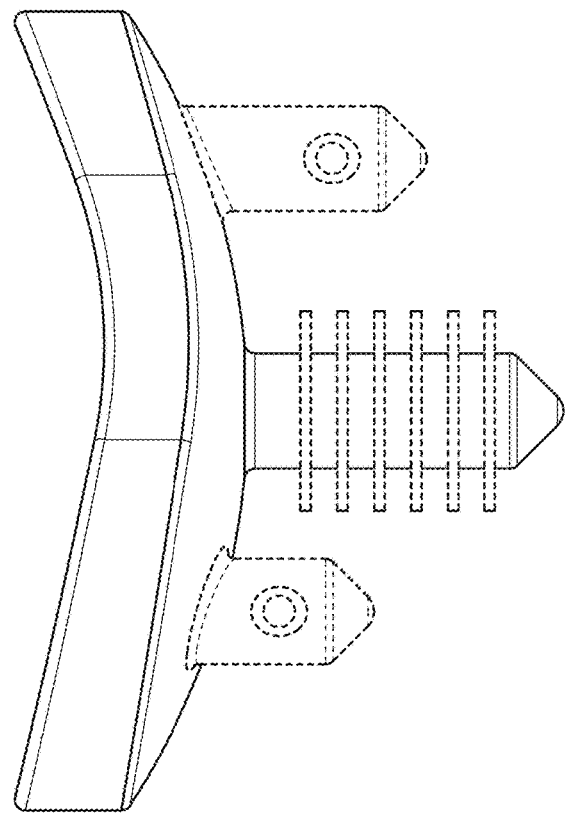
FIG. 32 is a side elevation view of the keeled glenoid of FIG. 30.
Figure 33:
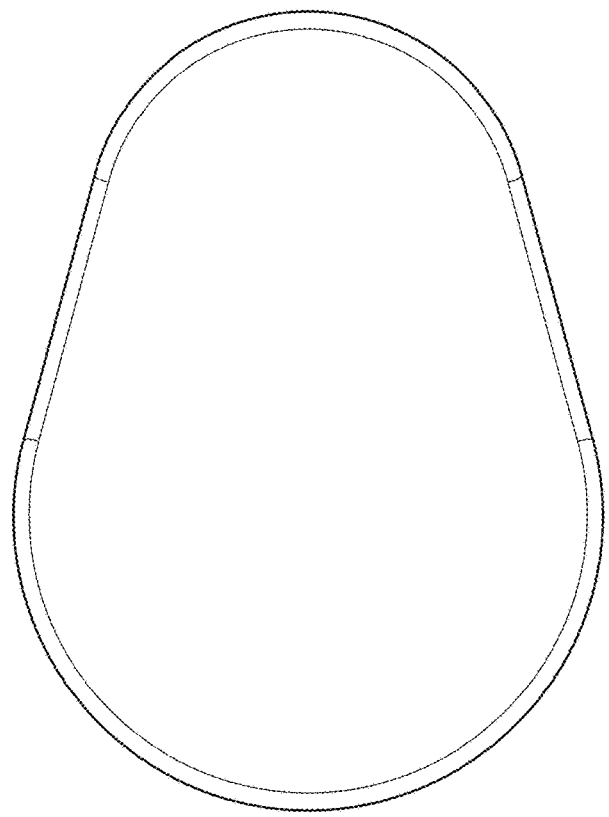
FIG. 33 is a bottom plan view of the keeled glenoid of FIG. 30.
Figure 34:
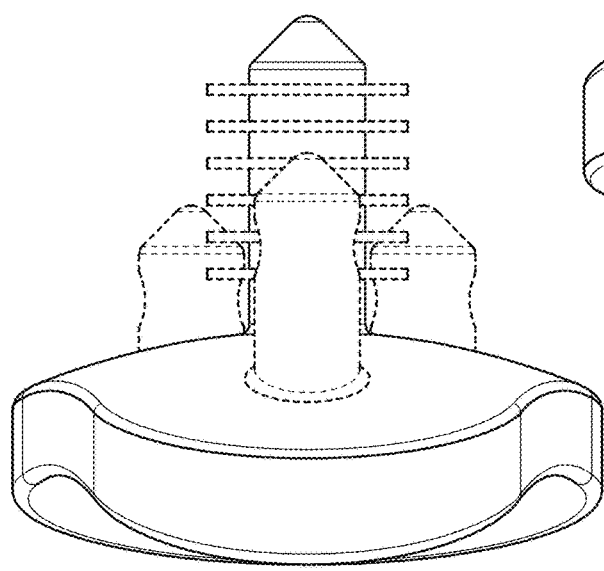
FIG. 34 is a front elevation view of the keeled glenoid of FIG. 30.
Figure 35:
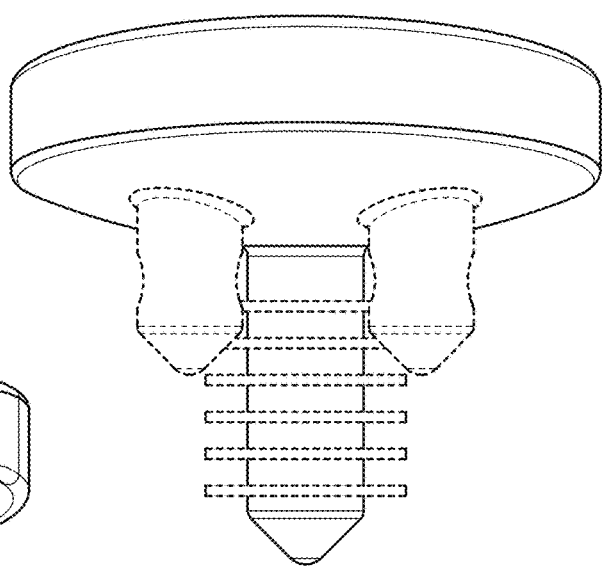
FIG. 35 is a back elevation view of the keeled glenoid of FIG. 30.
Figure 36:
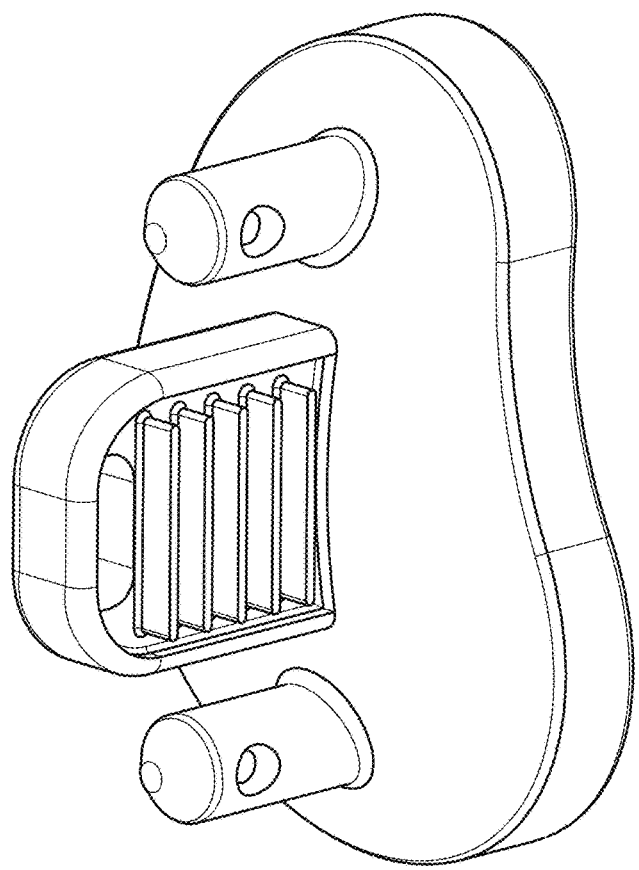
FIG. 36 is a perspective view of an embodiment of a keeled glenoid.
Figure 37:
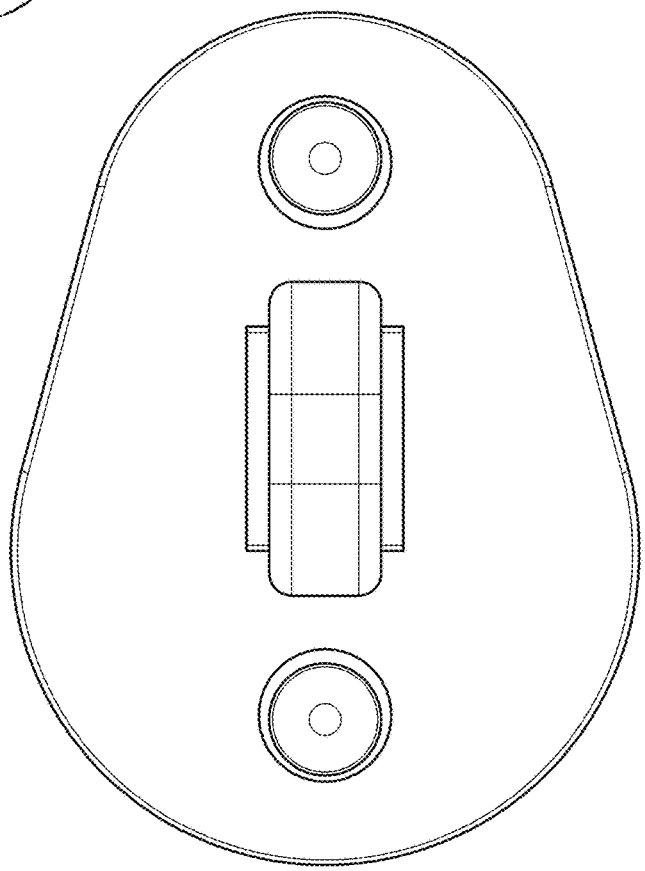
FIG. 37 is a top plan view of the keeled glenoid of FIG. 36.
Figure 38:
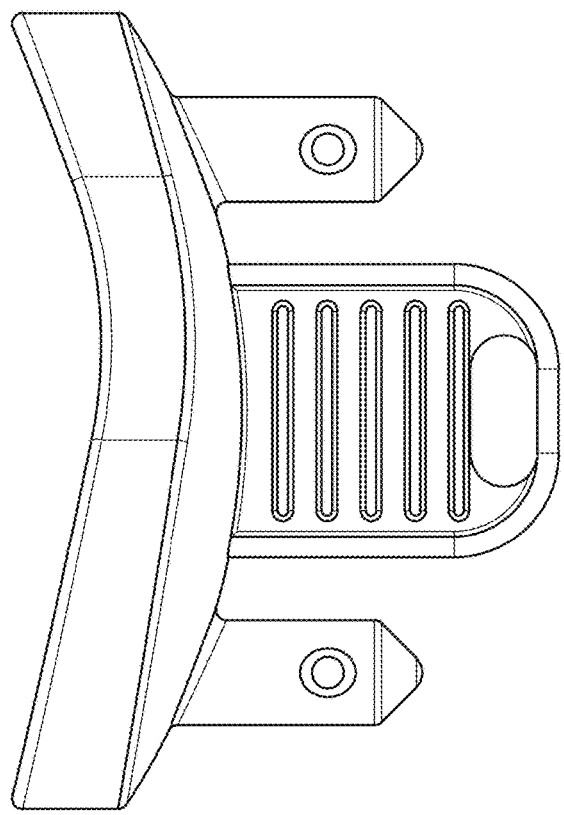
FIG. 38 is a side elevation view of the keeled glenoid of FIG. 36.
Figure 39:
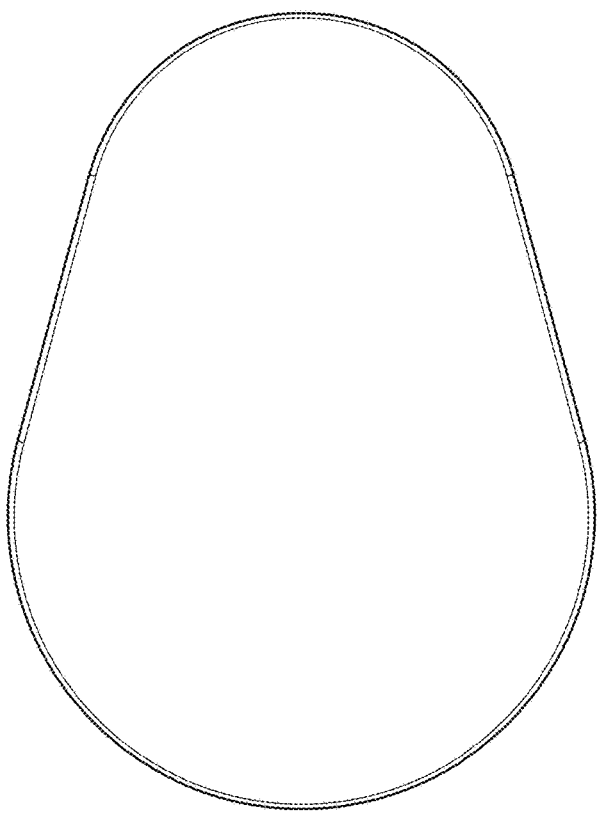
FIG. 39 is a bottom plan view of the keeled glenoid of FIG. 36.
Figure 40:
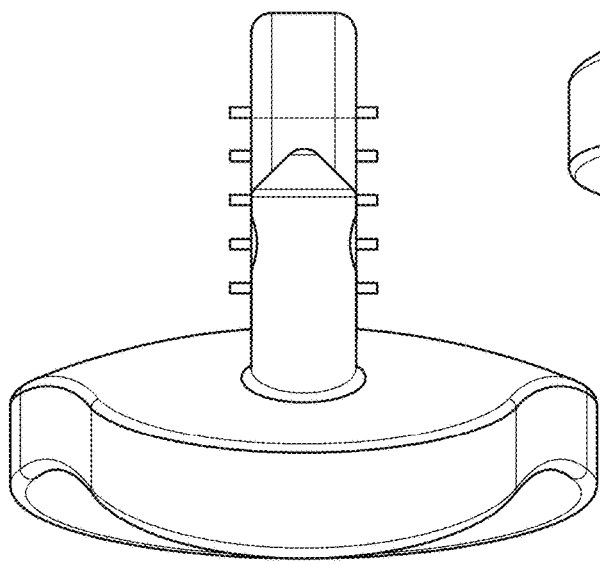
FIG. 40 is a front elevation view of the keeled glenoid of FIG. 36.
Figure 41:
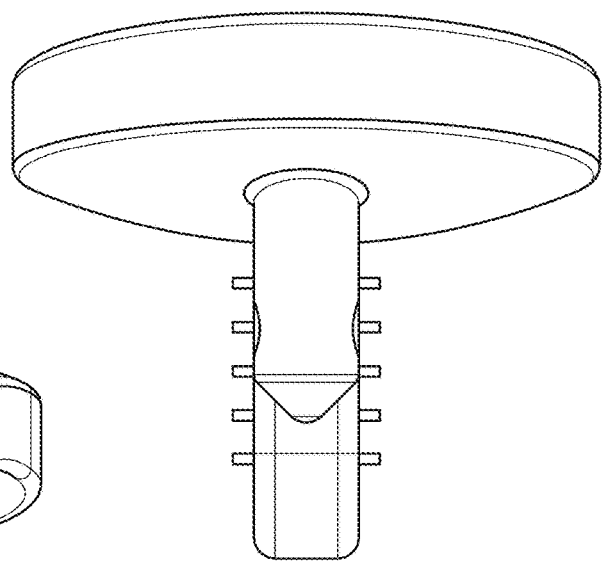
FIG. 41 is a back elevation view of the keeled glenoid of FIG. 36.
Figure 42:
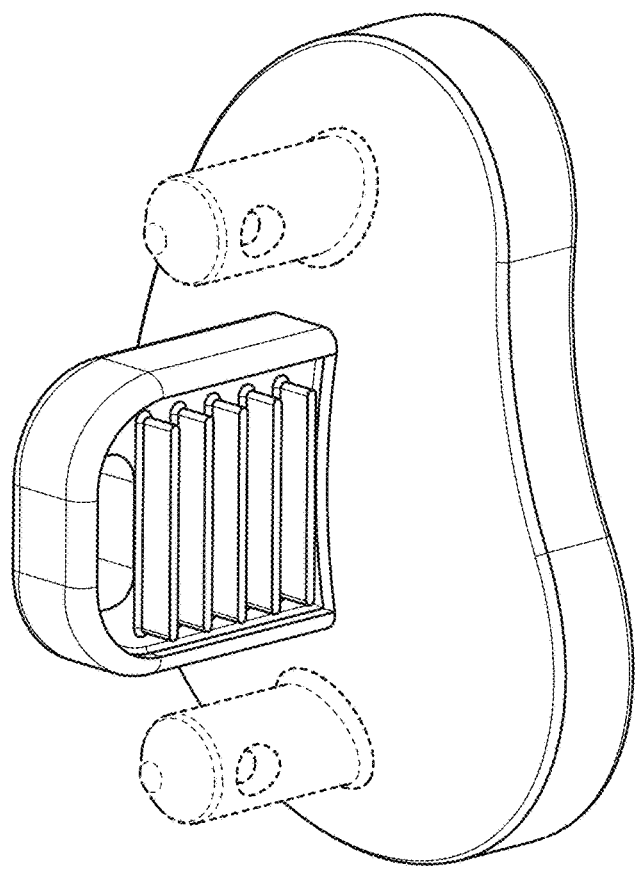
FIG. 42 is a perspective view of an alternate embodiment of a keeled glenoid of FIG. 36.
Figure 43:
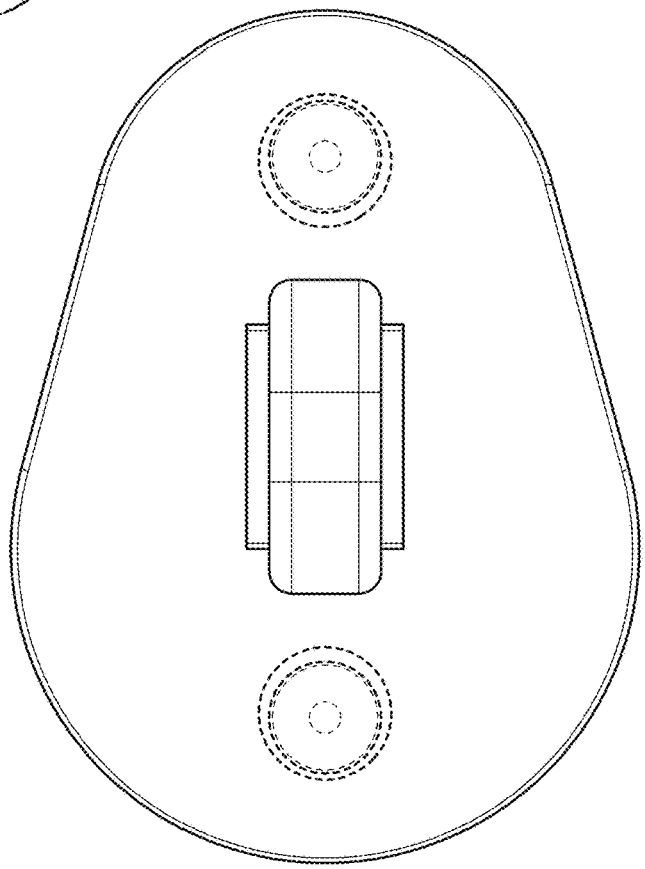
FIG. 43 is a top plan view of the keeled glenoid of FIG. 42.
Figure 44:
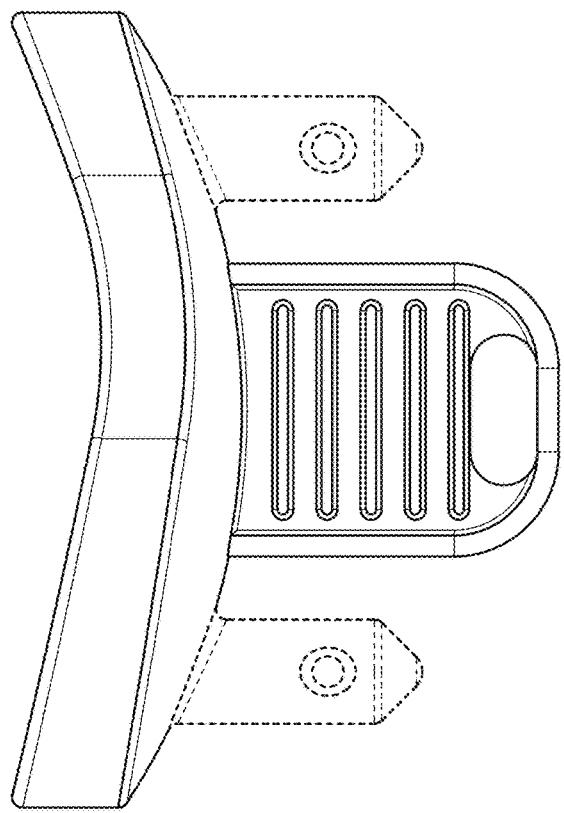
FIG. 44 is a side elevation view of the keeled glenoid of FIG. 42.
Figure 45:
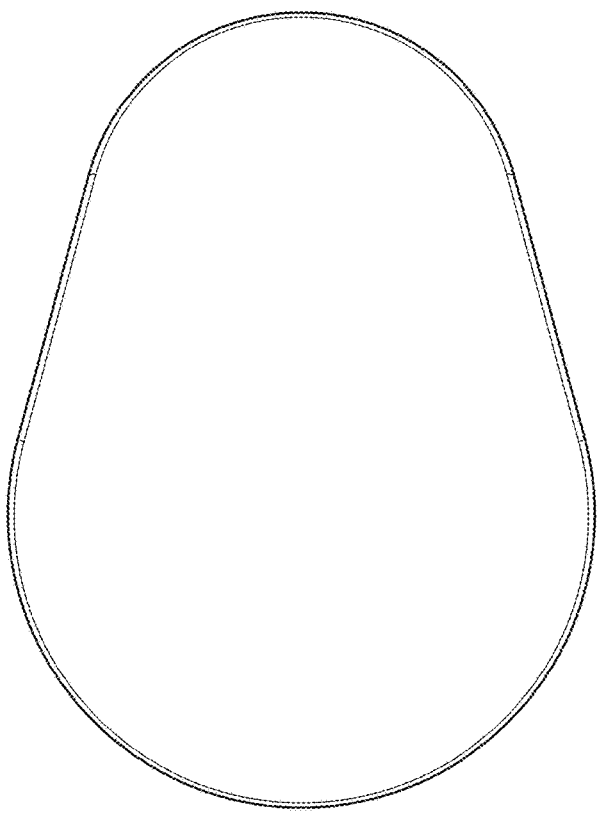
FIG. 45 is a bottom plan view of the keeled glenoid of FIG. 42.
Figure 46:
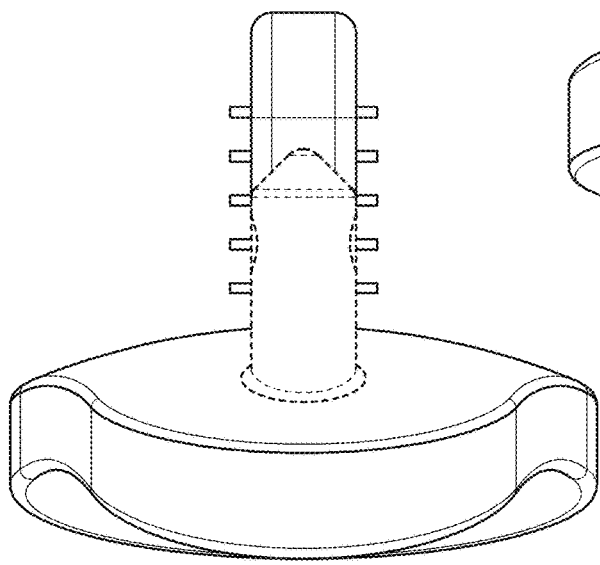
FIG. 46 is a front elevation view of the keeled glenoid of FIG. 42.
Figure 47:
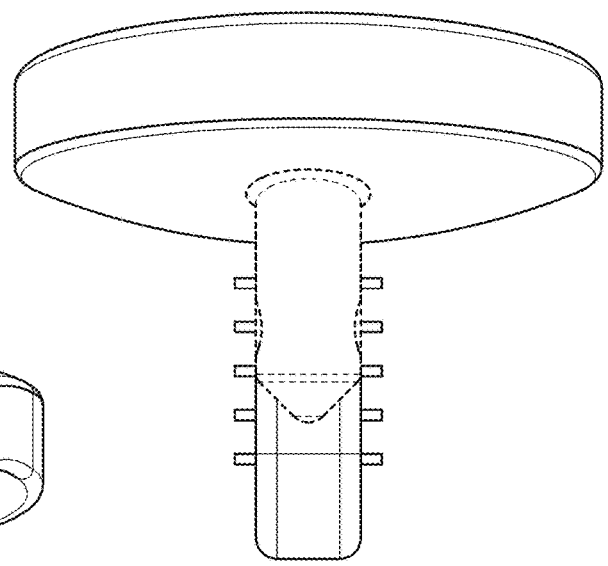
FIG. 47 is a back elevation view of the keeled glenoid of FIG. 42.
Figure 48:
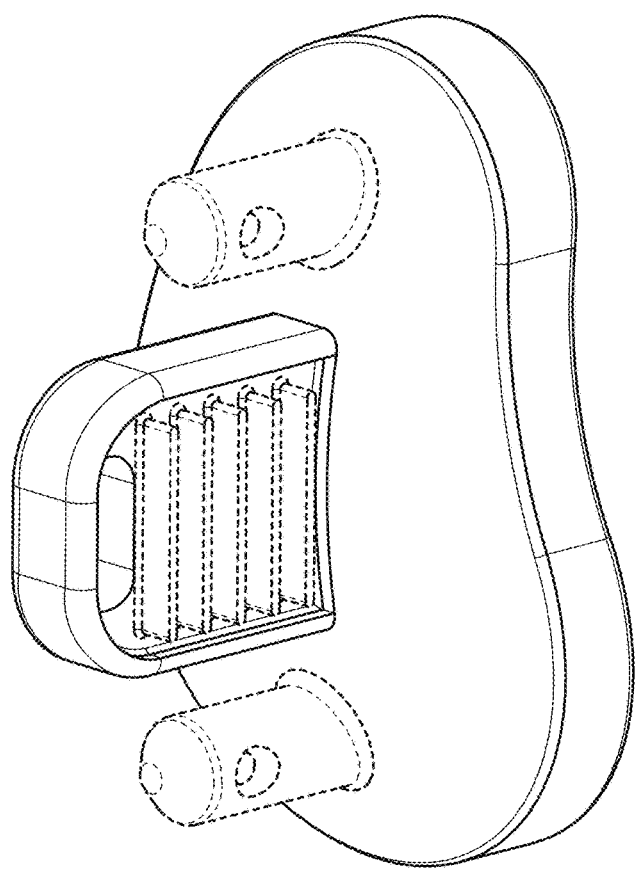
FIG. 48 is a perspective view of an alternate embodiment of a keeled glenoid.
Figure 49:
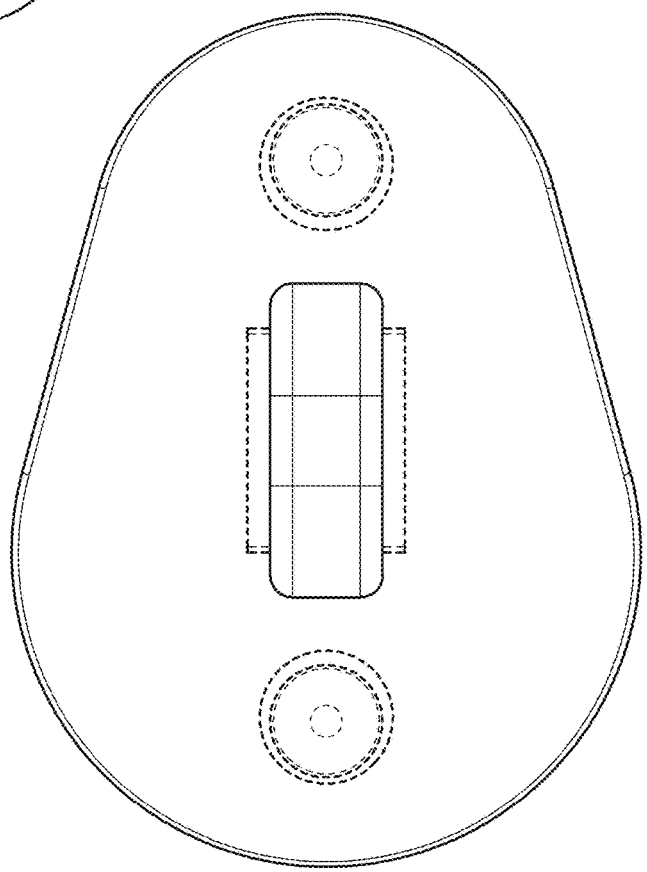
FIG. 49 is a top plan view of the keeled glenoid of FIG. 48.
Figure 50:
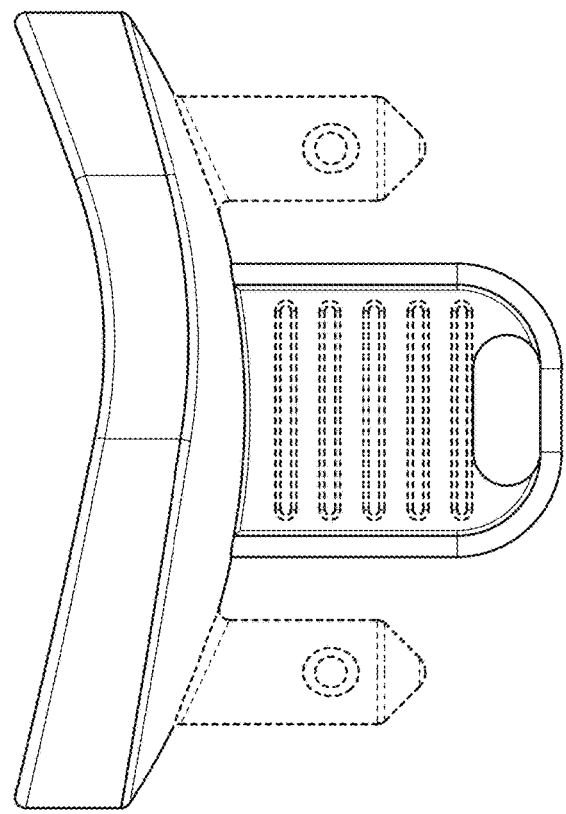
FIG. 50 is a side elevation view of the keeled glenoid of FIG. 48.
Figure 51:
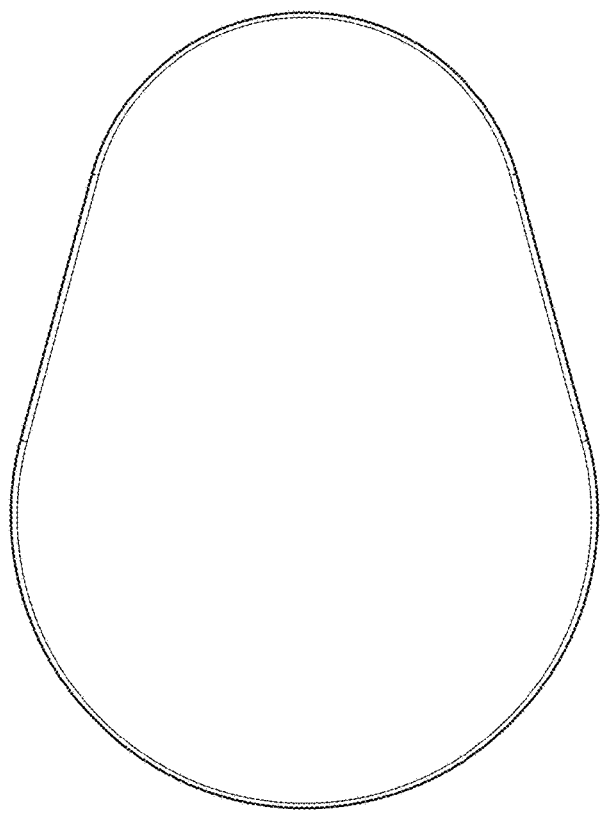
FIG. 51 is a bottom plan view of the keeled glenoid of FIG. 48.
Figure 52:
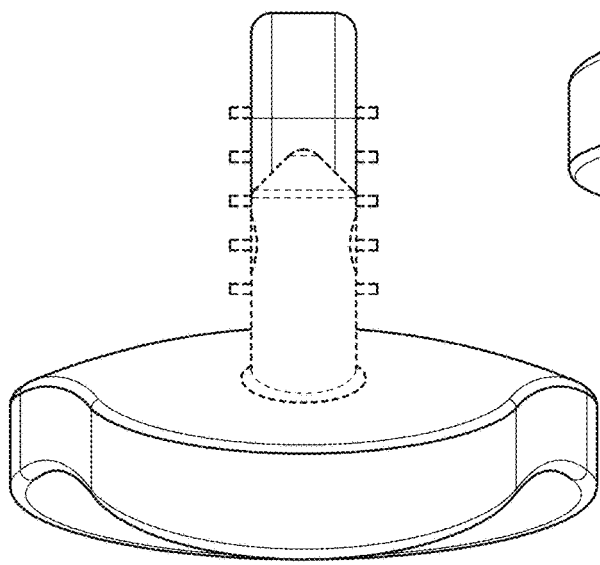
FIG. 52 is a front elevation view of the keeled glenoid of FIG. 48.
Figure 53:
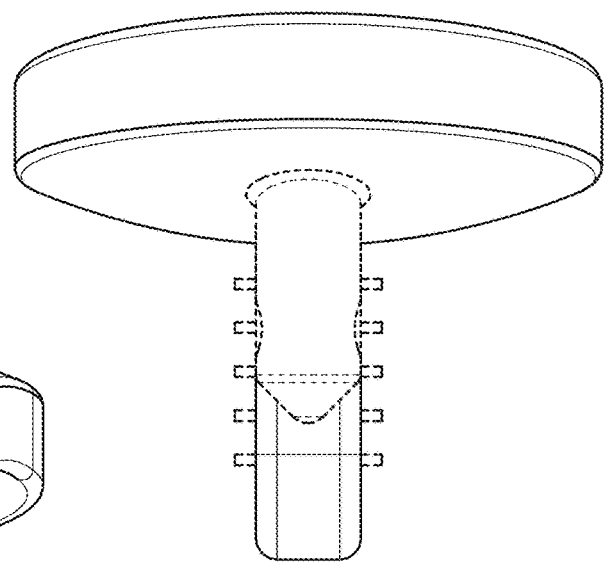
FIG. 53 is a back elevation view of the keeled glenoid of FIG. 48.
Figure 54:
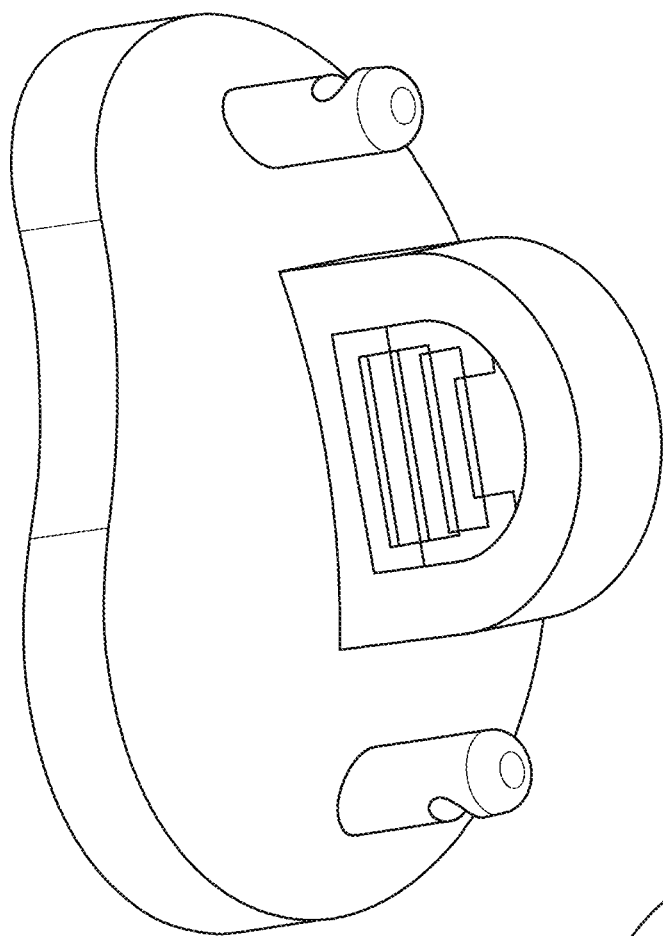
FIG. 54 is a perspective view of an alternate embodiment of a keeled glenoid.
Figure 55:
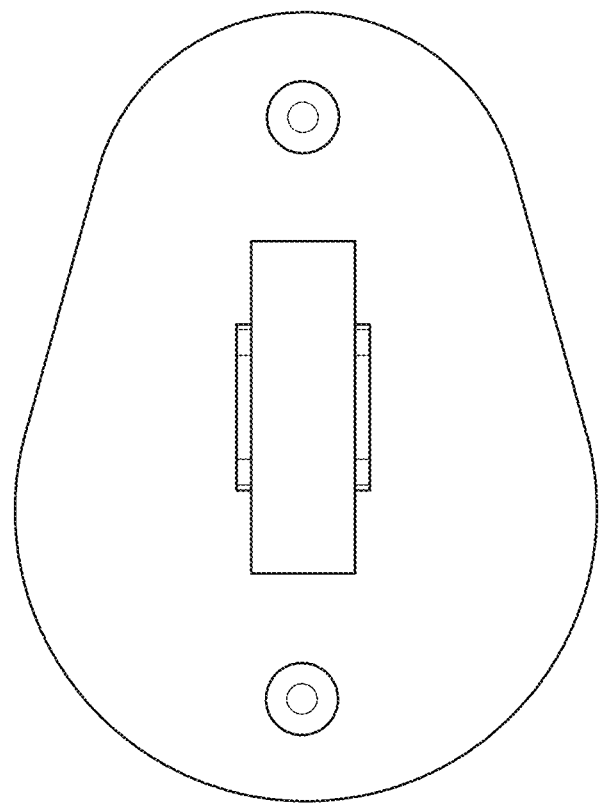
FIG. 55 is a top plan view of the keeled glenoid of FIG. 54.
Figure 56:
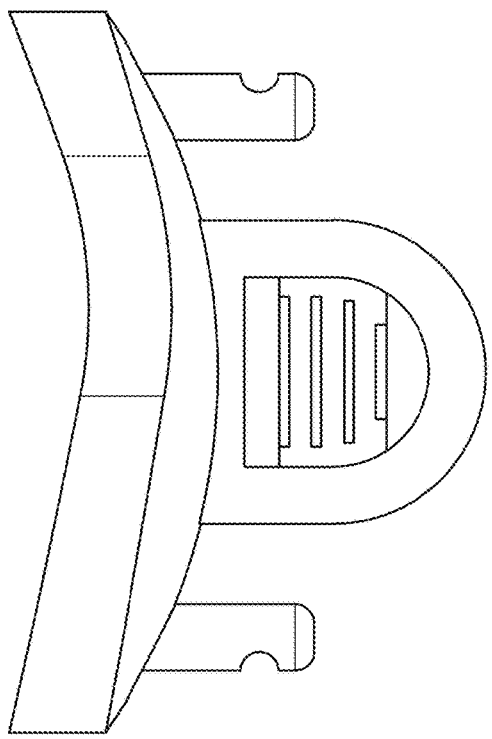
FIG. 56 is a side elevation view of the keeled glenoid of FIG. 54.
Figure 57:
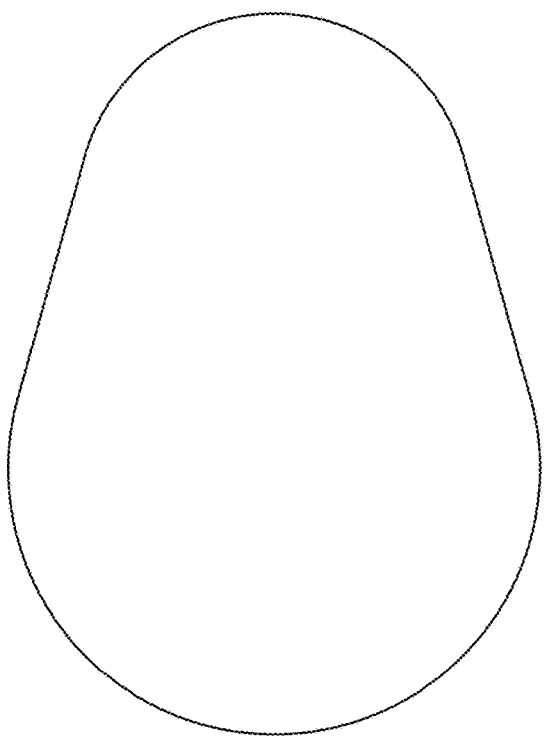
FIG. 57 is a bottom plan view of the keeled glenoid of FIG. 54.
Figure 58:
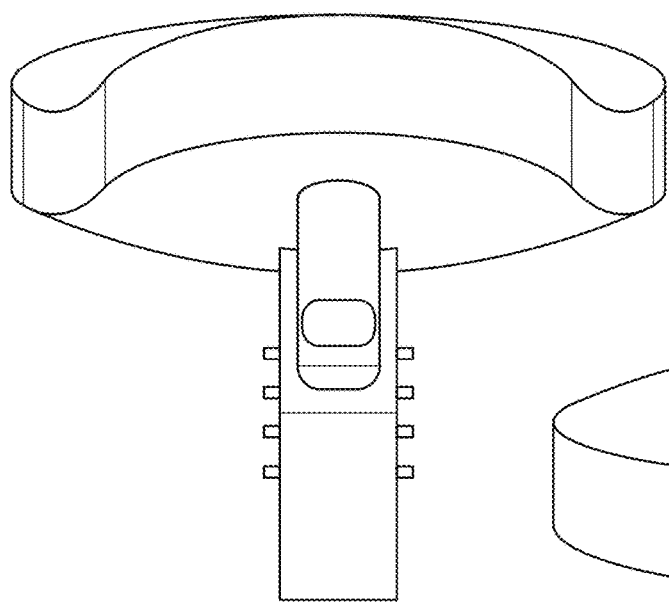
FIG. 58 is a front elevation view of the keeled glenoid of FIG. 54.
Figure 59:
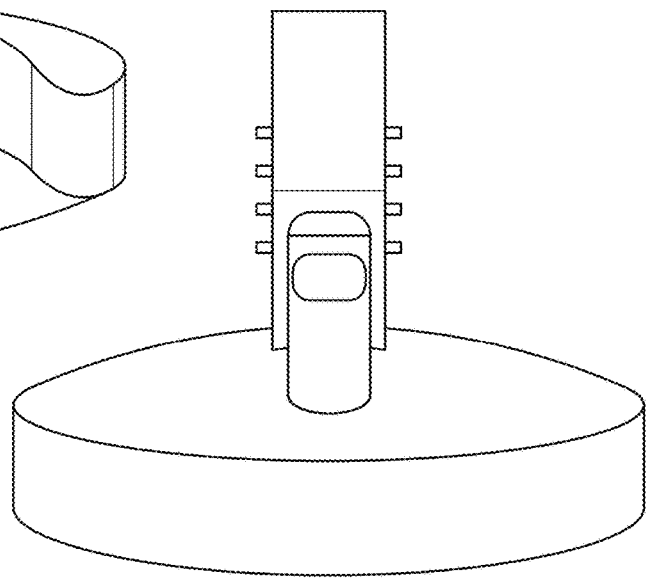
FIG. 59 is a back elevation view of the keeled glenoid of FIG. 54.
Figure 60:
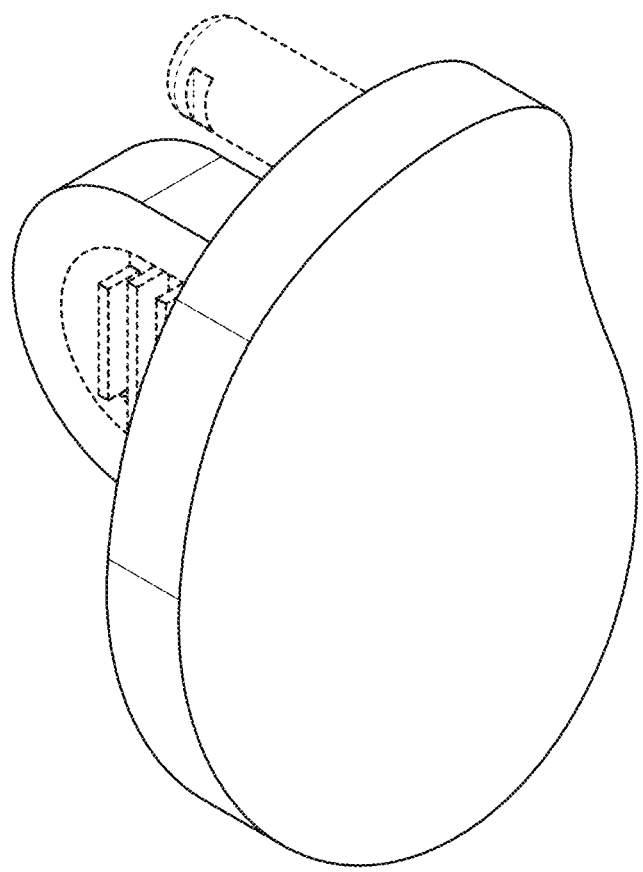
FIG. 60 is a perspective view of an alternate embodiment of a keeled glenoid of FIG. 54.
Figure 61:
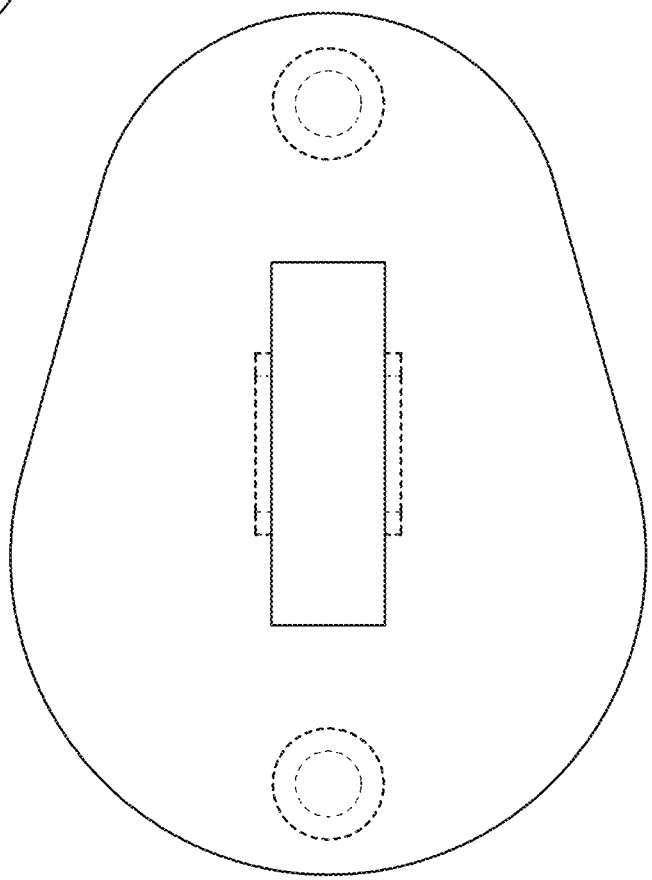
FIG. 61 is a top plan view of the keeled glenoid of FIG. 60.
Figure 62:
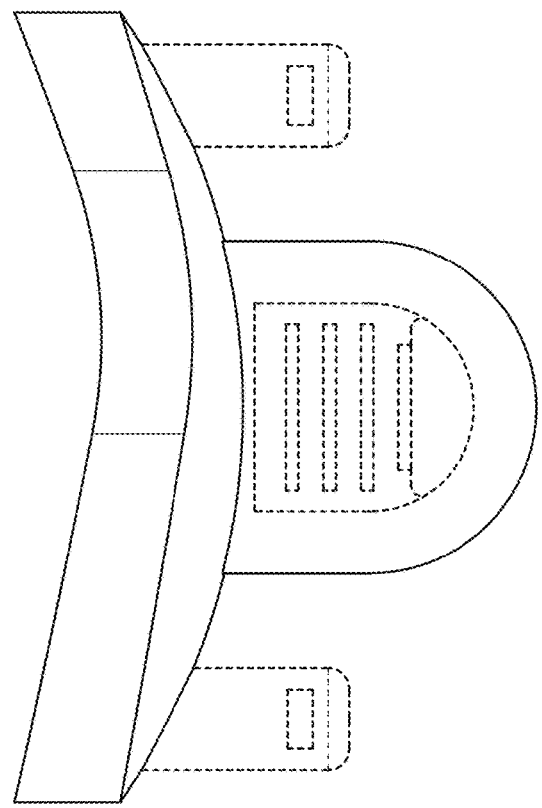
FIG. 62 is a side elevation view of the keeled glenoid of FIG. 60.
Figure 63:
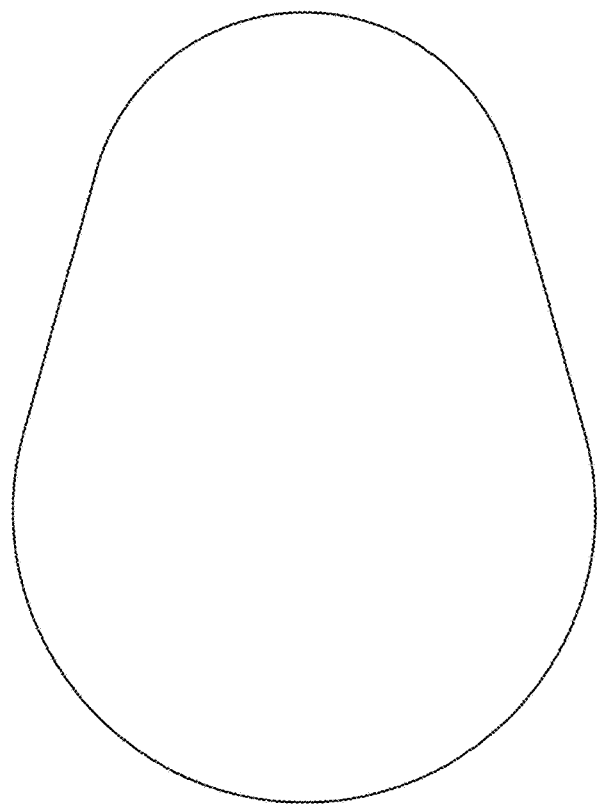
FIG. 63 is a bottom plan view of the keeled glenoid of FIG. 60.
Figure 64:
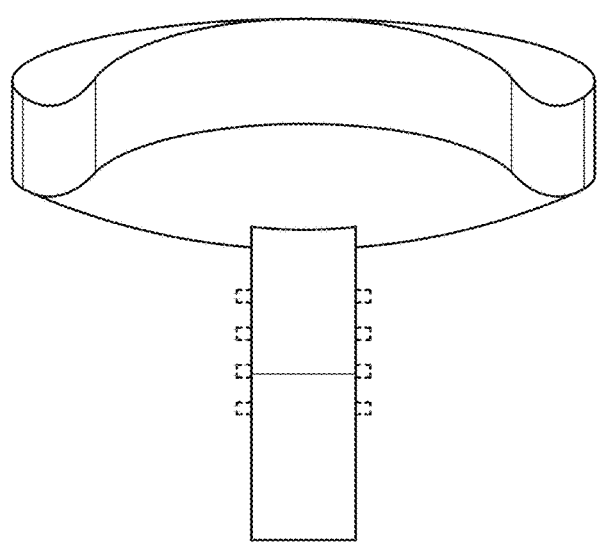
FIG. 64 is a front elevation view of the keeled glenoid of FIG. 60.
Figure 65:
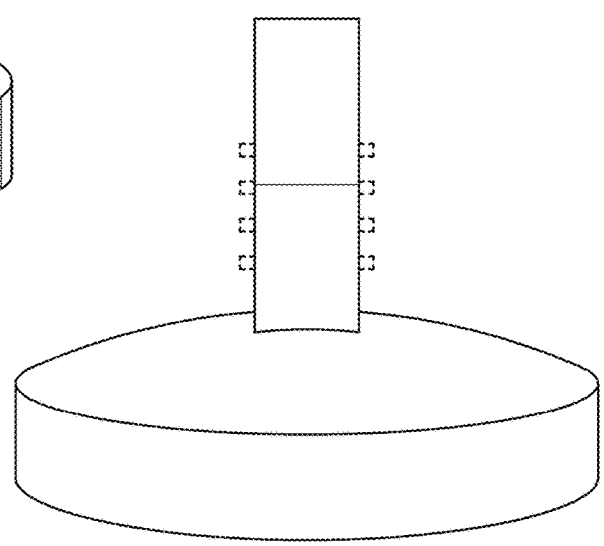
FIG. 65 is a back elevation view of the keeled glenoid of FIG. 60.

Referring now to FIG. 17, the metaphyseal shell coupler component is shown in an array of sizes of a representative embodiment with side, top and bottom views in each of the top, middle and bottom panels, respectively, whereby the position of the anchor engagement feature may vary to provide an array of shells for selection to provide a customized fit and engagement for a humeral head or cup prosthesis. In the various embodiments, a metaphyseal shell with an offset for engagement with an anchor is selected from offsets ranging in mm and increments thereof from 0 to 20 mm, and includes 0, 1, 2, 3, 4, 5, 6, 7, 8, 9, 10, 11, 12, 13, 14, 15, 16, 17, 18, 19, and 20. In some representative embodiments, the range of offset may be from 0 to 10, and in some specific embodiments, the offset may be from 0 to 6. Referring again to the drawings, FIG. 17 shows an exemplary set of metaphyseal shells representing offsets of 0, 1, 2, and 3 mm. In accordance with the representative array, the metaphyseal shells may vary in diameter from about 30 to 45 mm, more particularly from 34 to 40 mm, and in some specific embodiments include sizes that are 34, 36, 38 and 40 mm in diameter, respectively. Of course other sizes and incremental portions thereof are possible, and can range from 5 mm to more than 100 mm in diameter depending on the subject. Thus, metaphyseal shells may be provided in heights ranging in mm increments and fractions thereof from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to 100, and in diameters in mm increments and fractions thereof from 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to 100.

It will be appreciated that any range of offsets may be provided, and that series of offsets on metaphyseal shells of different diameters and heights, as described herein below, may be provided. In use, in a representative example of a modular arthroplasty system, as depicted in the drawings, a metaphyseal shell is selected for its height, diameter, and engagement feature offset using tools for offset measurement as described further herein below. The selected metaphyseal shell is placed in the bone, its male taper engaged with the female taper of the stem; a set screw is inserted through the taper to engage the metaphyseal shell with the stem to secure the implant system in preparation for engagement with the humeral head or cup prosthesis.

It will be appreciated that the metaphyseal shell is in some embodiments adapted for use above the bone cut line, partially below the bone cut line, or as more particularly described and shown herein, countersunk essentially completely below the bone cut line. The advantages of the metaphyseal shell as described herein can be realized in any implant configuration whether above, or partially or fully recessed below the bone cut line, particularly to enable customized selection and fit of implant components without being constrained by inventory limitations or by less than desirable implant height, neck angle, version, and posterior and medial offset.

In some embodiments, the use of the metaphyseal shell with the elliptical heads enable surgical techniques wherein the metaphyseal shell is completely or partially recessed within the humeral bone (i.e., below the cut line) to allow a greater range of options with respect to establishing the desired center of rotation in the shoulder joint. According to such embodiments, the elliptical head is engaged concentrically with the metaphyseal shell. It is known in the art and deemed desirable by some to distalize the humerus during a reverse shoulder arthroplasty procedure, putatively because greater height in the humeral implant distalizes the humerus and puts increased tension on the deltoid muscle to compensate for lost rotator cuff function. However, there are clinical and mechanical disadvantages to this distalization. Unfortunately, these disadvantages are not easily avoided with implant systems in the art, particularly in the case of current convertible systems, because of the increased height of the humeral implants from the extension of the stem and other components above the bone cut line of the humerus.

The current disclosure, in various embodiments, provides a modular and convertible arthroplasty system that is low profile, having a substantial reduction of implant height as compared with what is know in the art. These embodiments are desirable for avoidance of distalization, particularly in reverse arthroplasty, enabling the surgeon to avoid mechanical and clinical problems associated with the rotational center of the joint, and enabling the use of other options for achieving soft tissue function to replace the rotator cuff.

Further, in accordance with some exemplary embodiments, the countersunk position of the metaphyseal shell below the bone cut allows the surgeon to achieve a more anatomical configuration than other systems can achieve at time of primary or revision surgery. In particular, the position and features of the metaphyseal shell enable substitution of articulation surface prostheses, and as needed, removal of the metaphyseal shell during a revision. In some embodiments, removal of the metaphyseal shell enables replacement with a metaphyseal shell having an alternate offset to enable maximum flexibility for achieving desired anatomical structure in a revision surgery.

The modular system enables achievement of a more anatomically accurate joint replacement aimed at reducing clinically adverse consequences. And the metaphyseal shell with its eccentric taper enables a wider range of selection of humeral head orientation without compromise of height, neck angle, version, and posterior and medial offset. This offset function, together with the anatomical benefits thereby attained, finally solves a vexing challenge in the art. That is, provision for truly adaptable and convertible, anatomically accurate implants—a challenge that has been heretofore addressed, inadequately at best, with either expansive prosthetic humeral head inventory and/or adjustable systems that sacrifice one or more of the anatomically desirable implant features such as component height, neck angle, version, and posterior and medial offset.

EXAMPLES

Materials and Methods:

Three-dimensional CT scans of 79 proximal humerii from Caucasian subjects from the United States and Australia were examined (47 male; 32 female; ages 17-87, with an average age of 56 years). The models were screened to exclude specimens with osteophytes or other obvious degenerative changes. Bony landmark identification methods and measurement techniques were adapted from previously published studies. In addition, the humeral head of each model was virtually resected to mimic an ideal surgical head resection along the anatomical neck as would be done for shoulder arthroplasty. Measurements of the frontal (SI) and sagittal (AP) diameters of the anatomical neck cross section were made directly on the models. Pearson Correlation Coefficients comparing various humeral measurements were calculated. A strong relationship was defined as r>0.5). The Welch's t-test was used to compare the shape of the ellipse for small (SI<45 mm), medium (45 mm≤SI<52 mm), and large (52 mm≤SI) sized humeral heads, with statistical significance set at p≤0.05.

Results:

Linear regression analysis strongly suggests that the shape of the ellipse become more elongated as humeral head size increases. The Pearson Correlation Coefficient implies a strong linear relationship when comparing the difference between DF and DS lengths (SI-AP) to DF lengths (R=0.67; p-value<0.001), and when comparing the DS/DF ratio to DF lengths (R=0.55; p-value<0.001). Welch's t-test demonstrated that small, medium and large sized humeral heads were significantly different from one another with regards to the shape of the elliptical cross section. Smaller heads were more spherical compared to medium-sized (p=0.05) and large heads (p<0.001). The elliptical shape of the large heads was more elongated (SI>AP) compared to that of medium (p<0.001) and small sized heads (p<0.001). Our results with regards to most other measurements (inclination, humeral head height, medial offset, etc.) were very similar to what has been previously reported.

Discussion:

Several previous anatomic studies have documented that the humeral head is elliptical or ovoid rather than spherical, but in the present study, a more detailed mathematical description of the shape of the humeral head is provided. The formulae derived in this study may be used to calculate average dimensional values for an anatomically shaped humeral head of any given size based on the diameter of the base of the humeral head in the frontal plane. Formulae for calculating the humeral head height, radii of curvature in the frontal and sagittal planes, and diameters of the base of the humeral head in the frontal and sagittal planes are presented. These formulae may be useful in the design of future prosthetic shoulder systems in which the goal is to replicate normal anatomy.

This is the first study to report that the elliptical shape of the base of the humeral head seems to elongate in the frontal plane as humeral head size increases. Prior studies have reported the average difference between the DF and DS measurements at the humeral head base: Iannotti et al reported an average difference of 2 mm; Hertel et al reported a difference of 2.5 mm; Harrold and Wigderowitz reported a difference of 2.1 mm; and Amstutz and Clarke reported a difference of 3.9 mm. The authors of these prior studies did not explore whether the dimensional relationships of the shape of the elliptical humeral head remained constant or not with increasing humeral head size. For the 79 humeral heads used in this study, the average difference between DF and DS measurements at the base of the head was 4.3 mm (standard deviation, ±2 mm; range, −1.3 to 9.3 mm), but the average difference clearly increased in value as humeral head size increased.

The elongation of the elliptical shape of the head base that occurs with increasing humeral head size may be demonstrated in a couple of ways: first, because the slope value is approximately equal to 0.7 for each of the linear regression trend lines equations, it is evident that DS lengthens at a slower rate than DF as humeral head size increases; and second, if the difference between DF and DS is plotted relative to the length of DF, results show that the value of (DF−DS) increases as the humeral head size increases. To substantiate these linear regression analysis results, we compared (DF−DS) values between small, medium, and large humeral head sizes. The difference was statistically significant in comparing DF−DS values in each case (minimum P value=0.022). We concluded that on average, small humeral heads are closer to being spherically shaped, whereas with larger humeral heads, the elliptical shape at the base of the head is typically more elongated.

Conclusion:

This is the first study to report that the shape of the humeral head changes from a more spherical to a more elliptical shape with increasing humeral head size. In other words, the elliptical shape appears to become more elongated as the humeral head size increases. Biomechanical and clinical effects of this newly described phenomenon are not yet well understood, and may have implications for future prosthetic shoulder design.

In accordance with the various embodiments, novel elliptical humeral head prostheses and systems for long bone arthroplasty are provided. The system comprises an array of novel elliptical humeral head prosthesis components where each prosthesis component in the array has a convex articulation surface that is hemi elliptical. This hemi elliptical surface is defined by a major axis, a minor axis, an apex, and a base having an elliptical cross sectional shape defined by a major diameter along the major axis and a minor diameter along the minor axis. Within the array, each prosthesis component is characterized by a ratio relationship of the minor diameter divided by the major diameter of the base.

As described herein in the context of the native anatomy, the major diameter is the diameter at the base of the humeral head in the frontal plane (DF—from S to I) and the minor diameter is the diameter in the sagittal plane (DS—from A to P). Each humeral head prosthesis component in the array has a major diameter and a minor diameter that are not equal, and each of these features is also different from each of the other humeral head prosthesis components in the array. Comparing at two or more prostheses in the array, as the major diameter increases, the ratio of the minor diameter to the major diameter decreases, whereby from smaller to larger, the humeral head prosthesis components vary from having a base with a more circular cross sectional shape to a more elongated elliptical cross sectional shape with increasing size.

In some particular embodiments, with reference to the formulae as set forth in FIG. 2, each of the other humeral head prosthesis components in the array is characterized by having a minor diameter (in millimeters) that is equal to 0.69 times the major diameter (in millimeters) plus an additional length in millimeters of 10.8 millimeters, plus or minus 3 millimeters. Thus, in some embodiments, each humeral head prosthesis component in the array is characterized by having a minor diameter (in millimeters) that is equal to 0.69 times the major diameter (in millimeters) plus an additional length in millimeters that ranges from 6.80 millimeters to 14.80 millimeters.

In yet other embodiments, with further reference to the formulae as shown in FIG. 2, each humeral head prosthesis component in the array may be characterized by the minor diameter having a length that is equal to (0.69 times the major diameter) plus 10.8 mm. And in other embodiments, each humeral head prosthesis component in the array may be characterized by the humeral head prosthesis having a height that is equal to (0.30 times the major diameter) plus 3.2 mm plus or minus 3 mm. In still other embodiments, each humeral head prosthesis component in the array may be characterized by the humeral head prosthesis having along the major axis a radius of curvature that is equal to (0.53 times the major diameter) minus 0.5 mm plus or minus 2 mm. And in still other embodiments, each humeral head prosthesis component in the array may be characterized by the humeral head prosthesis having along the minor axis a radius of curvature that is equal to (0.44 times the major diameter) plus 2.2 mm plus or minus 2 mm.

In further specific embodiments, each humeral head prosthesis component in the array may be characterized by the features of a minor diameter that ranges from about 36 to 51 mm, a major diameter that ranges from about 37 to about 56 mm. And in further specific embodiments, each humeral head prosthesis component in the array may be characterized by a ratio of the minor diameter to the major diameter ranges from 0.87 to 1. And in still other embodiments, each prosthesis component in the array may be characterized by an angle of inclination ranges from 120 degrees to 143 degrees. And in still other embodiments, each prosthesis component in the array may be characterized by and a height of the humeral head prosthesis ranges from about 12 to 25 mm.

It will be appreciated in view of the data provided herein, together with the formulae developed by the inventors, that one or more than one of the above described features may characterize humeral head prosthesis components within the disclosure. And further still, that one or more unique arrays may be provided wherein the two or more prosthesis components in the array include one or any combination of the above described features, such arrays suited to one or more of specific patient populations that represent smaller or larger overall body types, or ethnic or geographical origins. Thus, it should be understood that the examples provided herein with respect to the reported data, and the representative examples of humeral head prostheses and arrays are not limiting and are merely representative of the possible arrays which can be provided based on the disclosure.

In some particular embodiments according to the disclosure, a modular system for long bone arthroplasty is provided. The modular system includes an elliptical humeral head prosthesis, an anchor component, the humeral head prosthesis component engageable with the anchor component to provide an arthroplasty assembly, wherein the position of the humeral head prosthesis component can be varied rotationally around a shared engagement axis with the anchor component.

In some further embodiments of a modular system, the system further comprises a coupler component selected from an array of coupler components where each coupler component in the array includes a humeral head prosthesis component engagement side and an opposite anchor component engagement side, and has sides bounded by a lateral edge. In the various embodiments, the lateral edge may be one of cylindrical, frustoconical and frustohemispherical, and may have a surface treatment or texturing to encourage bony ingrowth or ongrowth. The array of coupler components is characterized by having variably positioned anchor engagement features where each of at least two of the plurality of coupler components comprises at least one anchor engagement feature that is off-center from a center point the central engagement axis of the coupler component, and wherein the off-center engagement feature on each of the at least two coupler components is at a different distance in at least one dimension that is perpendicular to the central engagement axis. In accordance with such embodiments of the modular system, the anchor component is selected from an array in which each anchor component has a proximal portion having a proximal surface for contacting at least a portion of the coupler component and a distal portion for positioning within bone, the proximal portion having an angle of inclination of from about 120 to about 145 degrees and comprising a coupler component engagement feature. Further, according to such embodiments, the humeral head prosthesis component includes on its engagement surface an engagement feature for concentric engagement with the coupler component. In use, each of the selected prosthesis, anchor and coupler components are engaged and the coupler and anchor components are recessed into bone, the arthroplasty assembly achieves alignment of the bone articulation surface of the humeral head prosthesis component with the bone that is anatomically similar to a native long bone. Prior to fixation within the bone, the position of the humeral head prosthesis component can be varied rotationally around a shared central engagement axis with the coupler component to achieve the desired orientation of the elliptical humeral head relative to the humerus and the glenoid. And the position of the anchor component relative to the coupler component can be varied in two dimensions on a plane that is perpendicular to the central engagement axis of the coupler and humeral head prosthesis components by selecting the coupler component from an array comprising a plurality of coupler components that include variably positioned anchor engagement features.

In some embodiments comprising an anchor and coupler component, the anchor engagement component of the coupler component is radially offset from the central axis by from about 1 mm to about 20 mm. And, in some embodiments comprising an anchor and coupler component, the at least one anchor engagement feature of the disc shaped coupler component is radially offset from the central axis at a distance selected from one of about 1 mm to about 8 mm, and from about 1 mm to about 6 mm, and from about 1 mm to about 3 mm.

In accordance with some embodiments, a humeral head prosthesis is provided that is characterized by one or more of the features selected from the group consisting of:

(i) a difference between the major and minor diameters (DMaj–DMin) and the ratio of the minor to major diameters (DMin/DMaj), wherein DMaj–DMin ranges from about 1 to about 15 mm, and wherein DMin/DMaj ranges from about 1 to about 0.8;

(ii) the minor diameter having a length that is equal to (0.69 times the major diameter) plus 10.8 mm, the humeral head prosthesis having a height that is equal to (0.30 times the major diameter) plus 3.2 mm plus or minus 3 mm, the humeral head prosthesis having along the major axis a radius of curvature that is equal to (0.53 times the major diameter) minus 0.5 mm plus or minus 2 mm, the humeral head prosthesis having along the minor axis a radius of curvature that is equal to (0.44 times the major diameter) plus 2.2 mm plus or minus 2 mm.

In some particular embodiments, the prosthesis component is characterized by the features of one of DMaj–DMin=2.6 and DMin/DMaj=0.94, DMaj–DMin=3.7 and DMin/DMaj=0.92, and DMaj–DMin=5.8 and DMin/DMaj=0.89. And in yet other embodiments, the humeral head prosthesis component is characterized by having a minor diameter (in millimeters) that is equal to 0.69 times the major diameter (in millimeters) plus an additional length in millimeters that ranges from 7.80 millimeters to 13.80 millimeters. And in still further embodiments, the humeral head prosthesis is characterized by one or more of the features selected from a minor diameter that ranges from about 36 to 51 mm, a major diameter that ranges from about 37 to about 56 mm, a ratio of the minor diameter to the major diameter ranges from 0.87 to 1, an angle of inclination ranges from 120 degrees to 143 degrees, and a height of the humeral head prosthesis ranges from about 12 to 25 mm.

It will be appreciated by one of ordinary skill that the various elliptical humeral head prostheses, and arrays of prostheses may be provided for use in conjunction with the modular systems and assemblies as described herein or may be adapted for use with other modular assemblies. And in some uses, the hemi elliptical humeral heads as described herein may be adapted for use in monolithic designs that include an attached anchor rather than engageable with a modular anchor. Thus, it should be understood that the examples and representative embodiments are not limiting with respect to the use of the novel elliptical humeral head generally characterized by a ratio relationship of the minor diameter divided by the major diameter of the base, the array comprising a plurality of humeral head prosthesis components, each having a major diameter and a minor diameter that is different from each of the other humeral head prosthesis components in the array, wherein as the major diameter is increased the ratio of the minor diameter to the major diameter is decreased, whereby the humeral head prosthesis components vary from having a base with a more circular cross sectional shape to a more elongated elliptical cross sectional shape with increasing size.

Additional Shoulder Arthroplasty Components

This disclosure contemplates shoulder arthroplasty components that are suitable for engagement and articulation with the prostheses components of the modular arthroplasty assemblies disclosed herein. Accordingly, provided herein are exemplary embodiments of glenoid implants suitable for implantation and engagement with a humeral head prosthesis as described herein.

In some embodiments, the glenoid implant is a new keel-type glenoid prosthesis that is improved over those in the art to enhance anchoring of the glenoid in the spongy part of bone, particularly during the immediate post implantation period, when mechanical engagement of the glenoid is most vulnerable. In various embodiments, the glenoid implant has two opposing surfaces. On one of its surfaces is an articulation surface adapted to cooperate with a humeral head. The opposing surface is adapted for engagement with the glenoid cavity, and includes a keel for anchoring it in the glenoid cavity of a shoulder. The keel extends from the glenoid cavity surface of the component and adapted to be immobilized in the glenoid cavity. The keel has two opposing faces, each of which face comprises at least one projecting fin that runs generally parallel to the glenoid surface and extends over at least a part of the perimeter of the keel. In alternate embodiments, the keel includes a plurality of fins aligned substantially in parallel with one another and to the surface of the glenoid and each extending over at least a part of the perimeter of the keel.

In some embodiments, the keel has fins that extend around the entire perimeter of the keel, covering both opposing faces. In alternate embodiments, the one or plurality of fins is located on one or both faces of the keel. In yet other embodiments, each face of the keel comprises a recess and the fins cover the surface of the recessed area but do not extend onto the remainder of the keel surfaces. In the various embodiments, the keel fins are flexible. It is the flexibility and arrangement of the fins on the keel faces that provide improved fixing of the glenoid in the glenoid cavity and ensure resistance of the glenoid to pull out from the cavity. The keel can be adapted for inclusion of bone growth promoters. In its various embodiments, the finned keel further provides a substrate to encourage boney growth over time to further secure the glenoid prosthesis in the glenoid cavity.

In various embodiments, the glenoid implant may incorporate one or more of the following features, in all technically permissible combinations: The body of the keel has in cross section a circular or a non-circular peripheral contour. The fin or at least one of the fins extends in a plane substantially perpendicular to a longitudinal main axis of the keel. The keel has a semicircular shaped cross section and an eccentric position relative to a central axis of the glenoid prosthesis. The fin or at least one of the fins has a substantially semicircular peripheral contour. The keel comprises a first series of substantially parallel fins. The fins are made of a deformable material chosen from materials such as polyethylene or other polymer materials. The keel may have any of varied dimensions and shapes. In some embodiments, the cross section has a non-circular peripheral contour, and for example may be generally frustohemispherical and frustoconical in shape with a substantially elliptical base, and in some embodiments may have a base which is elliptical or substantially square or rectangular. The glenoid implant may be augmented in a manner consistent with augmentation known in the art to compensate for bone loss and other defects in the surgical site.

Patient-Specific Glenoid Component and Method for Creating Said Component

It has been reported that preserving subchondral bone may be important for long-term longevity of the glenoid component. Based on this, there is currently a commercialized glenoid that allows the surgeon the opportunity to minimize glenoid reaming by choosing a glenoid component that most closely matches the native glenoid. However, degenerative, inflammatory, or post-traumatic arthrosis of the glenoid often leads to glenoid deformity resulting in a very irregular glenoid surface. For example, a typical pattern seen in osteoarthritis is one where the posterior portion of the glenoid has been severely eroded, while the anterior portion is left relatively unscathed (as seen with a Walch Type 2B glenoid). When the glenoid is deformed in this manner, excessive reaming is often necessary in order to create a bony surface that mates well with the back side of a prosthetic glenoid. To address this problem of posterior glenoid wear, some have advocated the use of a stepped prosthetic glenoid—that is, one where the posterior aspect of the glenoid is thicker in order to fill the bony void. It has been reported that a stepped design for an augmented glenoid component has superior fixation and less anterior glenoid liftoff in the presence of eccentric loading and may have better long-term clinical results. It has also been reported that augmented components may be better for correcting the glenoid version to neutral while also requiring less bone removal from the glenoid face. However, augmented glenoid components may be technically difficult to implant due to the difficulty of exposing the posterior glenoid during surgery. In cases of extreme posterior erosion, additional bone removal to prepare the posterior glenoid may result in injury to the suprascapular nerve. In addition, all prosthetic components to date require some amount of reaming of the glenoid face.

What is needed is a glenoid prosthesis that may be implanted without any reaming of the glenoid face at all.

Method for Preparing a Glenoid Face to Receive a Glenoid Component:

Obtain a 3D model of a patient's proximal humerus and glenoid using a CT scanner or other imaging modality.

Using 3D computer modeling, create a concave surface that replicates, or at least approximates, the surface of the glenoid in the pre-pathologic state and place this over the native, deformed glenoid (controlling for inclination, version, radius of curvature, and offset).

Use computer modeling to "backfill" from this ideal surface to the deformed surface of the native glenoid, resulting in a prosthetic glenoid that fits perfectly onto the deformed glenoid, filling any voids without the need for surface reaming of the glenoid face.

Add protrusions (pegs or keels, for example) to the newly created glenoid prostheses to anchor the prosthesis to the bone, taking advantage of where the best remaining bone for fixation is located.

Use a multi-axial milling machine to manufacture a prosthetic glenoid of the shape and size of this patient-specific model. This completes the creation of the custom glenoid component.

Create a second copy of the prosthetic glenoid, but without the anchoring protrusions.

In this second model, add holes to which drill guides may be attached. The holes should align with the position of the pegs or keels on the prosthetic component. Print a 3D model of this.

During surgery, the surgeon will clear the face of the glenoid by scraping away any remaining cartilage or soft tissue, but reaming the face is not necessary.

The 3D drill guide model may then be placed so that it mates with the face of the native glenoid. Temporary fixation may or may not be used (i.e. k-wires). The holes may then be drilled into the bone using this patient-specific guide.

The final, custom prosthesis may then be inserted.

It will be appreciated that the individual components of the prosthetic implants disclosed herein may be made using a variety of materials, including metal, ceramic and plastic and combinations of these. Such materials include but are not limited to: metals such as, for example, stainless steel, titanium alloys, cobalt alloys, cobalt chrome, superelastic metals, such as nitinol, polymers, such as polyester and polyethylene, polyether ether ketone (PEEK), carbon and carbon fiber materials. Porous coatings may be provided for any or a portion of the components, and specifically as described herein or as otherwise known in the art. The components may be provided with HA either dispersed on all or a portion of a surface, dispersed within all or a portion of the material of manufacture, and combinations of these.

Of course it will be appreciated by one of ordinary skill in the art that while this application is directed in its examples to the humerus, the application is not necessarily limited to the humerus and the principles, prosthesis systems and methods can be more generally applicable to arthroplasty for achieving native anatomy in the context of other bones.

This disclosure describes exemplary embodiments in accordance with the general inventive concepts and is not intended to limit the scope of the invention in any way. Indeed, the invention as described in the specification is broader than and unlimited by the exemplary embodiments and examples set forth herein, and the terms used herein have their full ordinary meaning.

The general inventive concepts are described with occasional reference to the exemplary embodiments and the exemplary embodiments depicted in the drawings. Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts.

To the extent used herein, the singular forms "a," "an," and "the" are intended to include the plural forms as well, unless the context clearly indicates otherwise. The term "proximal" to the extent used herein in connection with any object refers to the portion of the object that is closest to the operator of the object (or some other stated reference point), and to the extent used herein, the term "distal" refers to the portion of the object that is farthest from the operator of the object (or some other stated reference point). The terms "surgeon" and "operator" to the extent used herein are used interchangeably herein and each is intended to mean and refer to any professional or paraprofessional who delivers clinical care to a medical patient, particularly in connection with the delivery of care, including but not limited to a surgeon. Likewise, the terms "patient" and "subject" to the extent used herein are used interchangeably herein and each is intended to mean and refer to any clinical animal subject, including a human medical patient, particularly in connection with the delivery of care thereto by anyone, including a surgeon or operator to the extent those terms are used herein.

Spatially relative terms, such as "inner," "outer," "beneath", "below", "lower", "above", "upper" and the like, to the extent used herein, may be used herein for ease of description to describe one element or feature's relationship to another element(s) or feature(s) as illustrated in the drawings. Spatially relative terms may be intended to encompass different orientations of the device in use or operation in addition to the orientation depicted in the drawings. For example, if the device in the drawings is turned over, elements described as "below" or "beneath" other elements or features would then be oriented "above" the other elements or features. Thus, the example term "below" can encompass both an orientation of above and below. Thus, an item may be otherwise oriented (rotated 90 degrees or at other orientations) and the spatially relative descriptors used herein interpreted accordingly. With respect to any references to the extent used herein that may be made relative to an object, or to a body or subject for example that of a human patient, the terms "cephalad," "cranial" and "superior" indicate a direction toward the head, and the terms "caudad" and "inferior" and "distal" indicate a direction toward the feet. Likewise, the terms "dorsal" and "posterior" indicate a direction toward the back, and the terms "ventral" and "anterior" indicate a direction toward the front. And further, the term "lateral" indicates a direction toward a side of the body, the term "medial" indicates a direction toward the mid line of the body, and away from the side, the term "ipsalateral" indicates a direction toward a side that is proximal to the operator or the object being referenced, and the term "contralateral" indicates a direction toward a side that is distal to the operator or the object being referenced. More generally, any and all terms to the extent used herein providing spatial references to anatomical features shall have meaning that is customary in the art. And the terms "frontal" and "sagittal" have the meanings as ordinarily understood in the art with reference to a body, or body part, such as for example the shoulder.

Unless otherwise indicated, all numbers expressing quantities, properties, and so forth as used in the specification, drawings and claims are to be understood as being modified in all instances by the term "about." Accordingly, unless otherwise indicated, the numerical properties set forth in the specification and claims are approximations that may vary depending on the suitable properties desired in embodiments of the disclosure. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

While the disclosed embodiments have been described and depicted in the drawings in the context of the human shoulder, it should be understood by one of ordinary skill that all or various aspects of the embodiments hereof may be used in connection with other species and within any species in any joint in the body.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts, or features into additional embodiments and uses within the scope of the general inventive concepts, even if such embodiments are not expressly disclosed herein. Additionally, even though some features, concepts and aspects of the inventions may be described herein as being a preferred arrangement or method, such description is not intended to suggest that such feature is required or necessary unless expressly so stated. Still further, exemplary, or representative values and ranges may be included to assist in understanding the present disclosure. However, such values and ranges are not to be construed in a limiting sense and are intended to be critical values or ranges only if so expressly stated.

Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

What I claim:

1. A method for implanting a modular system for long bone arthroplasty comprising:

(a) providing arthroplasty components comprising:
  i. an array of prosthesis components, the array comprising a plurality of humeral head prosthesis components each comprising on a first side a bone articulation surface that has an overall generally hemi elliptical convex shape defined by a major axis and a minor axis and comprises an apex and a base that each has an non-circular elliptical cross sectional shape, and on an opposite side, adjacent the base, a bone contact surface
  wherein, when a selected humeral head prosthesis component is positioned for use in a humerus bone, the major axis is oriented along a frontal plane in the direction from inferior to superior and the minor axis is oriented along a sagittal plane from anterior to posterior.

2. The method for implanting a modular system for long bone arthroplasty according to claim 1, wherein the bone contact surface of each humeral head prosthesis component in the array includes on its bone contact surface an engagement surface for engagement with a coupler component, the method further comprising the steps of
  (a) (ii) providing at least one generally disc shaped coupler component having a central axis, a prosthesis component side comprising a recess configured to interchangeably engage both a humeral head prosthesis component and a concave prosthesis component, an opposing side, and a lateral edge that bounds the prosthesis component and opposing sides; and
  (b) selecting one coupler component and one humeral head prosthesis component; and
  (c) at least provisionally establishing the position of the selected coupler component relative to a metaphysis of a long bone.

3. The method for implanting a modular system for long bone arthroplasty according to claim 2, wherein the coupler component comprises on its prosthesis component side at least one prosthesis component engagement feature, and wherein each humeral head prosthesis component in the array comprises on its engagement surface an engagement feature for engagement with the coupler component.

4. The method for implanting a modular system for long bone arthroplasty according to claim 3, further comprising: the step of (d) engaging the selected humeral head prosthesis component into the recess of the prosthesis component side of the coupler component.

5. The method for implanting a modular system for long bone arthroplasty according to claim 4, further comprising: either before or after any one or more of the steps (a) through (d), the step (e) of preparing the bone for receiving the coupler component.

6. The method for implanting a modular system for long bone arthroplasty according to claim 5, further comprising the step of: (f) implanting the coupler component into the metaphysis of the long bone, the coupler component at least partially recessed within the bone.

7. The method for implanting a modular system for long bone arthroplasty according to claim 6, further comprising the step of: (g) selecting the orientation of the major and minor axes of the humeral head prosthesis component relative to a long axis of the long bone by rotating the prosthesis component within the coupler component.

8. The method for implanting a modular system for long bone arthroplasty according to claim 1, each humeral head prosthesis component in the array having a major diameter and a minor diameter that is different from each of the other humeral head prosthesis components in the array, wherein as the major diameter is increased the ratio of the minor diameter to the major diameter is decreased, whereby the humeral head prosthesis components vary from having a base with a more circular cross sectional shape to a more elongated elliptical cross sectional shape with increasing size.

9. The method for implanting a modular system for long bone arthroplasty according to claim 1, wherein the bone contact surface of each humeral head prosthesis component in the array includes on its bone contact surface an engagement surface for engagement with an anchor component, and further comprising the steps of
  (a) (ii) before or after steps (a)(i), (b), (c), and (e) and before steps (d) and (f) providing at least one bone anchor for engagement within at least a portion of a diaphysis of the long bone;
  (b) before or after steps (a)(i), (a)(ii), (c), (e) and (f), and before step (d) preparing the long bone for receiving the anchor component;
  (c) before or after steps (a)(ii), (b), and (d), and before steps (e), (f) and (g) selecting the humeral head prosthesis component from the array;
  (d) before or after steps (a)(i), (c), and (e), and after step (a)(ii) and (b) implanting the anchor component into the long bone, the anchor component at least partially recessed within a metaphysis and the diaphysis of the long bone;
  (e) before or after steps (a)(ii), (b), and (d), and after step (c) at least provisionally establishing the position of the selected humeral head prosthesis component relative to the metaphysis of the long bone;
  (f) after steps (a)(ii) and (b), engaging the selected humeral head prosthesis component with the anchor component; and
  (g) after step (f), selecting the orientation of the major and minor axes of the humeral head prosthesis component relative to a long axis of the long bone by rotating the humeral head prosthesis component relative to the anchor component.

10. A kit for long bone arthroplasty, comprising:
  an array of prosthesis components, the array comprising a plurality of convex prosthesis components each comprising on a first side a bone articulation surface that has an overall generally hemi elliptical convex shape and comprises an apex and a base that each has an non-circular elliptical cross sectional shape, and on an opposite side, adjacent the base an engagement surface for one or more of contact with a bone and engagement with one of a coupler component and an anchor; and
  at least one of:
    (i) at least one generally disc shaped coupler component comprising an convex prosthesis component side comprising a receiving recess for the engagement surface of the convex prosthesis component, and a sidewall that is defined by a lateral edge that bounds the humeral head prosthesis component side and an opposite bone contact side and has a geometry selected from cylindrical, frustoconical and frustohemispherical; and
    (ii) at least one anchor component,
  wherein a selected component from the array of convex prosthesis components is engageable directly or indirectly with one of the coupler component and the anchor component to provide an arthroplasty assembly, wherein the position of the convex prosthesis component can be varied rotationally around an engagement axis with the coupler component or the anchor component.

11. A kit for long bone arthroplasty according to claim 10, the plurality of convex prosthesis components comprising at least two convex prosthesis components, the first of the at least two convex prosthesis components having a first major diameter and a first minor diameter, and the second of the at least two convex prosthesis components having a second major diameter that is greater than the first major diameter and a second minor diameter that is greater than the first minor diameter, and the ratio of the first minor diameter to the first major diameter is greater than the ratio of the second minor diameter to the second major diameter, each convex prosthesis component comprising an articulation surface with an apex that is elliptical, and on an opposite side an engagement surface for concentric engagement with a coupler component.

12. A kit for long bone arthroplasty according to claim 11, wherein each convex prosthesis component in the array is characterized by the feature of a minor diameter having a length that is equal to (0.69 times the major diameter) plus an additional length in millimeters of 10.8 mm, plus or minus 1 or 2 millimeters.

13. A kit for long bone arthroplasty according to claim 11, wherein a plurality of the convex prosthesis components in the array is characterized by the features of a difference between the major and minor diameters (DMaj−DMin) and the ratio of the minor to major diameters (DMin/DMaj) that are selected from DMaj−DMin=2.6 and DMin/DMaj=0.94, DMaj−DMin=3.7 and DMin/DMaj=0.92, and DMaj−DMin=5.8 and DMin/DMaj=0.89.

14. A kit for long bone arthroplasty according to claim 11, wherein each of a plurality of the convex prosthesis components in the array is characterized by one or more of the features selected from a minor diameter that ranges from about 36 to about 51 mm, a major diameter that ranges from about 37 to about 56 mm, a ratio of the minor diameter to the major diameter ranges from about 0.87 to about 1, an angle of inclination that ranges from about 120 degrees to about 143 degrees, and a height of the humeral head prosthesis ranges from about 12 to about 25 mm.

15. A kit for long bone arthroplasty according to claim 11, wherein each of a plurality of the convex prosthesis components in the array is characterized by the features of a radius of curvature along the major axis that is equal to (0.53 times the major diameter) minus 0.5 mm plus or minus 2 mm, and a radius of curvature along the minor axis that is equal to (0.44 times the major diameter) plus 2.2 mm plus or minus 2 mm.

16. A kit for long bone arthroplasty according to claim 10, wherein the prosthesis component side of the coupler component is configured to interchangeably interface with and engage both a convex humeral head prosthesis component and a concave prosthesis component, the kit further comprising a non-elliptical prosthesis component selected from one or more of (i) at least one concave cup having a cross sectional shape that is circular, and (ii) a convex head having a cross sectional shape that is circular.

17. A kit for long bone arthroplasty according to claim 10, comprising:
  at least one anchor component; and
  a plurality of coupler components, each coupler component comprising a prosthesis component engagement side and an opposite anchor component engagement side, the sides bounded by a lateral edge that is one of cylindrical, frustoconical and frustohemispherical, wherein at least two of the plurality of coupler components comprises at least one anchor engagement feature that is off-center from a center point of the coupler component, and wherein the off-center engagement feature on each of the at least two coupler components is at a different distance in at least one dimension that is perpendicular to the center point, wherein a selected component of each of the arrays of prosthesis, anchor and coupler components are engageable to provide an arthroplasty assembly, and wherein the position of the anchor component relative to the coupler component can be varied in two dimensions on a plane that is perpendicular to the central engagement axis of the coupler and prosthesis components by selecting the coupler component from an array comprising a plurality of coupler components that include variably positioned anchor engagement features; and wherein the position of a selected convex prosthesis component can be varied rotationally around a shared central engagement axis with the coupler component for selection of the orientation of the convex articulation surface relative to a glenoid, and an offset position of the prosthesis component can be varied at the engagement of the coupler and anchor components.

18. A kit for long bone arthroplasty according to claim 17, comprising a plurality of anchor components each comprising a proximal portion having a proximal surface for contacting at least a portion of the coupler component and a distal portion for positioning within bone, the proximal portion having an angle of inclination of from about 120 degrees to about 145 degrees relative to along axis of the bone and comprising a coupler component engagement feature.

19. A kit for long bone arthroplasty according to claim 18, wherein the prosthesis component side of the coupler component is configured to interchangeably interface with and engage both a convex prosthesis component and a concave prosthesis component, the kit further comprising a non-elliptical prosthesis component selected from one or more of (i) at least one concave cup having a cross sectional shape that is circular, and (ii) a convex head having a cross sectional shape that is circular.

20. A kit for long bone arthroplasty according to claim 10, comprising a glenoid implant, the glenoid implant comprising an articulation surface for contacting a humeral head, and a glenoid cavity contact surface, the glenoid implant further comprising a keel that extends from the glenoid cavity contact surface, the keel being adapted to be immobilized in bone, wherein the keel comprises on at least a portion of its surface one or a plurality of flexible and deformable fins, each fin extending in a plane that is substantially perpendicular to a longitudinal main axis of the keel and parallel with the glenoid cavity contact surface of the glenoid implant, wherein a plurality of fins are arranged in parallel to one another and spaced equidistant along the longitudinal axis of the keel; and wherein the keel has a shape that is selected from cylindrical and a circular or a non-circular peripheral contour that comprises two opposing faces, each face comprising a plurality of deformable fins.

* * * * *